(12) United States Patent
Tsekos

(10) Patent No.: US 6,904,305 B2
(45) Date of Patent: Jun. 7, 2005

(54) SYSTEM FOR MRI-GUIDED INTERVENTIONAL MAMMARY PROCEDURES

(75) Inventor: Nikolaos V. Tsekos, Creve Coeur, MO (US)

(73) Assignee: Regents of the University of Minnesota, Minneapolis, MN (US)

(*) Notice: Subject to any disclaimer, the term of this patent is extended or adjusted under 35 U.S.C. 154(b) by 382 days.

(21) Appl. No.: 10/028,050

(22) Filed: Dec. 20, 2001

(65) Prior Publication Data

US 2002/0156365 A1 Oct. 24, 2002

Related U.S. Application Data

(62) Division of application No. 09/407,346, filed on Sep. 29, 1999, now Pat. No. 6,675,037.

(51) Int. Cl.⁷ .............................................. A61B 5/05
(52) U.S. Cl. ..................................... 600/417; 606/130
(58) Field of Search ............................... 600/417, 411, 600/427, 429; 606/130; 378/37

(56) References Cited

U.S. PATENT DOCUMENTS

| | | | |
|---|---|---|---|
| 3,971,950 A | * 7/1976 | Evans et al. ................... | 378/37 |
| 4,599,738 A | * 7/1986 | Panetta et al. ................. | 378/37 |
| 5,050,197 A | * 9/1991 | Virta et al. .................... | 378/37 |
| 5,233,994 A | 8/1993 | Shmulewitz ........... | 128/661.08 |
| 5,260,050 A | 11/1993 | Ranney .......................... | 424/9 |
| 5,534,778 A | 7/1996 | Loos et al. .................. | 324/318 |
| 5,569,266 A | 10/1996 | Siczek ......................... | 606/130 |
| 5,678,549 A | 10/1997 | Heywang-Koebrunner et al. ...... | 128/653.5 |
| 5,805,665 A | 9/1998 | Nelson et al. ............... | 378/207 |
| 5,913,863 A | 6/1999 | Fischer et al. .............. | 606/130 |
| 5,971,998 A | * 10/1999 | Russell et al. .............. | 606/130 |
| 6,022,325 A | * 2/2000 | Siczek et al. ................ | 600/568 |
| 6,161,034 A | 12/2000 | Burbank et al. ............ | 600/431 |
| 6,205,352 B1 | 3/2001 | Carroll ........................ | 600/431 |
| 6,214,018 B1 | 4/2001 | Kreizman et al. .......... | 606/130 |
| 6,406,482 B1 | * 6/2002 | Chakeres ..................... | 606/130 |
| 6,675,037 B1 | * 1/2004 | Tsekos ........................ | 600/417 |

* cited by examiner

Primary Examiner—Shawna J. Shaw
(74) Attorney, Agent, or Firm—Schwegman, Lundberg, Woessner & Kluth, P.A.

(57) ABSTRACT

The combination of contrast enhanced magnetic resonance imaging (MRI) and MR-guided subcutaneous core biopsy can be used as a robust approach for the diagnosis and treatment of breast cancer. MRI provides the means to accurately position and monitor interventional procedures such as biopsy, removal of tissue or other transcanular procedures. MRI may also be used in this invention to position and monitor the progress of breast conserving therapies (BCT), such as laser photo-ablation, cryoablation and localized hyperthermia. The general practice of this invention is to provide a remotely controlled apparatus for MR-guided interventional procedures in the breast. The apparatus allows the practice of a method that provides flexibility in conditioning the breast, i.e. orientation and degree of compression, and in setting the trajectory of the intervention. To that end, a robust conditioning/positioning device, fitted with the appropriate degrees of freedom, enhances the efficacy and efficiency of breast interventions by providing the flexibility in planning and executing an appropriate procedure strategy that better suits interventional procedures, either those in current use or yet to be developed. The novelty and potential commercial success of the device originates from its high maneuverability to set and perform the procedure strategy and its adaptability to accommodate an array of interventional probes. Remote control of this device can allow planning the operation and performing the relevant tasks in a short period, for example, within the contrast window provided by a single injection of a contrast agent, and this feature can be operator-independent.

30 Claims, 27 Drawing Sheets

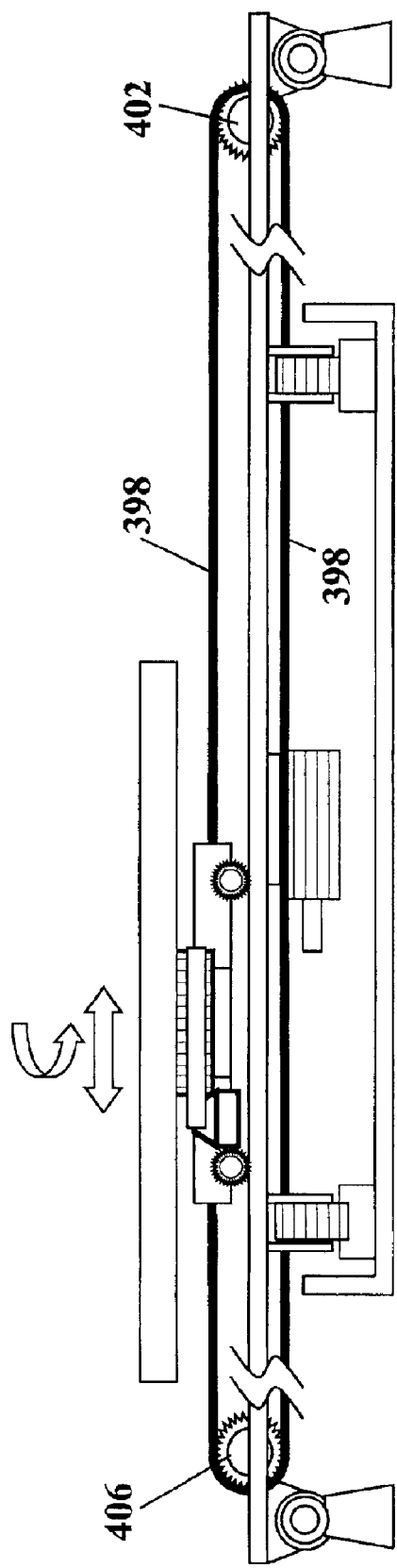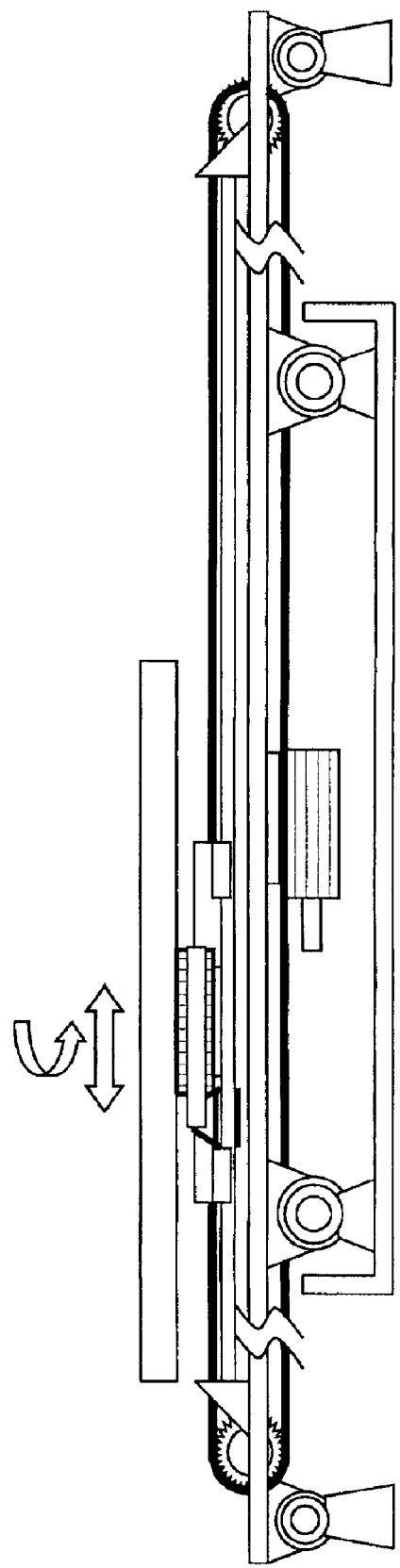
Fig. 8D
Fig. 8E

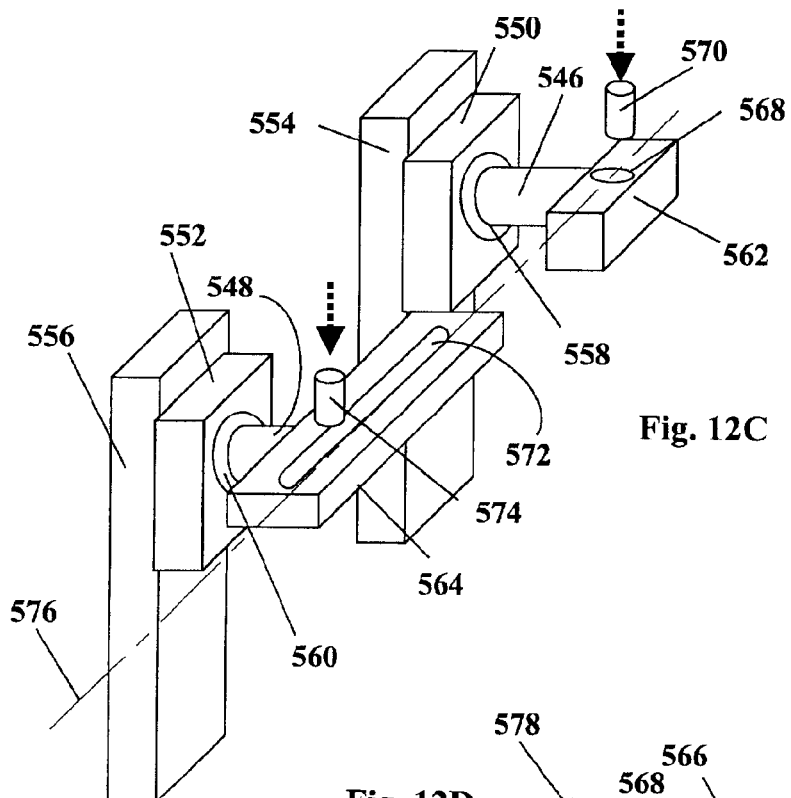
Fig. 12C
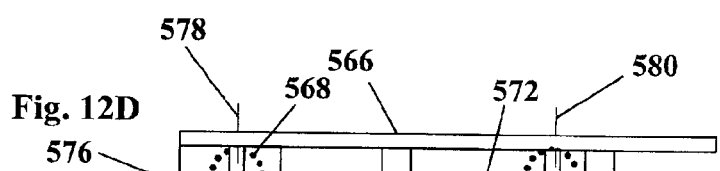
Fig. 12D
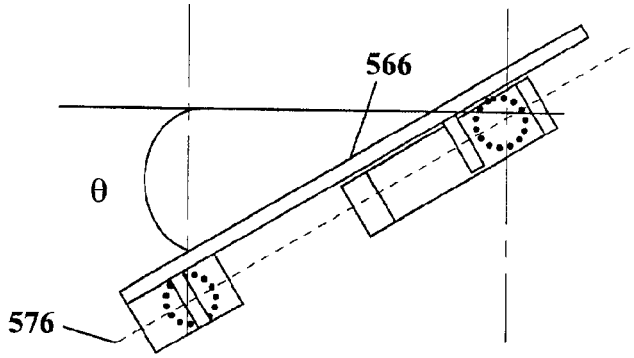
Fig. 12E
Fig. 12F

SYSTEM FOR MRI-GUIDED INTERVENTIONAL MAMMARY PROCEDURES

CLAIM OF PRIORITY

This application is a divisional of U.S. patent application Ser. No. 09/407,346, filed Sep. 29, 1999, now U.S. Pat. No. 6,675,037, herein incorporated by reference.

GOVERNMENT FUNDING

The invention described herein was made with Government support by the National Institute of Health (NIH) under grant number R41CA81817 (National Cancer Institute). The United States Government has certain rights in the invention.

BACKGROUND OF THE INVENTION

1. Field of the Invention

The present invention relates to Magnetic Resonance Imaging-Guided (MRI-Guided) medical procedures, particularly MRI-Guided interventional procedures and therapies that are performed on the breasts or mammaries of patients.

2. Background of the Art

The diagnosis and treatment of breast cancer is a major health care issue which affects the lives of more than 180,000 women annually, only considering the United States. While, early detection and treatment of breast cancer is a major factor for efficient patient management, there is significant technical space available for developing a highly efficient approach for diagnosing and characterizing breast cancer. Although numerous studies manifest an almost 100% sensitivity of MRI for the detection of breast cancer, the studies also demonstrate a widely varying specificity. These findings result in a patient management dilemma when lesions are detected with MRI and those lesions have not been seen with other gold standard modalities. MRI-Guided biopsy or MRI-Guided wire localization therefore will be important in integrating MRI into breast cancer management. Furthermore, it is reasonable to suggest that the combination of MRI diagnostic imaging, for example contrast agent perfusion, with MRI guided subcutaneous core biopsy may provide an improved method for the detection and characterization of breast cancer. In addition, breast conserving therapies (BCT), such as laser photoablation therapy, are under evaluation. These approaches require accurate positioning and monitoring of their effect (e.g. tissue temperature) during insertion and during the actual procedure. Visualization can be achieved in real-time with MRI systems. Thus an apparatus to position interventional devices and monitor their operation under MRI guidance would be likely to improve the success of diagnostic and therapeutic procedures.

Several MR-guided free-hand or stereotaxic apparatus have been implemented for interventions of the breast, such as preoperative localization, fine needle aspiration biopsy and core biopsy (U. Fischer, et al., "MR Imaging-Guided Biopsy Breast Intervention: Experience with Two Systems" *Radiology* 192, 876–881, (1994); U. Fischer, et al., "MR-Guided Biopsy of Suspected Breast lesions with a Simple Stereotaxic Add-On Device for Surface Coils" *Radiology* 200, 651–658 (1996)), (C. K. Cuhl, et al., "Interventional Breast MR Imaging: Clinical Use of a Stereotaxic Localization and Biopsy Device" *Radiology* 204, 667–675 (1997); S. H. Heywang-Kobrunmner, et al., "Prototype Breast Coil for MR-Guided needle Localization" *J. Comp. Assist. Tomogr.* 18, 876–881 (1994)) and (S. Greenstein-Orel, et al., "MR Imaging-Guided Localization and Biopsy of Breast Lesions: initial Experience" *Radiology*, 193, 97–102 (1994); E. K. Insko, et al., "Multicoil Array for High Resolution Imaging of the Breast" *Magn. Reson. Med.* 37, 778–784 (1997)). The design and the operation of these devices are tailored for use inside the limited space of an MRI scanner, and a short contrast window (5 to 10 min). Such studies have demonstrated the feasibility of combining MRI, as a diagnostic modality, with MR-guided interventions of the breast. The common features of such devices are: (a) compression of the breast for better fixation, with one or two plates and (b) use of an arrangement of puncture channel (mesh) to correctly place the interventional probe. Despite their success, there are some limitations in these designs, particularly when they are compared with the non-MR stereotaxic devices. First, most of the devices provide compression along a specific orientation, usually medial-lateral, which may not be the optimal one, as for example for transversing the shortest path in the tissue or to reach areas such as the axilla. Second, in most of the devices the probe is directed by means of a mesh, and thus it can be only inserted perpendicular to the compression plates or with a slight "free-hand" angulation. This may not be the optimal approach, for example, when attempting to access tissue close to the chest wall, at the axilla or to avoid obstructions such as implants. The two single plate systems have the same limitations and in addition there is the potential for accidental rib puncture or highly invasive operations behind the nipples. The operation of the above devices requires the patient to be removed from the magnet, the probe inserted and then re-imaged, with the possibility that another insertion may be required to correct the initial one. This practice increases the length of the operation, and may not be always feasible due to the limited number of allowed injections of contrast material and the short duration of the contrast window.

Several types of interventional devices, including such devices as catheters, ultrasonic devices, transcanular devices, excavating tools, therapeutic tools (e.g., lasers, cryoablation, drug delivery, electrical stimulating devices, etc.) have been used in MRI-Guided procedures in the breast including within them MRI compatible features such as such as non-specific surface RF coils (U. Fischer, et al., "MR Imaging-Guided Biopsy Breast Intervention: Experience with Two Systems" *Radiology* 192, 876–881, (1994); U. Fischer, et al., "MR-Guided Biopsy of Suspected Breast lesions with a Simple Stereotaxic Add-On Device for Surface Coils" *Radiology* 200, 651–658 (1996)), modified RF coils (C. K. Cuhl, et al., "Interventional Breast MR Imaging: Clinical Use of a Stereotaxic Localization and Biopsy Device" *Radiology* 204, 667–675 (1997); S. H. Heywang-Kobrunner, et al., "Prototype Breast Coil for MR-Guided needle Localization" *J. Comp. Assist. Tomogr.* 18, 876–881 (1994)) and a multi-coil array (S. Greenstein-Orel, et al., "MR Imaging-Guided Localization and Biopsy of Breast Lesions: initial Experience" *Radiology,* 193, 97–102 (1994); E. K. Insko, et al., "Multicoil Array for High Resolution Imaging of the Breast" *Magn. Reson. Med.* 37, 778–784 (1997)). These RF coils, except for those shown in Greenstein-Orel, et al. and E. K. Insko, et al., are of standard dimensions and are not appropriate for use with the proposed apparatus since they will have a variable filling-factor for different degrees of breast compression. To address these issues, and others analyzed herein, different methodologies are needed in the field.

While endoscopic, arthroscopic, and endovascular therapies have already produced significant advances in health care, these techniques ultimately suffer from the same limitation. This limitation is that the accuracy of the procedure is "surface limited" by what the surgeon can either see through the device itself or otherwise visualize (as by optical fibers) during the course of the procedure. That is, the visually observable field of operation is quite small and limited to those surfaces (especially external surfaces of biological masses such as organs and other tissue) observable by visible radiation, due to the optical limitations of the viewing mechanism. MR imaging, by comparison, overcomes this limitation by enabling the physician or surgeon to non-invasively visualize tissue planes and structures (either in these planes or passing through them) beyond the surface of the tissue under direct evaluation. Moreover, MR imaging enables differentiation of normal from abnormal tissues, and it can display critical structures such as blood vessels in three dimensions. Prototype high-speed MR imagers which permit continuous real-time visualization of tissues during surgical and endovascular procedures have already been developed. MR-guided minimally invasive therapy is expected to substantially lower patient morbidity because of reduced post-procedure complications and pain. The use of this type of procedure will translate into shorter hospital stays, a reduced convalescence period before return to normal activities, and a generally higher quality of life for patients. The medical benefits and health care cost savings are likely to be very substantial.

New technologies like intra-operative magnetic resonance imaging and nonlinear magnetic stereotaxis, the latter discussed by G. T. Gillies, R. C. Ritter, W. C. Broaddus, M. S. Grady, M. A. Howard III, and R. G. McNeil, "Magnetic Manipulation Instrumentation for Medical Physics Research," *Review of Scientific Instruments*, Vol. 65, No.3, pp.533–562 (March 1994), as two examples, will likely play increasingly important roles here. In the former case, one type of MR unit is arranged in a "double-donut" configuration, in which the imaging coil is split axially into two components. Imaging studies of the patient are performed with this system while the surgeon is present in the axial gap and carrying out procedures on the patient. A second type of high-speed MR imaging system combines high-resolution MR imaging with conventional X-ray fluoroscopy and digital subtraction angiography (DSA) capability in a single hybrid unit. These new generations of MR scanners are able to provide the clinician with frequently updated images of the anatomical structures of interest, therefore making it possible to tailor a given interventional procedure to sudden or acute changes in either the anatomical or physiological properties of, e.g., a part of the brain into which a drug agent is being infused.

Nonlinear magnetic stereotaxis is the image-based magnetically guided movement of a small object directly through the bulk brain tissues or along tracts within the neurovasculature or elsewhere within the body. Electromagnets are used to magnetically steer the implant, giving (for example) the neurosurgeon or interventional neuroradiologist the ability to guide the object along a particular path of interest. (The implant might be either magnetically and/or mechanically advanced towards its target, but is magnetically steered, in either case. That is, magnetic fields and gradients are used to provide torques and linear forces to orient or shift the position of the implant or device, with a mechanical pushing force subsequently providing none, some, or all of the force that actually propels the implant or device. Additional force may be provided magnetically.) The implant's position is monitored by bi-planar fluoroscopy, and its location is indicated on a computerized atlas of brain images derived from a pre-operative MR scan. Among other applications, the implant might be used to tow a pliable catheter or other drug delivery device to a selected intracranial location through the brain parenchyma or via the neurovasculature. Magnetic manipulation of catheters and other probes is well documented in research literature. For example, Cares et al. (J. Neurosurg, 38:145, 1973) have described a magnetically guided microballoon released by RF induction heating, which was used to occlude experimental intracranial aneurysms. More recently, Kusunoki et al. (Neuroradiol 24: 127, 1982) described a magnetically controlled catheter with cranial balloon useful in treating experimental canine aneurysms. Ram and Meyer (*Cathet. Cardiovas. Diag.* 22:317, 1991) have described a permanent magnet-tipped polyurethane angiography catheter useful in cardiac interventions, in particular intraventricular catheterization in neonates.

U.S. Pat. No. 4,869,247 teaches the general method of intra parenchymal and other types of magnetic manipulation, and U.S. Pat. Nos. 5,125,888; 5,707,335; and 5,779,694 describe the use of nonlinear magnetic stereotaxis to maneuver a drug or other therapy delivery catheter system within the brain. U.S. Pat. No. 5,654,864 teaches a general method of controlling the operation of the multiple coils of a magnetic stereotaxis system for the purpose of maneuvering an implant to precisely specified locations within the body. Both of these technologies offer a capability for performing image-guided placement of a catheter or other drug delivery device, thus allowing drug delivery directly into the brain via infusion through the walls of the catheter or out flow of the tip off the catheter. In the case of drug delivery directly into the brain tissues, the screening of large molecular weight substances by the endothelial blood-brain barrier can be overcome. In the case of infusions into specific parts of the cerebrovasculature, highly selective catheterizations can be enabled by these techniques. In either case, however, detailed visual images denoting the actual position of the drug delivery device within the brain would be extremely useful to the clinician in maximizing the safety and efficacy of the procedure. The availability of an MR-visible drug delivery device combined with MR-visible drug agents would make it possible to obtain near real-time information on drug delivery during interventional procedures guided by non-linear magnetic stereotaxis. Drug delivery devices, such as catheters, that are both MR-visible and radio-opaque could be monitored by two modalities of imaging, thus making intra-operative verification of catheter location possible during nonlinear magnetic stereotaxis procedures. (Intra-operative MR assessment might require the temporary removal of the magnetic tip of the drug delivery catheter and interruption of the magnetic stereotaxis procedure to image the patient.).

In the treatment of all diseases, and especially neurological diseases and disorders, targeted drug delivery can significantly improve therapeutic efficacy, while minimizing systemic side-effects of the drug therapy. Image-guided placement of the tip of a drug delivery catheter directly into specific regions of the brain can initially produce maximal drug concentration close to some targeted loci of tissue receptors following delivery of the drug. At the same time, the limited distribution of drug injected from a single catheter tip presents other problems. For example, the volume flow rate of drug delivery must be very low to avoid indiscriminate hydrodynamic damage or other damage to brain cells and nerve fibers. Delivery of a drug from a single point source may also limit the distribution of the drug by decreasing the effective radius of penetration of the drug agent into the surrounding tissue receptor population. Positive pressure infusion, i.e., convection-enhanced delivery of drugs into the brain, as taught by U.S. Pat. No. 5,720,720 may overcome the problem of effective radius of penetration. Also, U.S. patent application Ser. No. 08/857,043, filed on May 15, 1997 and titled "Method and Apparatus for Use with MR Imaging" describes a technology comprising a method for observing the delivery of material to tissue in a living patient comprising the steps of a) observing by magnetic resonance imaging a visible image within an area or volume comprising tissue of said living patient, the area or volume including a material delivery device, b) delivering at least some material by the material delivery device into the area or volume comprising tissue of a living patient, and c) observing a change in property of said visible image of the area or volume comprising tissue of a living patient while said material delivery device is still present within the area or volume. This process, including the MRI visualization, is performed in approximately or actually real time, with the clinical procedure being guided by the MRI visualization.

U.S. Pat. Nos. 4,869,247, 5,654,864, 5,125,888, 5,707,335 and 5,779,694 describe processes and apparatus for the use of magnetic stereotaxis for the manipulation of an object or implant which is moved into position within a patient, particularly within the cranial region and specifically within the brain but in principle elsewhere in the body also.

Research on magnetic catheterization of cerebral blood vessels generally has focused on design of transvascular devices to thrombose aneurysms, to deliver cytotaxic drugs to tumors, and to deliver other therapies without the risks of major invasive surgery. Examples of such studies include Hilal et al (*J. Appl. Phys.* 40:1046, 1969), Molcho et al (*IEEE Trans. Biomed. Eng. BME* 17, 134, 1970), Penn et al (J. Neurosurg. 38:239, 1973), and Hilal et al (*Radiology* 113:529,1974). U.S. Pat. Nos. 4,869,247, 5,654,864, 5,125,888, 5,707,335 and 5,779,694 describe processes and apparatus for the use of magnetic stereotaxis for the manipulation of an object or implant which is moved into position within a patient, particularly within the cranial region and specifically within the brain but in principle elsewhere in the body also. These patents do no not involve any contemplation of real time visualization of drug distribution within the brain, especially by MRI. It should be noted that the potential exists for interactive interference between the two systems, magnetic resonance imaging and magnetic stereotaxis, particularly where fine images are being provided by a system based on magnetic coils, especially as described in U.S. patent application Ser. No. 08/916,596, filed on Aug. 22, 1997, which is incorporated herein by reference for its disclosure of the design, construction, structure and operation of coils and catheters in MR-guided procedures.

One recently established method of reading the data obtained from the MR imaging is technically founded upon existing knowledge of Apparent Diffusion Coefficients (ADC) in particular regions of the body. There is significant published literature with respect to ADC values for specific tissues in various parts of animals, including various tissues of humans (e.g., Joseph V. Hajnal, Mark Doran, et al., "MR Imaging of Anisotropically Restricted Diffusion of Water in the Nervous System: Technical, Anatomic, and Pathological Considerations," *Journal of Computer Assisted Tomography*, 15(1): 1–18, January/February, 1991, pp. 1–18). It is also well established in the literature that loss of tissue structure through disease results in a decrease of the ADC, as the tissue becomes more like a homogeneous suspension. Clinical observations of changes in diffusion behavior have been made in various tissue cancers, multiple sclerosis, in strokes (where the reduction in diffusion precedes the increase in T2), and in epilepsy. (e.g., Y. Hasegawa, L. Latour, et al. "Temperature Dependent Change of Apparent Diffusion Coefficient of Water in Normal Ischemic Brain", *Journal of Cerebral Blood Flow and Metabolism* 14:389–390, 1994).Thus, ADC values are specific for specific types of tissues. Accordingly, as different drugs/chemicals are introduced into a tissue volume under MR observation, the change in ADC resulting from each drug/chemical interaction with the ambient water proton environment can be observed.

While the ADC is the preferred means within the present invention of mapping the delivery of drug in tissue, other embodiments of the invention allow for additional tissue contrast parameters to track the delivery of a drug into tissue. In other words, the delivery of a drug into tissue will cause other MRI-observable changes which can be mapped (as is done for ADC) and which can be used to map the spatial distribution characteristics of the drug within and around the targeted tissue. While some of these observations may be larger in magnitude than others, any of the MRI contrast mechanisms' effects can be used as a tracking mechanism to longitudinally evaluate the spatial kinetics of drug movement within the imaging volume.

The tissue contrast changes apparent on an MR image can arise from ADC, from alterations in the BO magnetic field (often referred to as magnetic susceptibility or ABO produced by the presence of a substance in said tissue), from alterations in local tissue T1 relaxation times, from local T2 relaxation times, from T2* relaxation times (which can be created by susceptibility differences), from the magnetization transfer coefficients (MTC is an effect produced by local communication between free water protons and those of nearby macromolecular structures), from the ADC anisotropy observed in oriented matter, and also from local differences in temperature which will affect in varying degrees all of the included tissue contrast parameters. In addition, the delivery of drug can also be tracked from magnetic field frequency shifts caused by the drug or arising from agents (e.g., MR taggants) added with unique frequency shifts from those of the local protons (such as that created from F-19 or fluorine-19 agents found in or added to the drug).

MR imaging of the alterations in the BO magnetic field (also known as imaging of the local magnetic susceptibility) can reveal the spatial distribution of a drug from the interaction of the drug with the otherwise homogeneous magnetic field found in MRI. To enhance the alterations in the magnetic field BO caused by the drug, small amounts of a BO-altering added agent or agents can be added to the drug during delivery. This can include iron oxide particles, or other materials, such as those comprising lanthanide-, manganese-, and iron-chelates. In addition, vehicles containing differing gases ($N_2$, $O_2$, $CO_2$) will also alter the local magnetic field and thus produce a magnetic susceptibility effect which can be imaged.

Targeted delivery of drug agents may be performed by any therapeutically effective drug delivery device or system, including, for example, those utilizing MR-compatible pumps connected to variable-length concentric MR-visible dialysis probes each with a variable molecular weight cut-off membrane, or by another MR-compatible infusion device which injects or infuses a diagnostic or therapeutic drug solution. Imaging of the injected or infused drug agent is performed by MR diffusion mapping using the RF microcoils attached to the distal shaft of the injection device, or by imaging an MR-visible contrast agent that is injected or infused through the walls of the dialysis fiber into the brain. The delivery and distribution kinetics of injections or infusions of drug agents at rates, for example, of between 1 ml/min (or less) to 1000 ml/min (or more) are monitored quantitatively and non-invasively using real-time contrast-enhanced magnetic susceptibility MR imaging combined with water proton directional diffusion MR imaging.

Non-invasive examination procedures for the mammaries have proven to be of significant early diagnostic benefit. However, there is significant pain and discomfort involved in the present procedures that causes many patients to resist regular and early examination. MRI guided interventional procedures for mammary examinations require their own unique procedures to be acceptable to the patients.

SUMMARY OF THE INVENTION

The combination of contrast enhanced magnetic resonance imaging (MRI) and MR-guided subcutaneous core biopsy can be used as a robust approach for the diagnosis and treatment of breast cancer. MRI provides the means to accurately position and monitor interventional procedures such as biopsy, removal of tissue or other transcanular procedures. MRI may also be used in this invention to position and monitor the progress of breast conserving therapies (BCT), such as laser photo-ablation, cryoablation and localized hyperthermia. The general practice of this invention is to provide a remotely controlled apparatus for MR-guided interventional procedures in the breast. The apparatus allows the practice of a method that provides flexibility in conditioning the breast, i.e. orientation and degree of compression, and in setting the trajectory of the intervention.

To that end, a robust conditioning/positioning device, fitted with the appropriate degrees of freedom, enhances the efficacy and efficiency of breast interventions by providing the flexibility in planning and executing an appropriate procedure strategy that better suits interventional procedures, either those in current use or yet to be developed. The novelty and potential commercial success of the device originates from its high maneuverability to set and perform the procedure strategy and its adaptability to accommodate an array of interventional probes. Remote control of this device can allow planning the operation and performing the relevant tasks in a short period, for example, within the contrast window provided by a single injection of a contrast agent, and this feature can be operator-independent.

A remotely controlled device may be used that provides high accessibility to the target in the breast and a single step set-up of the procedures. The device may be equipped with a quadrature or linear RF coil with variable width. The remotely controlled device may allow for high flexibility in conditioning the breast and accessing a target inside a breast that better suits the interventional procedure, with the following features optimally used. For example the controller could benefit from: a) Operator-defined orientation and degree of compression and trajectory, i.e. orientation of probe insertion, for optimized access to any area in the breast and, in particular, for difficult-to-reach areas. b) A remote control mechanism of mechanical or hydraulic actuators and MR-visible markers for verifying and monitoring the execution of the planned operation with an MRI scanner. c) Suitable software for planning the intervention and operating the device. d) A generic instrumentation platform which can accommodate a variety of probes and accessories.

e) Suitable degrees of freedom to accomplish the aforementioned task, and in particular its ability to position the intervention probes at any spatial position with given spatial limitations, as imposed by the wide variety of breast and chest anatomies and lesion positions that may be presented. f) The accuracy and repeatability to position the interventional probes at given spatial locations. g) Its compatibility for operation inside an MRI scanner. h) A suitable radio frequency (RF) coil such as a quadrature biplanar RF coil with adjustable spatial separation of the two planar elements to conform with the shape alterations of the compressed breast. The remotely controlled device may be moved by any convenient means. For example, there may be direct manual control, dials maneuvering the device through a mechanical interface, or computer driven controls that drive the device.

The general methodology of practice of the process in the present invention under MRI guidance comprises injecting a contrast agent into the patient at a position of injection that will enable the contrast agent to spread within tissues of the breast; allowing the contrast agent to spread into the tissues of the breast to reach at least a predetermined level of contrast; then condition the breast to restrict the flow of blood into and out of the breast to increase the persistence of the contrast agent within the breast. When that initial preparation of the area of the breast to be imaged has been performed, an operator may observe the breast under non-invasive procedures that use or require the use of contrast agents in the observational procedure. Then an interventional procedure may be used or performed under the observational technique while the contrast agent persists in the area of concern. This contrast persisting technique can increase the time that the procedure may be performed under adequate observational conditions, while minimizing the amount and number of times that contrast agent needs to be provided or injected.

This procedure increases the time under which the procedure may be performed, requires fewer and lower quantitative doses of contrast agent, requires fewer manipulations of the breast tissue while physically restricted, and generally makes non-interventional breast observation more tolerable to the patient.

DETAILED DESCRIPTION OF THE INVENTION

Figure 1:
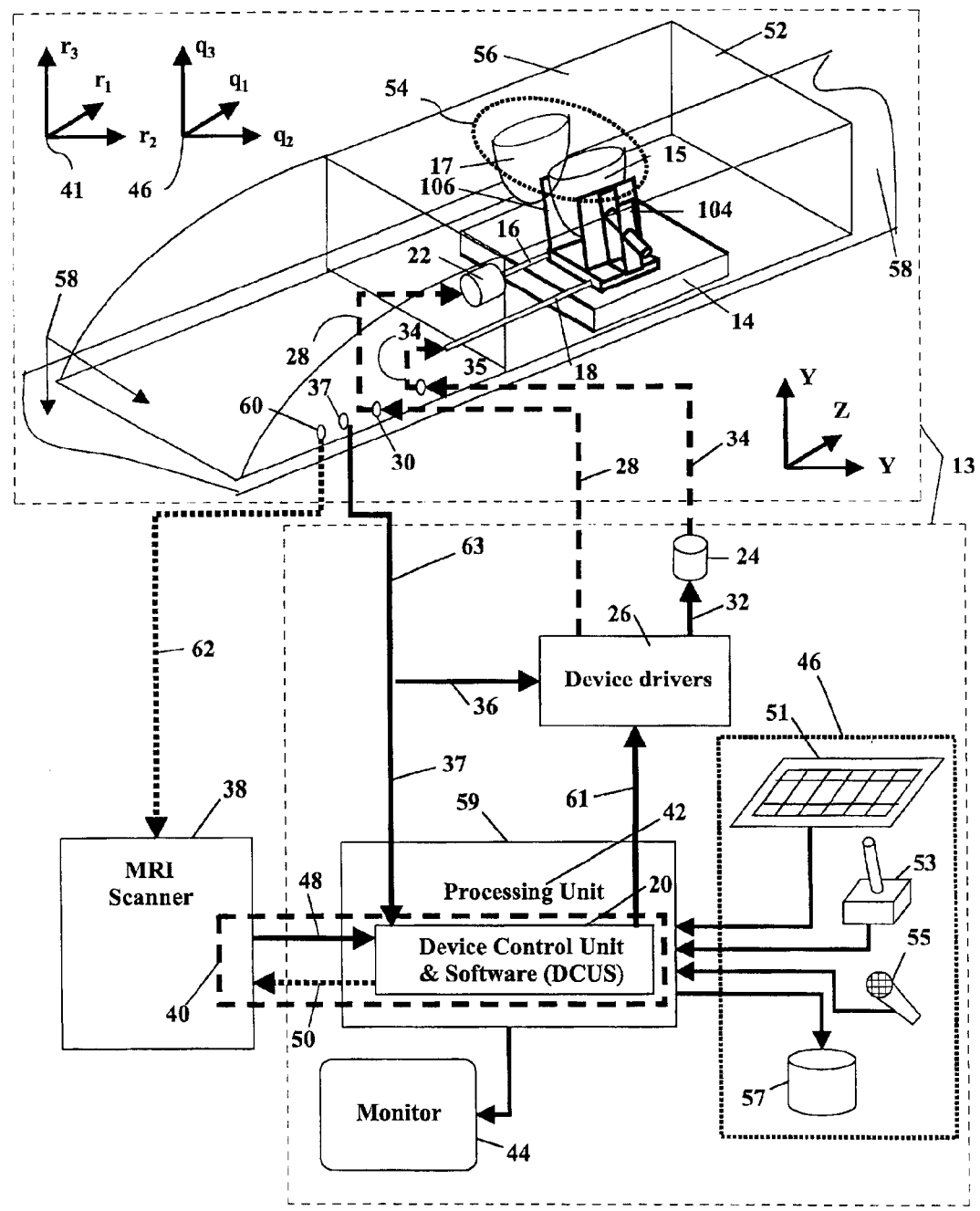
FIG. 1 shows a conceptual illustration of an interventional system.

The general methodology of practice of the process in the present invention comprises injecting a contrast agent into the patient at a position of injection that will enable the contrast agent to spread within tissues of the breast; allowing the contrast agent to spread into the tissues of the breast to reach at least a predetermined level of contrast; then condition the breast to restrict the flow of blood into and out of the breast to increase the persistence of the contrast agent within the breast. When that initial preparation of the area of the breast to be imaged has been performed, an operator may observe the breast under non-invasive procedures that use or require the use of contrast agents in the observational procedure. Then an interventional procedure may be used or performed under the observational technique while the contrast agent persists in the area of concern. This contrast persisting technique can increase the time that the procedure may be performed under adequate observational conditions, while minimizing the amount and number of times that contrast agent needs to be provided or injected.

A method and apparatus are described for use in an invasive procedure on a breast of a patient. The method may comprise, for example:

A method for an MRI guided invasive procedure on a breast of a patient comprising:

a) positioning a breast of a patient between at least two non-magnetically susceptible supports; (optionally then rotating at least one of the at least two supports relative to the breasts, i.e., perpendicular to the body or otherwise around an axis, e.g., a vertical axis).

b) applying pressure to the breast with said at least two supports; (optionally positioning a universal probe stage [e.g., with two dimensional motion] at an appropriate position onto the surface of one of the supports; then possibly rotating the probe stage to an axis preferably parallel to the plane of the support; setting the depth of the probe; these steps may be repeated to achieve the desired interventional path for the interventional device based on MR images collected either in real time or periodically, or before and after any of these steps)

c) examining the breast with MRI may have been and continues to be performed continuously or in discrete stages; and d) inserting and guiding an invasive medical implement into said breast with constant MRI visualization of the inserting and guiding of the invasive medical implement.

During this method, while examining said breast with MRI, at least one of the at least two supports may be repositioned. While examining said breast with MRI, at least one of the at least two supports may repositioned by mechanical means. While examining the breast with MRI, at least one of the at least two supports may be repositioned by mechanical means that are operator remote controlled. While examining the breast with MRI, at least one of the at least two supports may be repositioned by mechanical means to alter the relative position of tissue within the breast, not merely repositioning available entrance routes for any invasive medical devices. The at least two supports may be positioned so that a path between the at least two supports allows a linear path into the breast that is not necessarily perpendicular to a line parallel with a spine of the patient. That linear path may be, for example, at an angle of between 0 and 60 degrees to the spine of the patient. The preferred medical implement have MR visible markers thereon. The method of controlling the device may be practiced either by manual operation or computer controlled operation, mechanical and/or hydraulic means. That preferred medical implement may comprise RF coils on a substrate, such as a catheter. The method may be practiced where a computer stores a program and the program calculates step-motor instructions and controls at least one motion drivers controlling motion of the invasive medical implement. The computer may store a program and the program forwards data indicating a visualization of position of the implement within the breast in real time. The at least two supports may be fastened together to resist relative movement between the at least two supports and repositioning is effected by temporarily unfastening or loosening the two supports, repositioning at least one of the supports, and then refastening the at least two supports.

Figure 11:
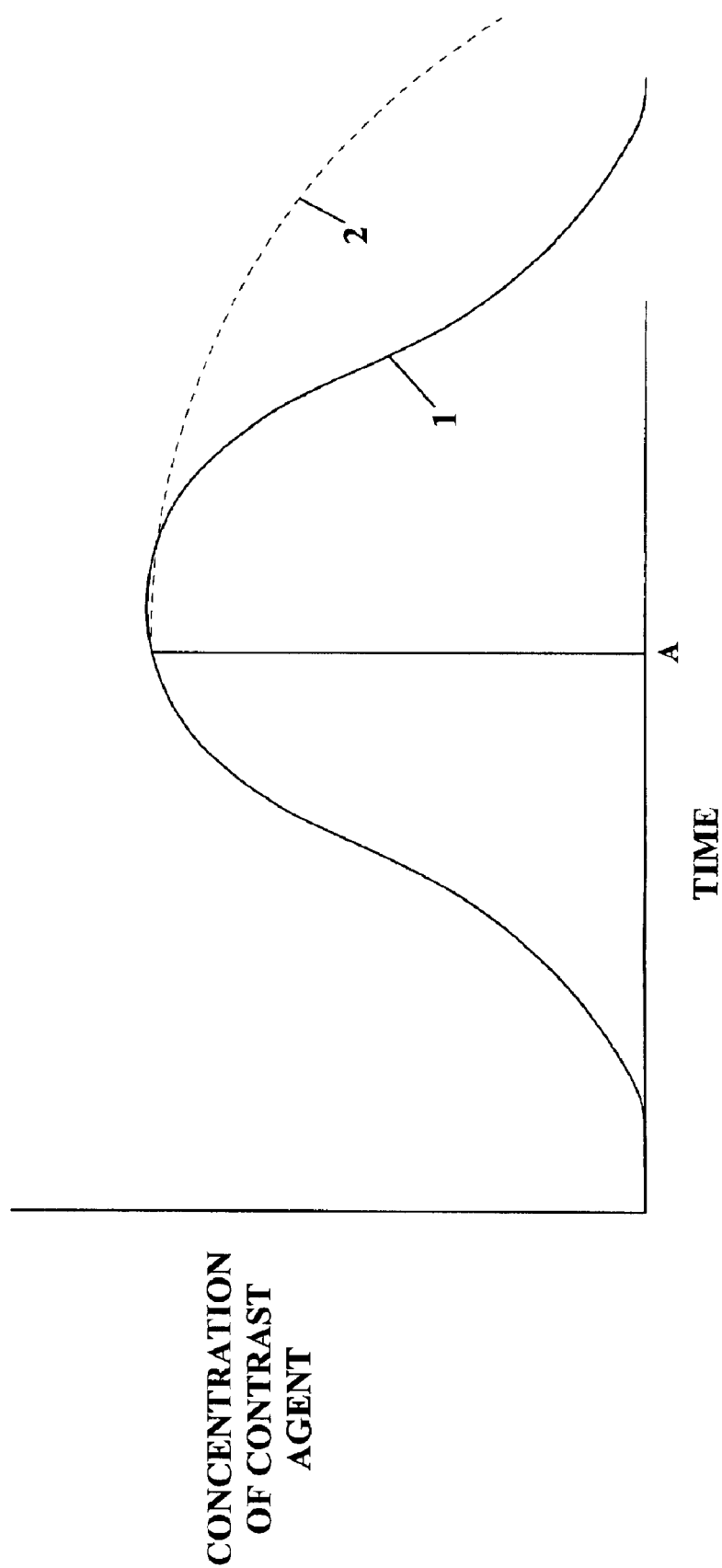
FIG. 11 shows a graphic representation of the Concentration of Contrast Agent versus Time.

Furthermore the remote control of the device may provide the ability to manipulate the features of the contrast enhancement of the target area in the breast, secondary to infusion of the contrast material. The contrast enhancing features (such as the peak enhancement and the duration of the enhancement time window during the 'wash-out' phase of the contrast agent) may be prolonged if compression of the breast by the proposed device obstructs or limits the clearance rate of the contrast material out of the breast. Note in FIG. 11 the two different curves representing the concentration of contrast agent versus time. In the first curvem where no eternal pressure is applied, there is a rise to maximum concentration and then a more rapid decrease in concentration as compared to the second curve where pressure has been applied at time A, to maximize the time over which a useful concentration of contrast agent would remain in the target area. A method for an invasive procedure on a breast of a patient may also be generally described as comprising:

positioning a breast of a patient between at least two non-magnetically susceptible supports;

injecting the patient with a contrast agent so that the concentration of the contrast agent within the breast will increase to a maximum concentration for a period of time after injection;

before the concentration of the contrast agent reaches the maximum concentration, applying pressure to the breast to restrict blood flow within the breast;

maintaining the pressure on the breast to reduce the rate of flow of contrast agent out of the breast; and examining tissue by a non-invasive procedure of the breast which examining procedure is enhanced by the use of the contrast agent while the rate of blood flow is restricted.

An invasive procedure on the breast may be performed under examination by the non-invasive procedure. After the maximum concentration of contrast agent has occurred and after concentration of the contrast agent has decreased, the pressure on the breast can be released, reinjecting the patient with contrast agent, allowing the concentration of contrast agent to increase to a concentration less then the maximum concentration that will occur from the injection, and before the maximum concentration has occurred, applying pressure to the breast to restrict the flow of blood within the breast. The device for performing the invasive procedure may be supported on a moveable support near one of the at least two non-magnetically susceptible supports, and the device is moved relative to one of the at least two non-magnetically susceptible supports to position the device for performing invasive surgery on the breast. The device may be moveable in one, two or three dimensions for position the device relative to the at least two non-magnetically susceptible supports. At least one of the supports for the breast may have a window or holes to allow insertion of an interventional probe. Such a window may be covered by a sheet, e.g., a transparent polymeric sheet, such as made of Mylar, to assist in supporting the breast. The material of this sheet should be penetrable by an interventional probe. At least one of the supports has holes therein and an invasive medical device may inserted through a window or hole and into the breast. A series of holes may be provided in the plate support, so that the holes may be serendipitously located near the target tissue and/or the breast and plates moved according to the teachings of the invention to better position the target tissue or the hole. The method may have the invasive medical device inserted through said hole or window and into said breast during real-time examining under visualization by the non-invasive procedure. The non-invasive procedure preferably comprises magnetic resonance imaging.

An alternative way of describing aspects of this method include:

a) positioning a breast of a patient between at least two non-magnetically susceptible supports;

b) applying pressure to the breast with the at least two supports;

c) examining the breast with MRI; and d) inserting and guiding a medical implement into the breast with constant MRI visualization of the inserting and guiding. While examining said breast with MRI, at least one of said at least two supports may be repositioned. While examining said breast with MRI, at least one of said at least two supports may repositioned by mechanical means, the repositioning accomplished, for example by remote control of the motivating element of the repositioning system. The method may allow, while examining said breast with MRI, at least one of said at least two supports to be repositioned by mechanical means to alter the relative position of tissue within said breast, either improving a field of view or assisting in improving interventional access to the tissue of interest in the MR field. For example, the at least two supports may be positioned so that a path between said at least two supports allows a linear path into said breast that is not perpendicular to a line parallel with a spine of the patient, towards the patient's heart, or toward scar tissue within the field of view. With that type of procedure, the linear path is at an angle of between 0 and 180 degrees to the spine of the patient, or may be angled by at least 5 degrees or at least 10 degrees away from the tissue that is to be particularly avoided by the interventional procedure. The medical implement may have MR visible markers thereon, may comprise RF coils on a substrate or a catheter.

The system may comprise a computer that stores a program and the program calculates step-motor instructions and controls at least one motion drivers controlling motion of said implement, or stores a program and said program forwards data indicating a visualization of position of said implement within said breast in real time.

The method and apparatus may include the at least two supports are fastened together to resist relative movement between the at least two supports and repositioning is effected by temporarily unfastening or loosening the two supports, repositioning at least one of the supports, and then refastening the at least two supports. Fastening may be by mechanical or other means, such as hook and loop fasteners (e.g., Velcro). Snaps, toggles, dog ears, stitching, adhesive securement, and other known securement means.

Several engineering and methodological innovations are particularly associated with this invention: (a) high flexibility for the definition of the trajectory of insertion of the interventional probe, (b) flexibility for the definition of the orientation and degree of breast compression, (c) a design of hydraulic actuators suitable for the limited space inside an MRI scanner (d) an approach to verify the accuracy of positioning by means of MRI visible markers, (e) a biplanar RF coil with variable spatial separation. In addition, it is expected that the proposed apparatus will provide new knowledge and experience to the field of MRI guided interventions and therapies.

A further understanding and appreciation of the invention may be obtained by consideration of the non-limiting figures.

The system 13 is comprised by three main components: a positioning device (PD) 14 to position an interventional probe, appropriate assembly of computer controlled motion actuators 16 or 18 to control the PD and a device control unit and software (DCUS) module 20. The PD 14 is situated inside a MRI scanner and is positioned preferentially underneath the patient. According to the invention, the PD has two compression plates 104 and 106 so to compress one of the breasts, say breast 15. The PD 14 is controlled via the DCUS 20 to position an interventional probe, chosen by the operator, at a particular trajectory set by the operator with a predetermined orientation and degree of compression, as described herein. The interventional probe can be, for example, a biopsy needle or wire, or a device for transcanula operations. Such probes can be used for either diagnostic, for example a tissue sampling instrument, or therapeutic, for example a laser probe, purposes. Furthermore, the device can be used to position any instrumentation with MR guidance relative to a target in the breast. Such instrument can be, for example an ultrasound source used for localized hyperthermia with real-time MRI guidance by means for mapping the spatial distribution of tissue temperature.

The motion actuators are driven by energy-to-motion (E-M) transducers, which can be located either on the device, for example 22, or at a distance, for example transducer 24. E-M transducers, which operation is not affected by static or the switching magnetic fields of the MR scanner, for example ultrasonic motors that are based on the piezoelectric phenomenon, and hydraulic units, based on the alterations of hydraulic pressure, can be placed on the device, say a generic 22. E-M transducers, which operation can be affected by the static or the switching magnetic fields of the MR scanner, for example electromagnetic motors, can be placed away from the device, say position 24.

Furthermore, the system may include secondary components to facilitate the control of the transducers, for example, motion controllers, power drives and associated software 26. In the case that the energy-to-motion transducers are located on the device, then there is a power link 28 between the motion controller 26 and the transducer 22. A port may be provided to facilitate easy installation of the system. In the case that the energy-to-motion transducers are located away from the device, then there is a power link 32 between the motion controller 26 and the transducer 24 and a mechanical link 34 between the transducer 24 and the motion actuator 18. For example, a mechanical link 34 can be a flexible drive shaft connecting a standard stepper motor as transducer 24 with a corresponding actuator. Accordingly for a hydraulic system, the link is a hydraulic line. A port appropriate for the particular type of E-M transducer to motion actuator link may provided to facilitate easy installation of the system. The components 22, 24, 26 may be selected according to the available components in the market. These secondary components may or may not be part of this invention.

According to another aspect of the invention, a hybrid system can be constructed with different degrees of freedom controlled by different actuator/transducer combinations.

Furthermore, the invention includes in its description an appropriate RF coil suitable for monitoring the proposed device, which can be, for example, an existing body RF coil, standard in most of the conventional MRI scanners. The secondary components and RF coil need not be part of this invention, which is focused in the PD 14 (FIGS. 1; 3–10), the DCUS 18 (FIGS. 1, 11, 12) the method of delivering an intervention (FIG. 2) and method of operation (FIGS. 13 to 14).

Figure 2A:
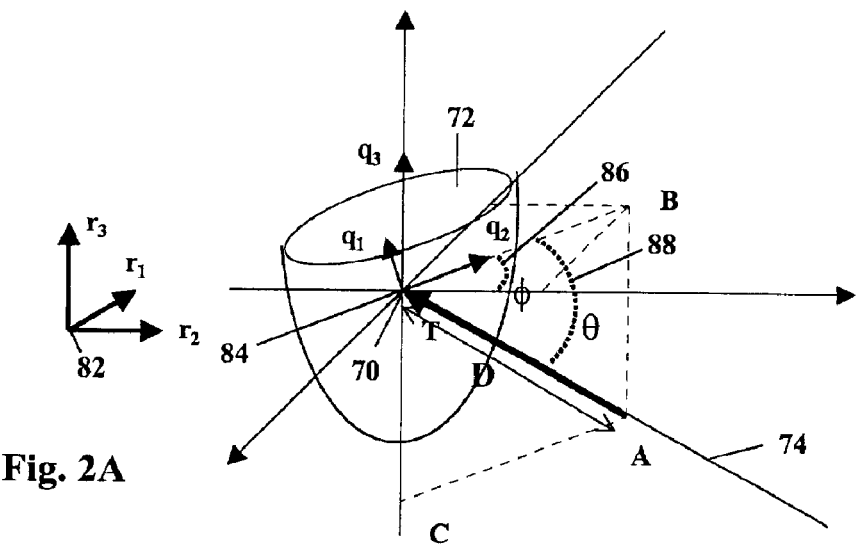
FIGS. 2A, 2B and 2C are a representative illustration of the method of operation of a device according to the invention.
Figure 2B:
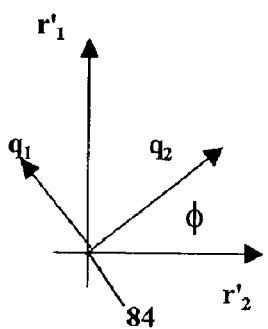
Figure 2C:
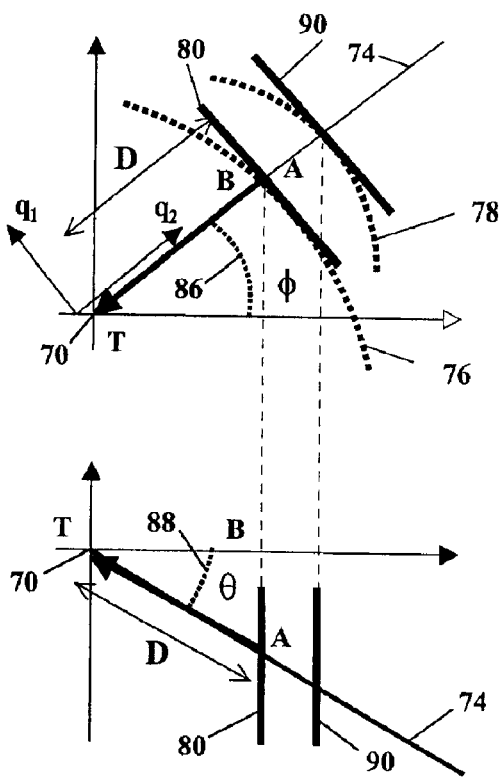
Figure 13:
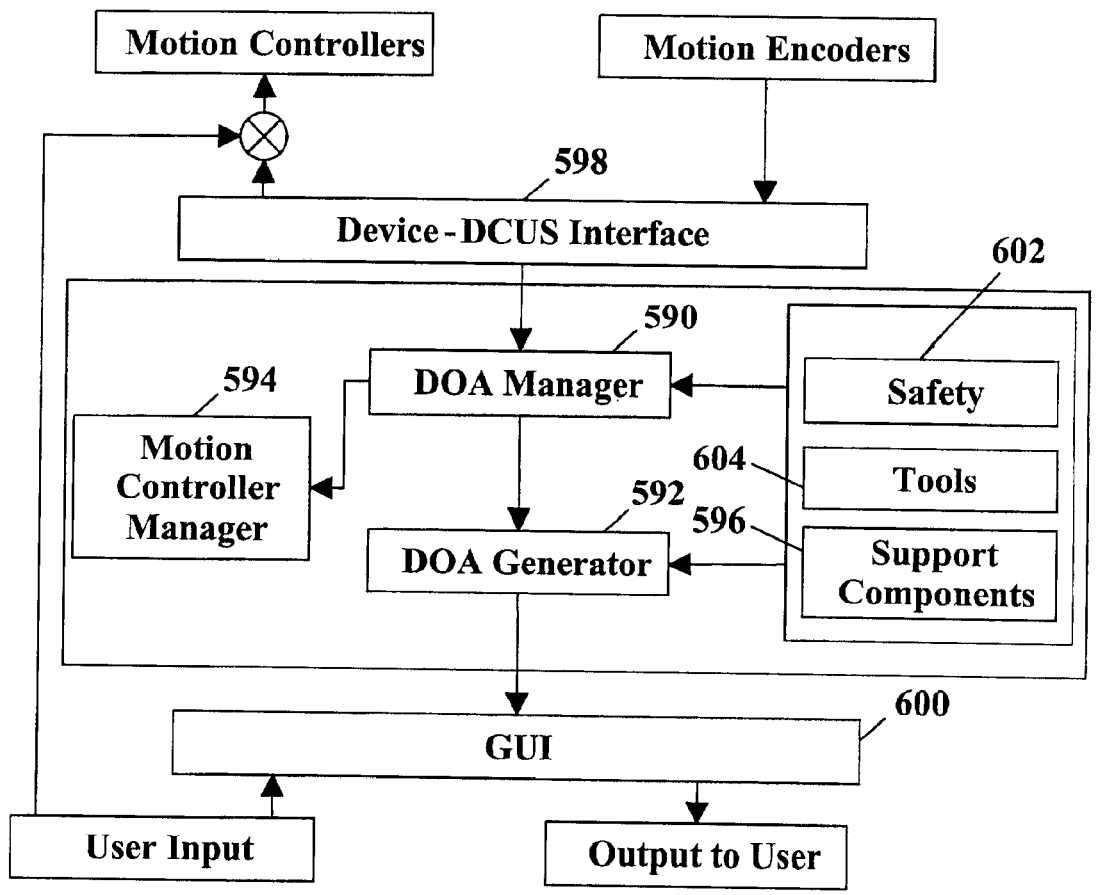
FIG. 13 shows a flow sheet for a general structure of the device control unit and software (DCUS) structure.
Figure 14:
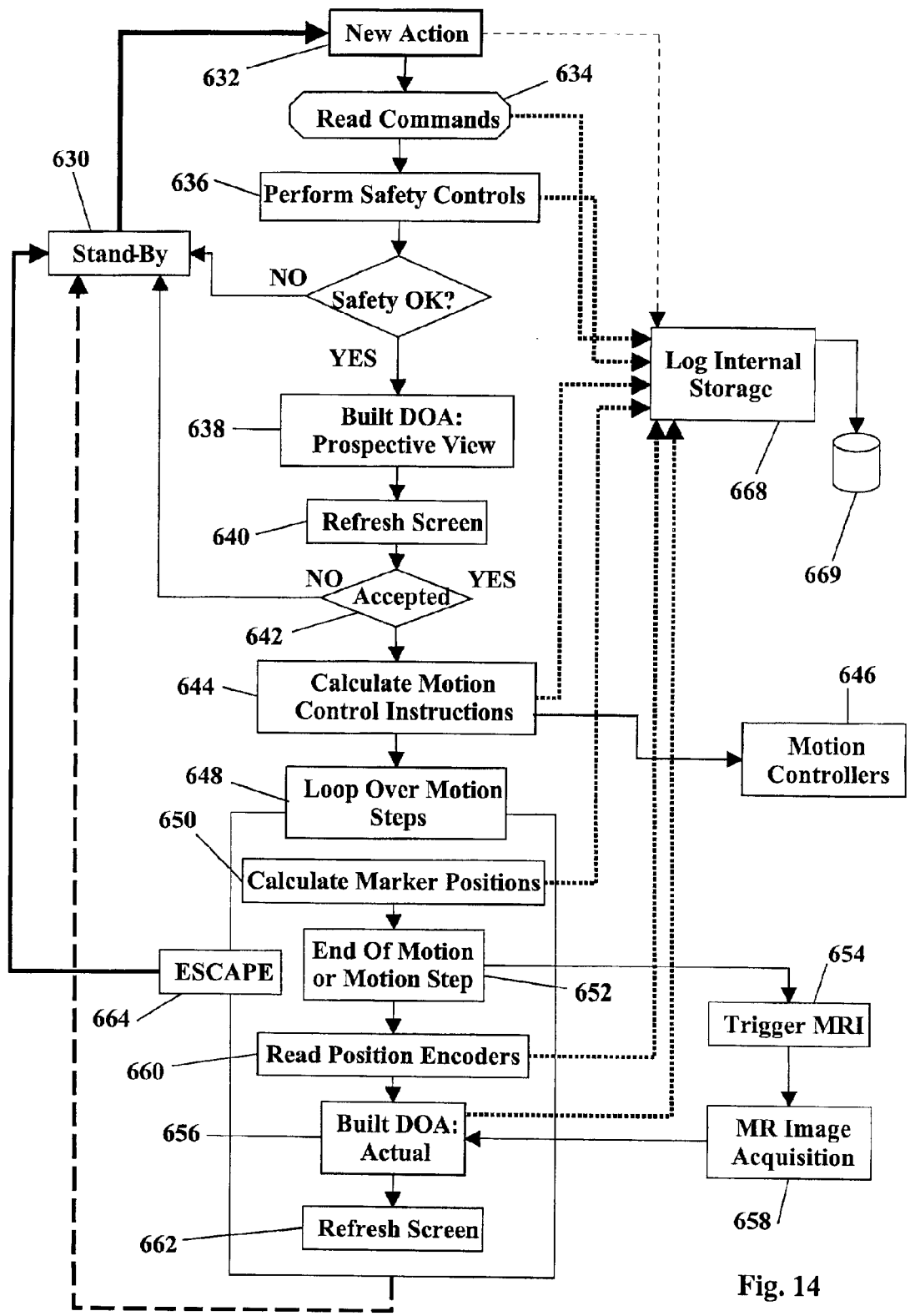
FIG. 14 shows a flow sheet Example of a Software Operation useful within the scope of the present invention.

The PD is an assembly of components with given degrees of freedom, as for example described in FIG. 3, such to facilitate the purpose of delivering an intervention to the breast, according to the method of delivering the intervention, illustrated in FIG. 2, and operation (FIGS. 13 to 14).

The control unit includes a computer processing unit (42), software (138), user input devices, such as keyboard (51), joystick (53) and microphone (55), peripheral components, such as data storage unit(s) (57), monitor (44), control unit to device interface (59). The interface (59) has an output to the drivers of the actuators (61) and an input from the position encoders (63) on the device.

Furthermore, the device actuators are equipped with position encoders in order to verify the particular motion instructed by the DCUS as set by the operator. Such position encoders should be operational inside the magnetic field generated by the MRI scanner, such as optical encoders. Feedback signal lines 63 are running from the encoders to the motion controller(s) 26, say line 36, and to the DCUS 20, say line 37.

The DCUS 20 is an assembly of hardware and software for (a) planning the intervention, (b) controlling and (c) monitoring the motion of the actuators, and thus of the PD. The hardware of the DCUS is this required for the control of the actuators as defined by the manufacturer of particular used product. The software of the DCUS is comprised of (a) software for planning and monitoring the intervention with the particular device as described in this invention, (b) software provided by the manufacturer of the actuators for their control and (c) software provided by the manufacturer of the position encoders for assessing their values. In generally, these components of software are integrated and can exchange data for their efficient operation according to this invention, as for example described in FIGS. 13 and 14. Such structure is, in generally available, as for example, C language routines and modules and the development of the integrated software is straightforward based on the programmer's manuals of the modules.

The DCUS 20 may be integrated to the MRI host-processing unit, as for example, an add-on component 40, or can be a stand-alone unit 42. In the first case this can be achieved by incorporation with the software of the scanner or can reside on a data-carrying medium. In the later case, the DCUS is situated in a host-processing unit 42 and can be at any operating platform, such as a PC or an Apple, or a UNIX box. At this case the DCUS includes at least a monitor 44 and peripherals 46.

The DCUS is, in generally, situated outside the MRI scanner room and, preferentially, is installed on the MRI console or at its proximity, so that an operator has unobstructed access to both. In generally, it is preferred that the DCUS is connected with the scanner processing unit for direct exchange of data. In the most efficient version of the system, the DCUS can receive directly data 48 from the MRI scanner, such as the images and their parameters, such as the field-of-view (FOV) and their orientation in the space. In the case that the DCUS is integrated to the scanner then this can be done by means of standard methods known to the manufacturer of the scanner. In case that the DCUS is a stand-alone unit, then several methods for data exchange can be used, as for example the link 48 can be a local network for data transfer based on optical or other medium. Furthermore, the DCUS can retrofit data 50 resulting from the process of planning the intervention as described herein. Such data can be the particular type of pulse sequence, which drives the MRI scanner, chosen by the operator to optimize the MRI guidance, the spatial set-up, such as slice(s) orientation, FOV and MRI acquisition triggering signal.

According to another aspect of the invention, the components inside the MRI scanner are located underneath the patient who is lying in the prone position on an elevated surface 52 above the device 14. The elevated surface provides an appropriate opening 54 on its upper surface 56 for the breasts to pass-through and be dispensed in the area between the upper surface of the stage 56 and the surface of the couch 58. In generally, the elevated surface 52 is anchored on the patient couch, at predetermined positions, so that the opening 54 is over the PD 14 within the volume of highest magnetic field homogeneity. The elevated surface 52 may be part of a single construction, which includes the PD and thus can placed on the couch 58 as a single component. Furthermore, the stage 52 provides access ports for the connection of the motion control links, say 30 and/or 35, the feedback from the position encoders 37, and the RF coil 60, in case that an RF coil is used, which is not provided by the OEM of the scanner. These connectors can be of appropriate type required and can be located generally on the side and toward the legs of the subject for minimal interference with the subject, the operation of the device or the support personnel. The described components are inside the MR scanner room and are connected with the outside via appropriate connections, as for example, the standard RF connection and a wave-guide for the rest. Both of such connections are standard in most of the clinical and research facilities.

According to another aspect of the invention, the collection of the NMR signal to generate MR images and guide the device may implemented by two general ways. In the first approach, a specialized radio frequency (RF) coil (not shown in FIG. 1) suitable for the particular design and dimensions of the device can be used. Alternatively, and according to this invention, the body RF coil of the standard MRI scanner can be used. The body RF coil can provide a panoramic view of the area of operation, however, with the expense of lower sensitivity in the collection of the signal. A specialized coil can be either one covering the area defined by the motion of the device on the horizontal plane or one attached on the device as discussed in accordance with any of the Figures. In case that a specialized RF coil is used, then this system can be used for both RF transmission and reception or as reception only, with the body coil used for transmission. In either case, the elevated surface may provide a port, say port 60 in FIG. 1, for the connection of the RF coil with the RF interface of the MR scanner 38 via a cable 62 through the standard access provided by the OEM of the particular scanner on the RF cage wall.

Description of a Method of Positioning an Interventional Probe:

FIG. 2 illustrates the principles of the intervention and operation of the device. Furthermore, these principles dictate the particular design of the PD 14, the choice of the actuators 16 or 18, the choice of E-M transducers 22 or 24 and corresponding drivers 26, as well as the design and implementation of the DCUS 20. Most importantly, these principles determine what particular degrees of freedom will be implemented in a device 14.

In accordance with FIG. 2, the device provides the means for positioning an interventional probe to access a target (T) 70 in the breast 72 through a trajectory 74. According to the invention, the breast 74 is at a compressed state, as compared to the uncompressed breast 78, by an operator-set orientation defined, as for example by the plane 80. Furthermore, the interventional probe will transverse a portion of tissue at a depth (D) along the trajectory 74, say segment AT. As depth of intervention we may define the distance AT from the surface of the compression plate 80 to the target 70 along the trajectory 74. In an instrument-specific contest, the depth D can be defined as the distance between the target T and the tip of the interventional probe, at the armed state before insertion, and when aligned with the trajectory 74.

In the particular case, described herein, if the compression plane 80 is vertical in the real space, then the projection of the trajectory 74 on the horizontal plane, say BT, is perpendicular to the compression plane 80. In general, the arrangement of the operator-defined compression plane 80 and trajectory 74 can be described using a R coordinate system 82 and a rotated one Q 84, both centered at the target T. One of the axis of the coordinate systems, say r3 and q3 respectively, coincide. In the R system, the trajectory 74 and plane 80 can be defined by the Euler angles φ 86 and θ 88 and the depth (D) of intervention (AT). The Euler angles can be defined as follows. If the line BT is the projection of the trajectory 74 on the plane $r_1$–$r_2$, then φ is the angle between the BT and axis $r_2$. This rotation defines the axes $q_1$ and $q_2$ of the rotated coordinate system Q 84, as shown in FIG. 2B. Then, θ is the angle between the trajectory 74 and the axis $q_2$ (or equivalently line BT, or plane $r_1$–$r_2$ or $q_1$–$q_2$).

Furthermore, according to another aspect of this invention, the degree of compression can be regulated perpendicular to the projection BT of the trajectory 74 onto the horizontal plane $q_1$–$q_2$. For example, this can be accomplished by setting the compression plane 80 at a desired position as compared to the uncompressed breast 78, as described by the circ plane 90.

Furthermore, and according to another aspect of the invention the above description defines a least number of planes of MRI images, which can be used to guide the placement of the interventional probe. For guidance of the compression process, a plane $r_1$–$r_2$ can be used, which is passing through the target T as identified and set before compression. In the case that compression changes the position and shape of the targeted area, as for example a mass, due to alteration of the geometry of the tissue, the target and the trajectory should be, in generally, reset at post-compression. For resetting the trajectory 74 due to repositioning of the target along the horizontal plane, a plane r1–r2 can be used, which is passing through the target T as identified and reset after compression. Note that the angle φ does not change during such adjustment. For guidance of aligning the intervention probe with the trajectory 74 relative to the horizontal plane (set of angle ), an oblique plane can be used, which is perpendicular to the compression plane 80 and is passing through the target T as identified and reset after compression.

In general an imaging modality, and especially MRI for this invention, is used in order to define the optimal plane of compression 80 and a trajectory 74 as dictated by the particular anatomy of the breast, position and shape of target and internal structures of the breast, an art known to the interventionist. The method described herein, specifies that based on the aforementioned analysis of diagnostic images, the operator performs the following actions: (a) decides on the desired orientation of compression (as may described by the line BT); (b) the degree of compression, as for example conditioning the breast shape from the pre-compressed plane 90, to the post-compression state plane 80 (c) fine adjust the trajectory 74 perpendicular to the compressed plane 80 and (d) define the angle θ of the trajectory 74. Furthermore, according to the remote control of the device, any of the above steps or combination may repeated in order to perform an interventions to the same or other targets during the same session, given that there is the capability of the interventional probe to sample multiple samples during the same session.

According to another aspect of the invention, the method presented here in accordance with the positioning device can be used in order to place an instrument or device externally to the breast with an operator defined orientation and degree of compression as described above.

Description of an Interventional Device

The interventional device 14, as described in FIG. 3, is comprised of a base (100), a platform (102), two plates A and B, 104 and 106, for the compression of the breast, an intervention stage 108, an intervention guide 33, means of delivering controllable motion through actuators 16 or 18 (of FIG. 1) and evaluating the position by means of position encoders. Furthermore the device is constructed by non-magnetic material, which, preferentially gives no signal detectable by a MR scanner and affects minimally the homogeneity of the main magnetic field. In addition, the device has MR visible markers, described in FIG. 4, of shape dimensions and positions determined by the need to monitor MR-guided interventions as described herein.

The base 100 provides the means for motion of the horizontal plane for positioning of the interventional components. Furthermore, the base 100 carries the platform 102 in such a way to allow rotation of the entire platform relative to the base around the vertical axis $r_3$. To another aspect, the base provides the means for anchoring the entire device on the MRI patient couch surface 58 (of FIG. 1) for stability. Furthermore, the coordinates of a point on the device 14, or any one of its components, as for example the compression plate 104, can be unambiguously determined relative to a Cartesian system, say R, centered at the isocenter 101 of the MRI scanner. Such system can be aligned with the principle axis of the MRI scanner. According to the art of MRI scanning, the patient is positioned in such a way that the imaged area is in generally situated at the isocenter, as for example in-between the breasts, for optimal magnetic field homogeneity and thus the highest MRI signal. The motion and position of the base can be described relative to the system R 82 (same as in FIG. 2A). For example, the base 100 can move on the horizontal plane, generally defined as the $r_1$–$r_2$ plane, which can be, for example, the XZ plane of a MRI scanner with horizontal cylindrical bore.

Figure 3A:
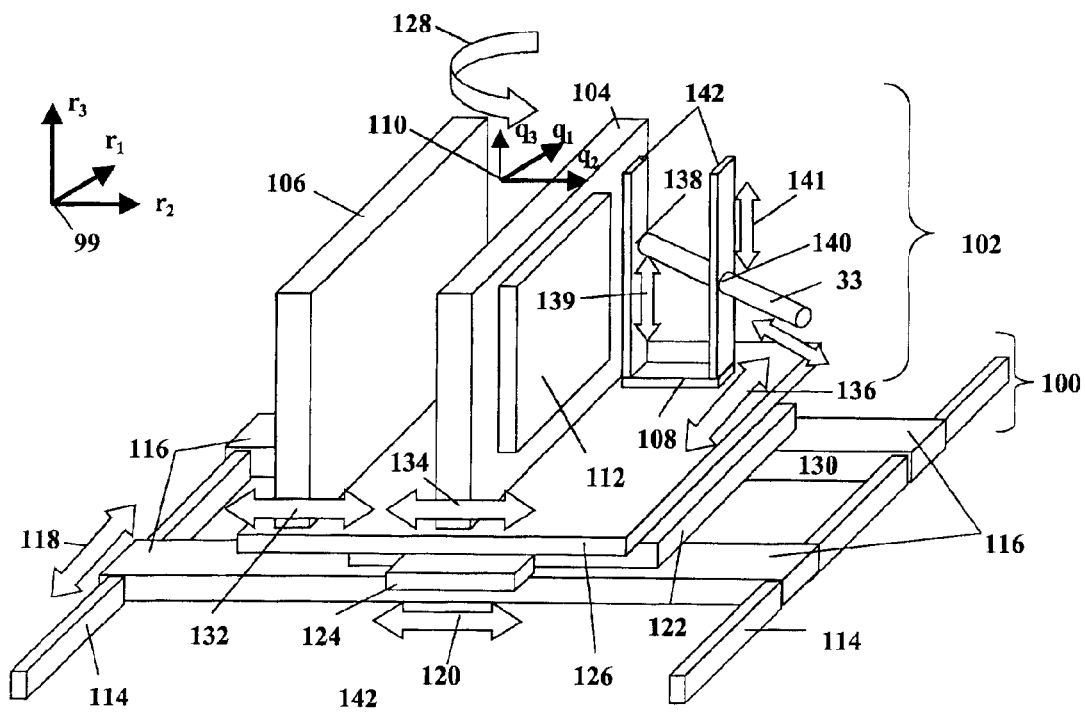
FIGS. 3A, 3B, 3C and 3D show perspective (3A) and side (3B, C and D) illustrations of a device within the scope of the invention and its associated degrees of freedom.

The platform 102 is attached on the base 100, and provides the means of rotational motion around a vertical axis, in generally an axis $r_3$ of the system R, which can be, for example, the Y-axis on a cylindrical horizontal MRI scanner. This degree of freedom provides user defined direction of compression and, thus, any direction of access to the breast defining the angle $\phi$. The platform carries the two compression plates 104 and 106, the intervention stage 108, and the intervention guide 33. Furthermore, it provides the means for controlled motion of the aforelisted components according to the aspects of this invention. The combined two dimensional linear motion of the base 100 and the rotation motion the platform 102 results in the definition of a second coordinate system, as for example coordinate system Q 110 described by the axes $q_1$, $q_2$ and $q_3$. The system Q in FIG. 3A is the identical with the rotated system in FIG. 2. In general, one of the Q axes is parallel with one of the R axes, as for example $q_3$ parallel to $r_3$, which is the axis of the platform rotation. The motion and position of the components attached on the platform, for example the compression plates, can be unambiguously described in terms of the second coordinate system Q. Furthermore, they can be related to the primary coordinate system R by translation (motion of base 100) and rotation around axis $r_3$ by an angle, as for example $\phi$ (rotation of platform 102).

The compression plates 104 and 106 are mounted on the platform 102 in such a way that they can independently move along one of the rotated axis, for example around axis $q_3$, and parallel to the horizontal plane $q_1$–$q_2$ of the coordinate system Q. Furthermore, one of the plates, for example plate A 104, has a window opening 112 to provide access for the interventional probe along the direction defined by the guide 33. Due to the design of the device, the compression plates 104 and 106 are always parallel to each other, perpendicular to the platform 102 surface and their relative position along the $q_2$ axis can be independently regulated by means of linear actuators.

The intervention stage 108 is mounted on the platform 102 in such a way that it can independently move along one of the rotated axis (on the horizontal plane $q_1$–$q_2$) of the second coordinate system. This axis, for example axis $q_1$, is the axis perpendicular to the axis that the compression plates are moving, i.e. axis $q_2$. The intervention stage provides fine adjustment of the interventional probe perpendicular to the compression plates for, as an example, adjustment to account for the relocation of the targeted area due to compression or for interventions to other target(s). Furthermore, the stage 108 caries the instrumentation to provide adjustment of the interventional guide angulation relative to the horizontal plane, for example plane $r_1$–$r_2$ on the R coordinate system or plane $q_1$–$q_2$ on the Q coordinate system. As such, the angle of the line connecting them, line from bearing 138 to 140 can be adjusted. This line defines the line or trajectory of intervention, and coincides with the intervention guide 33, which carries the interventional probe (s). The intervention guide 33 provides the means for the attachment of the interventional probe chosen for the particular intervention. Preferentially, it is a universal base that allows the use of an array of devices.

The several degrees of freedom described herein, as well as others that might be necessary, require accurate remote control. Delivery of motion can be accomplished by, but not limited to, the following means: (a) ultrasonic motors, directly placed on the device; (b) hydraulic actuators, for example pistons, directly placed on the device; (c) non-iron motors, directly placed on the apparatus or in short distance with flexible drive shafts; (d) electromagnetic motors remotely placed with flexible drive shafts; and (e) combination of the above depending on the particular motion and cost of developing the product. Actuator mechanism can be, but not limited to, the following: (a) directly through gearboxes and screw shafts; (b) directly through gearboxes and timing belts; (c) gearboxes and flexible driving shafts; (c) gearboxes and timing belts; (d) hydraulic pistons; and (e) any dictated by the particular design combination of the above.

Materials of construction of the device should be nonmagnetic to avoid artifacts in the images, such as susceptibility (signal void), distortion of the magnetic field gradients used for localization, and thus inaccuracy in spatial localization. Such materials should be easily machined to give a particular shape according to the needs of the device to perform the task described herein, and not easily worn-out. Such material can be polyethylene terephthalate (PET). Furthermore, other material such as aluminum, titanium or plastic can be used for moving parts drive shafts (spiral screws) and gearboxes. Brass can be used for bearings.
Device Motion:

An interventional device should demonstrate appropriate number of degrees of freedom for access to the breasts, according to the principles of operation of the device described herein. To facilitate the method of operation described above in accordance with FIG. 2, a remotely controlled device is described with sufficient degrees of freedom in accordance with FIG. 3.
Two Dimensional Linear Motion of the Base 100:

Aim: Positioning of the device relative to the breasts by means of a two-axis global motion on the horizontal plane r1–r2. These degrees provide:

(A) Positioning of the device relative to the subject and in particular relative to the target area inside the breasts, accounting for the different anatomies of the subjects encountered, as for example different chest widths, position of the breasts and target on the r2 axis and the r1 axis.

(B) Positioning of the rotation axis at any point on the r1–r2 plane relative to the target for user defined compression planes.

(C) Access to either one of the breasts, during the same session.

Figure 6:
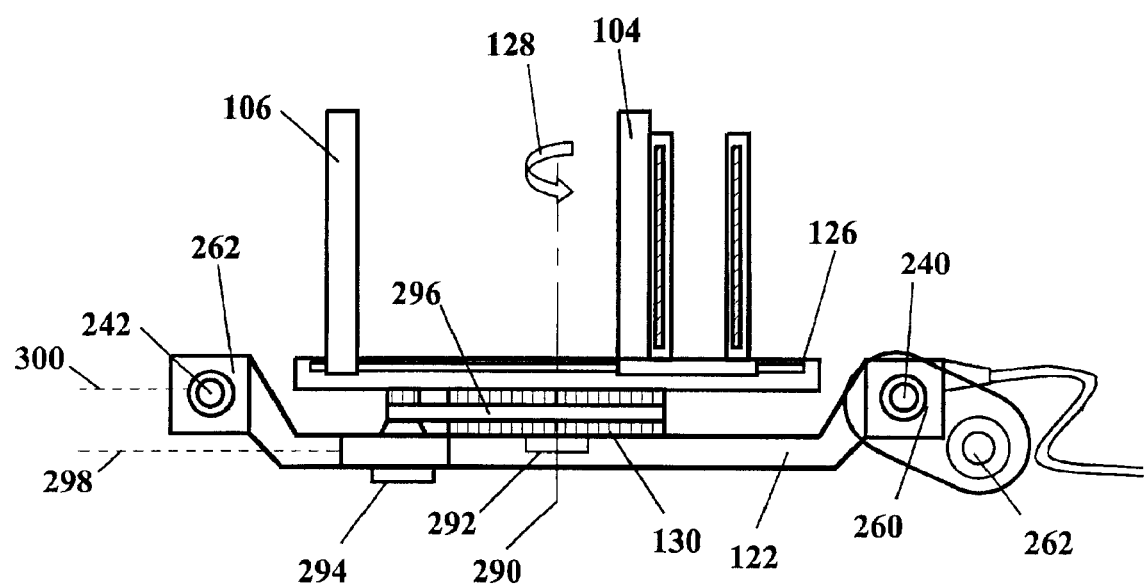
FIG. 6 shows a side view of a Device Platform design within the scope of the present invention.

Means: This can be accomplished but not limited by means of two orthogonal systems of motion actuators 114 and 116 appropriately placed for a two-dimensional motion. One of the motion actuator systems, say 114, is parallel to one of the main axis of the R coordinate system, for example axis $r_1$. The other one of the motion actuator systems, say 116, is parallel to the other the main axis of the R coordinate system which is on the horizontal plane, for example axis $r_2$. One of the motion actuator systems is stationary, for example system 114, and provides the means for the other motion actuator system 116, the mobile one, to move along its axis $r_1$ indicated by the arrow 118. The mobile motion actuator system, for example 116, provides the means for the platform 102 to move along its axis, for example axis $r_2$ indicated by the arrow 120. As result of the combined motion of the mobile motion actuator, say 116, relative to the stationary one, say 114, and of the platform 102 relative to the mobile motion actuator, say 116, the platform can be positioned at an arbitrary coordinate within the constraints of the system. Such constraints are imposed by the travel lengths along the two motion actuator systems, which in turn are determined by the available space available inside the MRI scanner. Another constrain is imposed by the size of the platform. According to another aspect of the invention, as described in detail later and in accordance to FIGS. 6, 7 and 8 the motion actuators can be of several configurations, for example of a cross shape, and can be mobile by several techniques, such as time-belts, screw-shafts or combinations.

Rotational Motion of the Platform 102 (angle $\phi$):

Aim: Positioning of the device for definition of the compression axis 74 of FIG. 2B with global rotation around the vertical axis $r_3$ or equivalently $q_3$ and, thus, definition of the $\phi$ angle 86. This degree provides:

(A) Any arbitrary plane of compression as dictated by the particular anatomy of the breasts, blood vessels, position of the target(s) and other features, which may obstruct or limit the available pathways for intervention, such as implanted material. In generally, can provide the shortest distance to the targeted area. Furthermore, this arrangement can provide standard insertion planes such as lateral, posterior or anterior entrance.

(B) Place the interventional stage close, but not necessarily aligned with the targeted area. Note that, after compression the position and shape will, in generally, change. The motion of the interventional stage 108 will correct for this.

(C) Access anatomical areas with special shape, such as the tail of the axella (fig).

Means: In general, the platform 102 is composed of two surfaces, a lower one 122 and an upper one 126. The low surface 122 is attached on the superstructure of the mobile linear actuator 116, so it can slide along its axis, by means of an appropriate connection 124. The actuator 116 provides the means for the motion of the surface 122 along axis $q_2$, as indicated by the arrow 120. The upper surface 126 can rotate relative to the lower surface 122 as indicated by arrow 128, as for example, by means of a gear 130 driven by a rotational motion actuator.

One-dimensional Linear Motion of the two Compression Plates 104 and 106:

Aim: Independent motion of the compression plates 104 and 106 along the $q_2$ axis, as indicated by the arrows 132 and 134 to deliver the desired level of compression. In a simplified design only one of the planes needs to be movable, i.e. provide the compression, and this can be, for example, plate 104, which is the site of delivering the intervention. However, motion of both plates can be beneficial for better facilitation of the intervention dictated by aspects of the particular anatomy or the art of the intervention. In addition, it can address issues such as areas, which are difficult to be reached, as for example obese subjects.

Means: Linear actuators can drive the two plates 106 and 104 independently, as for example, described in accordance with FIG. 9.

One Dimensional Linear Motion of the Intervention Stage 108:

Aim: Fine adjustment of the position of the interventional stage 108 for alignment with the trajectory 74 (of FIG. 2) my motion along the $q_1$ direction and perpendicular to the compression plane 104 as indicated by the arrow 136. This feature can further facilitate the positioning of the device, especially after the compression of the breast to account for change in the target position and shape. Furthermore it can be used to access additional target(s) when the specific compression plane 104 is the appropriate or almost appropriate for them. As a consequence of this feature, multiple areas can be assessed during the same intervention reducing the overall time of the operation.

Means: A linear actuator can drive the stage 108, as for example described in accordance with FIG. 9.

Angulation of the interventional guide (angle 0).

Aim: Alignment of the interventional guide with the trajectory $T_R$ 74 on the vertical plane, i.e. the plane perpendicular to the compression plane 80. This degree regulates the combined height H and angle $\theta$ 88.

Figures 3B, 3C, 3D:
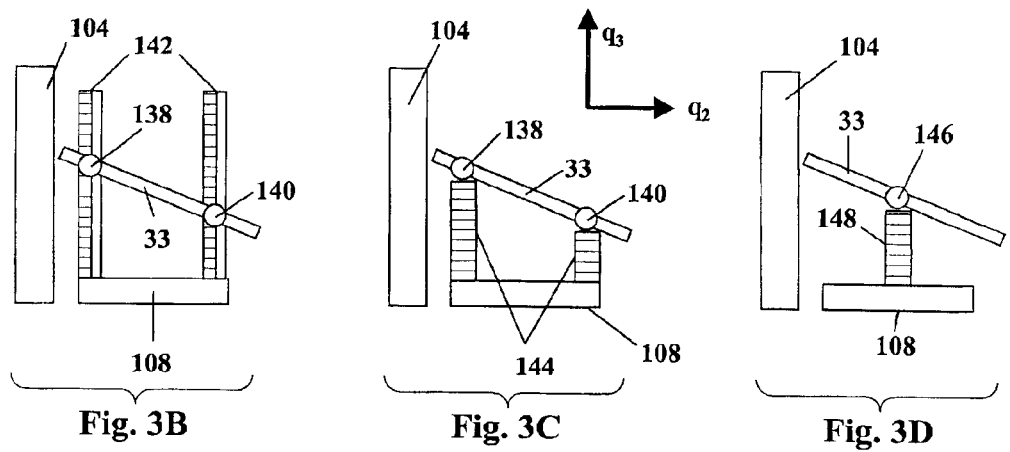
Figures 4A, 4B:
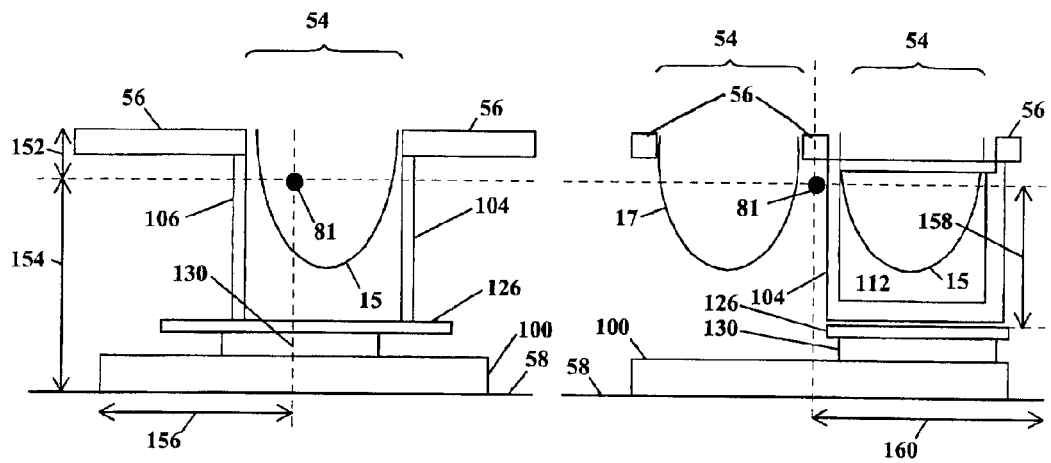
FIGS. 4A, B, C, D, E, F and G are diagrams of a device within the scope of the invention and dimensions and positions of MR visible markers.
Figure 4C:
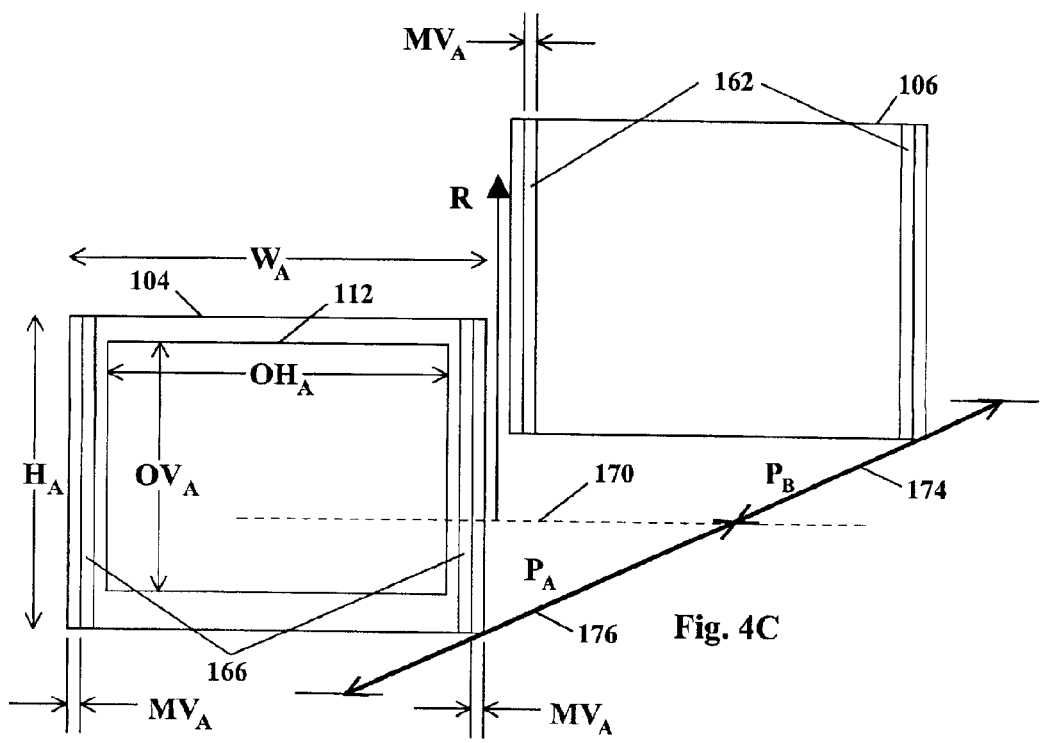
Figure 4D:
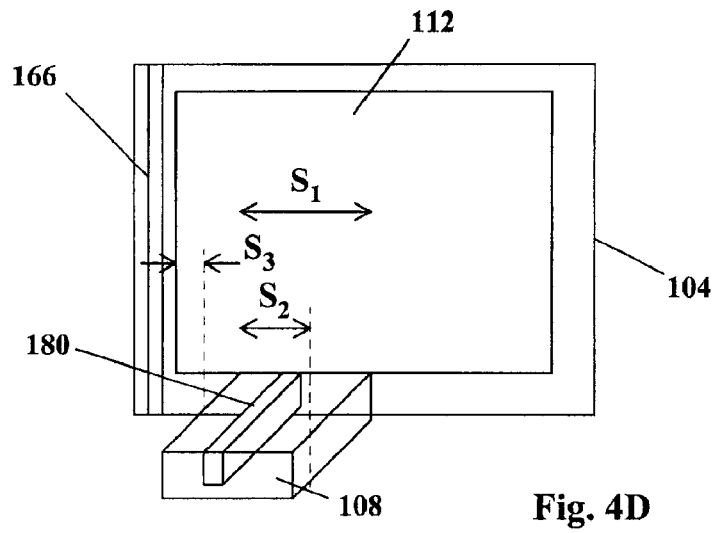
Figure 4E:
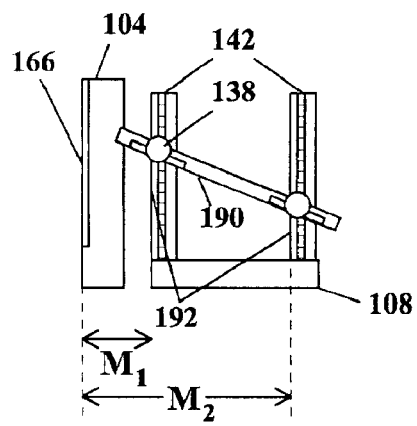
Figure 4F:
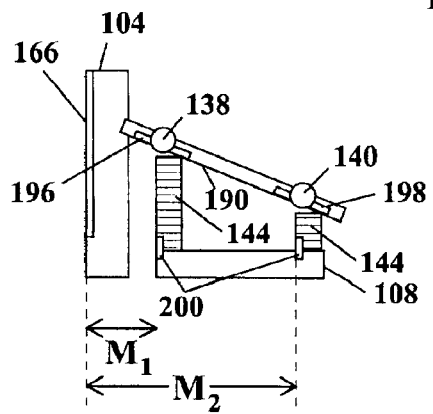
Figure 4G:
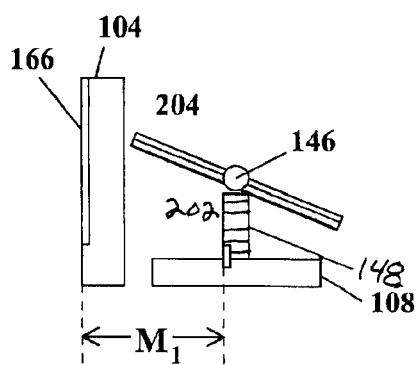

Means: This degree of freedom can be accomplished by several means, such as, but not limited to, a two-pivotal point approach (FIGS. 3B and 3C) or a single pivotal point (FIG. 3D). With the two-pivotal point approach, the stage 108 carries two bearings, 138 and 140, which carry the interventional stage 33, as illustrated in FIGS. 3B and 3C. Thus, the interventional guide 33 line can be adjusted in height and angulation. The vertical positions, along the current $q_3$, of the axis two pivotal points 138 and 140 can be independently controlled by means of linear motion actuators, as indicated by arrows 139 and 141. This can be accomplished by, for example, using two vertical poles 142 of a given height equipped with linear actuators to facilitate control motion of the pivotal points 138 and 140, as illustrated in FIG. 3B. Alternative, the two-pivotal point version can be accomplished with two extendable poles 144 controlled by linear actuators. Such constructions are discussed in accordance with FIGS. 12A and 12B. Furthermore, the guide is equipped with a mechanism to account for the change of its length for different values of angle $\theta$. An example of such mechanism is described later in accordance with FIGS. 12C and 12D. With the single-pivotal point approach, the height and the angulation of a single bearing 146 carrying the interventional guide 77 are adjusted. This can be accomplished by means of a linear actuator 148, for example identical with this used in FIG. 3C, also equipped with a mechanism to rotate the guide and lock it in position.

One Dimensional Linear Depth Set-up (19):

Control of the depth along the trajectory defined by the interventional guide.

For the device described in FIG. 3 are required nine actuators, of which eight are linear and one is rotational and for the alternative design of the interventional stage seven are linear and two are rotational.

Additional degrees of freedom can be added on the PD in order to facilitate its operation according to the principles of the invention, i.e. access to a target point with high degree of flexibility in the compression plane and the trajectory of access. Such additional degrees of freedom can be, but not limited to, (a) adjustment of the height of the plates, (b) adjustment of the angle of the compression plates relative to the vertical plane, (c) angulation of the compression plates relative to a pivotal point and (d) angle of the interventional stage relative to the Q axes (rotation around an axis q3).

Base: Example Design 1

FIG. 5 shows example construction of a base based on drive shafts. The stationary linear actuator is composed by two shafts, 210 and 212, that can freely rotate by means of the bearings 214, 216, 218, 220, and 222. The bearings are anchored on the couch table by means of detachable attachments, such as screws. One of the shafts is a driving ground screw, for example 210, connected to a source of rotational motion 224 through an axle 226. Furthermore, a gearbox 228 can be included between the motion source 224 and the driving screw 210 for reduction of number of revolutions. The source of rotational motion 224 can be, for example an ultrasonic motor or an iron-free dc motor directly attached at position 224.

Figure 5A:
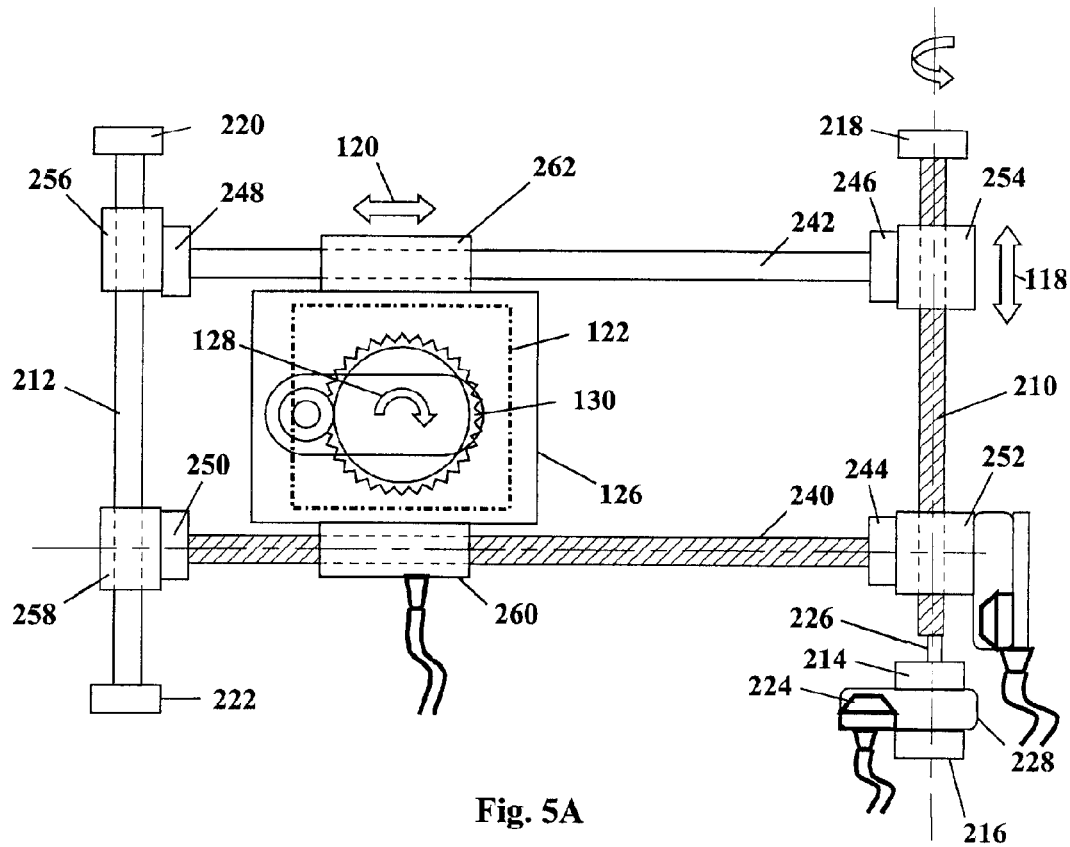
FIGS. 5A, B, C and D show Device Base designs within the scope of the present invention.
Figure 5B:
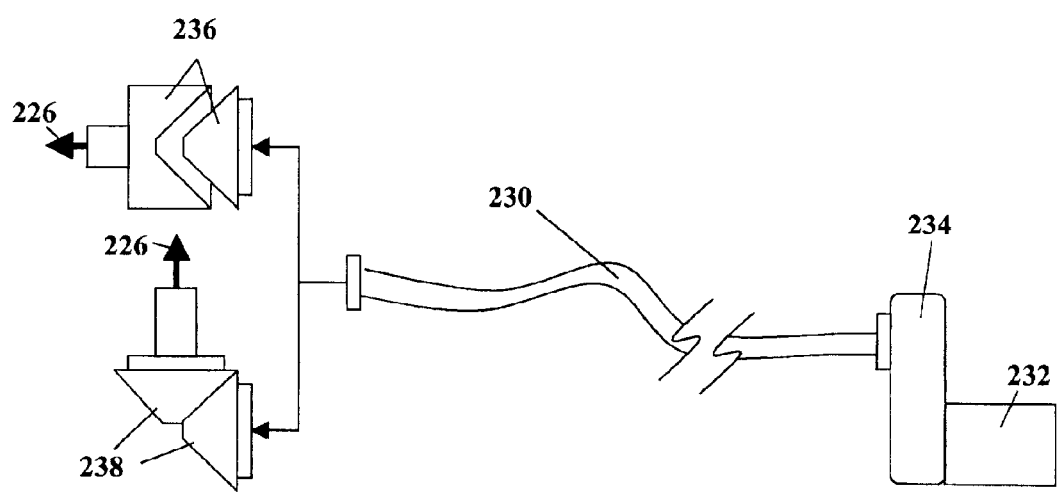

Alternatively, and according to another aspect of this invention, the rotational motion can be transferred with flexible driving shafts 230 from a distant source, as illustrated in FIG. 5B. In such implementation, a conventional stepper or brush-less motor 232 controlled by the motion controller 26 can be used as sources of rotational motion to a flexible drive shaft 230. The driving shaft 230 is connected to the appropriate port of motion input, such 226, on the device. Note that this implementation provides the additional benefit that the gearboxes are located away from the device reducing its size and complication of construction. As a consequence the flexible shafts, like 230, are attached directly onto the axle 226 of the shaft 210, rather via a gearbox. Furthermore, the connection of the flexible shaft 230 may include appropriate quick release head, say 236 for facilitating maintenance or upgrade. In addition, the connection can include an appropriate orthogonal transmission if such is desirable for better implementation of the construction.

The mobile actuator is composed by two shafts, 240 and 242, which can freely rotate by means of the bearings 224, 246, 248, and 250. The bearings are anchored on guides 252, 254, 256 and 258, which can freely travel along the shafts 210 and 212 as illustrated in FIG. 5A. In particular, the traveling guide 252 and 254 have rollers so that they are engaged to the driving shaft 210, in such a way that rotation of shaft 210 causes linear motion of the guides 252 and 254. As a consequence the entire structure connected to them, the shafts 240 and 242, the platform 122, gear 130 and upper surface 126 can move along the $r_1$ axis. For example, a counterclockwise rotation of the shaft 210 may cause linear motion of the mobile actuator, and the aforelisted components, toward the positive $r_1$ axis, and a clockwise rotation toward the opposite direction, thus positioning the device along the Z-axis of a scanner.

Figure 5C:
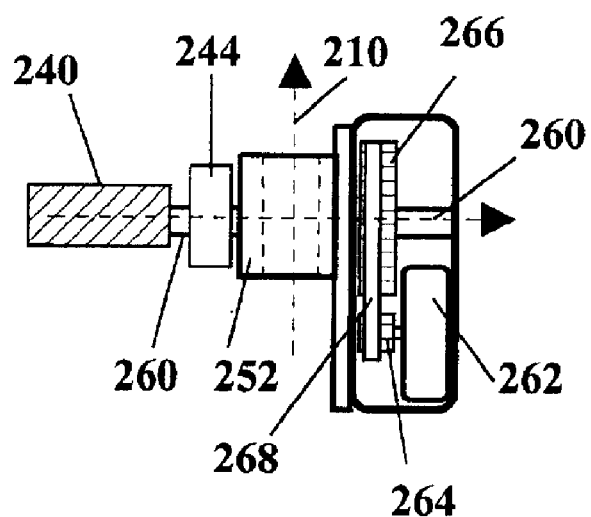
Figure 5D:
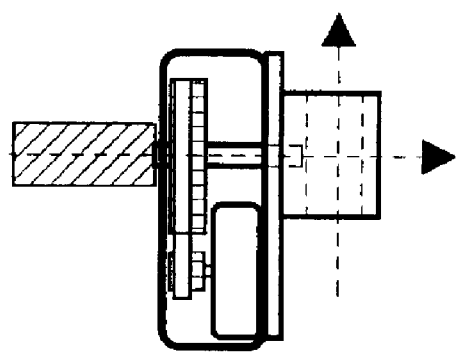

The traveling guide 252 can be implemented in several ways as for example illustrated in FIGS. 5C and 5D. In generally is comprised of a main component which provides a tunnel for the passage of the shaft, say 210. An axle 260 provides rotational motion to shaft 240 and in particular connects it with the E-M transducer 262 or to a mechanical-to-mechanical link such as a flexible transmission line like this described in FIG. 5B. In case that the axle 260 gets mechanical energy from an E-M transducer, the later, say 262, could be directly engaged to the shaft 260 or a gearbox. Manipulation of the rotational motion can be accomplished with appropriate number of inter-engaged gears. This can be also accomplished by means of at least two gears 264 and 266 engaged by means of timing belt 268 as illustrated in FIG. 5C. According to the design illustrated in FIG. 5D, the gearbox and E-M transducer can be positioned at the inside of the traveling guide 252, i.e. the shafts 210 and 240 do not cross their paths. In case of the design in FIG. 5C, i.e. the shafts 210 and 240 cross each other, a potential approach is to have the two shafts on different levels, as illustrated in FIG. 5E.

According to FIG. 5F, a flexible driving-shaft can provide a more compact solution. Several solutions can be adopted for transferring motion from the flexible driving-shaft to the shaft 240. An approach would be the connection of the mechanical-to-mechanical link with the axle 260 by means of two gears, one attached to the axle 260, say gear 270, and one to the shaft 240, say gear 272.

Furthermore, the mobile actuator provides the means for connection of the platform 122, via traveling guides 276 and 278, corresponding to 124 of FIG. 3. The traveling guides 260 and 262 can freely travel along the shafts 240 and 242. In particular, the traveling guide 260 have rollers so that they are engaged to the driving shaft 240, in such a way that rotation of shaft 240 causes linear motion of the guides 260 and 262. As a consequence the entire structure connected to them, the platform 122, gear 130 and upper surface 126 can move along the $r_2$ axis.

Platform Link:

Furthermore, according to another aspect of this invention, the platform 102 can freely rotate as desired by the operator around the vertical axis r3 (or q3), say 290, relative to the base 100 that is indicated by arrow 128. This can be accomplished as for example illustrated in FIGS. 3 and 6. The platform is composed of two plates, a lower one, say plate 122 and an upper one, say plate 126, connected with a gear 130 which one end is attached to one of the plates, say upper plate 126 and the other end can freely rotate in a bearing 292 attached to the lower plate 122. An E-M or a M-M link 294 can provide rotational motion to the gear 130, either with direct engagement or through a timing belt 296 and a gear 298 attached to 294. The later implementation maybe desirable for manipulation of the rotation speed of the upper part. The E-M transducer or M-M link are attached to the lower plate 122. The lower plate can travel along the axes 240 and 242 by means of the traveling guides 260 and 262. One of them provides the means of motion as described in accordance with FIG. 5. Furthermore, the lower plate 122 can be at a lower level say line 298, as compared to the shafts 240 and 242, say line 300, in order to reduce the overall height of the device means of particular construction, such as a "shoulder" 302. The exact elevation of line 300 compared to line 298 will depend on the particular design of the system and spatial constrain, such as the shape of the couch.

Base: Example Design 2

According to another aspect of the invention, the base can be further designed and machined in order to make it with as low height (profile) as possible. This has a major benefit in providing adequate space between the patient surface 56 and the couch 58. According to this aspect of the invention, the base can be design to place all of the motion instrumentation, which can potentially increase the height of the system, outside of the area of operations for the system. As illustrated in FIG. 7 with box 320, an area for the operation of the platform 102 can be defined. This area, is the area underneath the opening 54 of the patient surface 52. The exact dimensions of this area will be determined by the design of the system and spatial constrains, such as the available space in the MRI scanner. According to FIG. 7A, the base can be composed of two linear motion actuators 322 and 324 overlapping outside the area of operations 320. One of the motion actuators, say 322, is along the $r_1$ axis (or the X-axis of a horizontal cylindrical MRI scanner) and is stationary, i.e. anchored on the patient couch 58. The motion actuator 322 provides the means, as for example with a timing belt 326 driven by a E-M transducer or a M-M link 328, for moving the mobile motion actuator 324 along the $r_2$ direction, as indicated by arrow 120. Furthermore, to facilitate motion and stability, the other end of the motion actuator 324 may be connected, as for example, by means of a bearing 330 on a shaft 332 which is anchored on the patient couch 58. The motion actuator 324 provides the means, as for example with two timing belts 334 driven by a E-M transducer or a M-M link 336, for moving the platform 102 along the $r_1$ direction, as indicated by arrow 118. The r1 axis can be, for example, the Z-axis of a horizontal cylindrical MRI scanner.

Figure 7A:
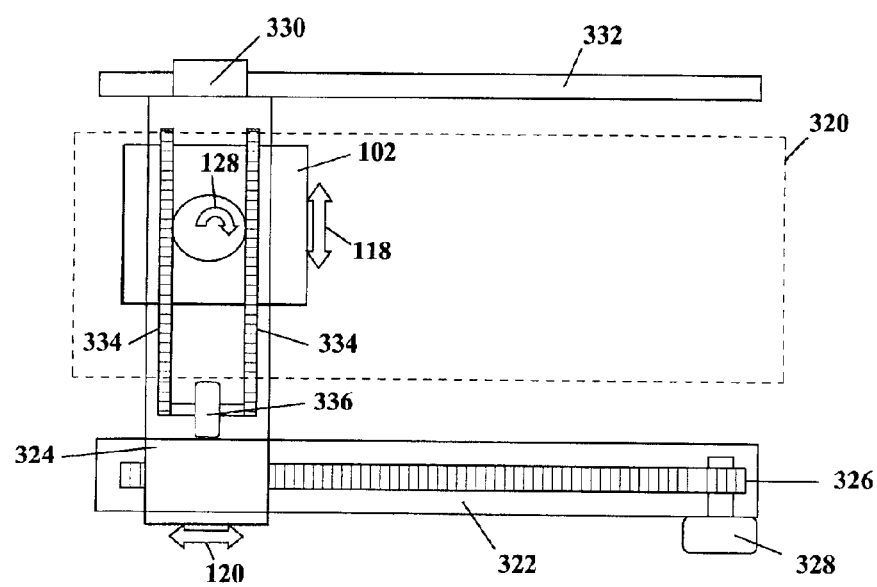
FIGS. 7A, B, C and D show side views of alternative Device Base designs within the scope of the present invention.
Figure 7B:
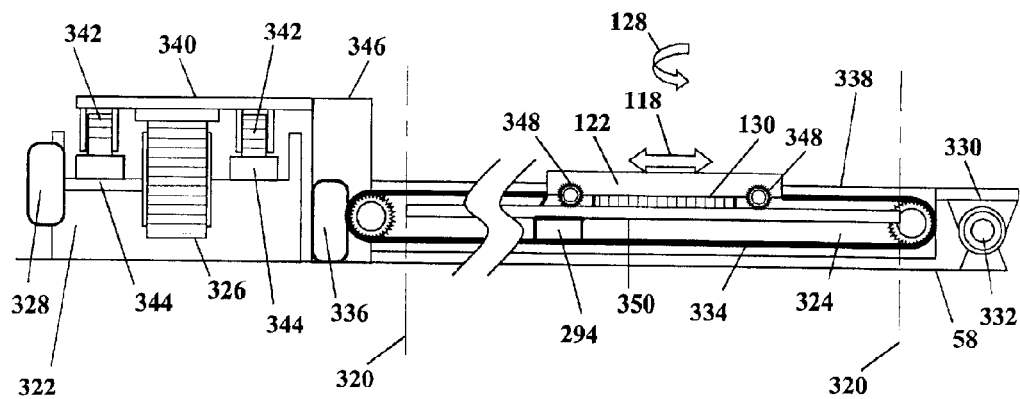
Figure 7C:
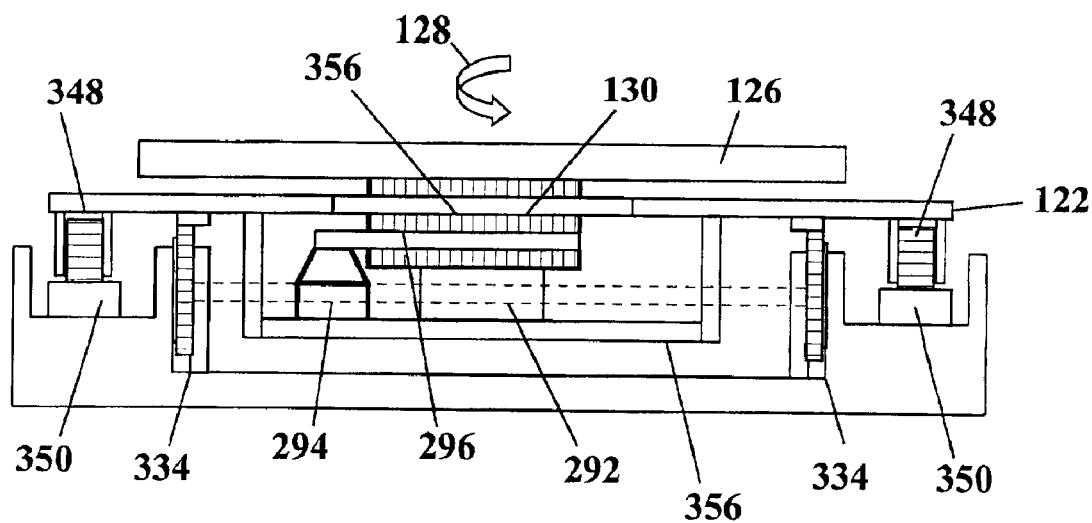

As illustrated in FIG. 7B, such designs allows most of the bulky components, such as E-M transducers and M-M links, to be located outside the operation area 320. In particular, without loss of generality, the mobile motion actuator 324 can be constructed with two levels (in a similar manner with the design in FIG. 6). One level 338, which is the part of the actuator 324 entering into the area of operations, can be designed and constructed to be as low as possible on the vertical axis, i.e. as close as possible to the couch surface 58. The other level 340, which is the part associated with the transfer of motion from the actuator 322 can be higher depending in the particular design of the connections of the two actuators. For example, part 340 may roll by means of graded wheels 342 on top of a graded strip 344, which can be parallel or angulated. A timing belt 326 getting motion from a E-M transducer or a M-M link 328, attached to the part 340. Instead of the wheels 342 can be substituted with shafts. Furthermore a third part, say 346, may be located between parts 340 and 342. This part can be longitudinally deployed and can include the E-M transducer or a M-M link 336 used for motion on the mobile actuator.

Figure 7D:
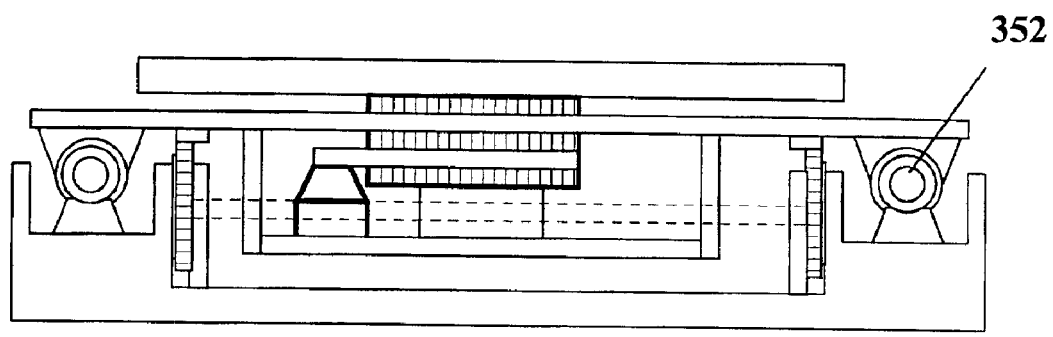

For motion along the r1 axis, the lower surface 122 of the platform 102 can be driven by, for example two timing belts 334 connected to the E-M transducer or a M-M link 336. The platform can then slide either by means of wheels 348 on top of a graded strip 350, or by means of shafts 352. One or two timing belts can be used in this design, depending on the particular design requirements without loss of generally. The rotation mechanism of the platform link can be underneath the lower surface 122 and inside the area in-between the structures used for motion of the platform, i.e. the timing belts 334 and the wheels 348 or the shafts 352 (FIG. 7D). In such approach the rotation mechanism of the platform can be housed, for example, inside a box 354, which has an opening 356 on top, for the gear 130 to pass through. Such placement further facilitates the construction of a low height system. The platform link includes the components described in accordance with FIG. 6, such as the gear 130 attached to the upper surface 126 of the platform 102, a bearing 292 attached to the lower surface 122 of the platform 102, and a E-M transducer or a M-M link 294.

Base: Example Design 3

Figure 8A:
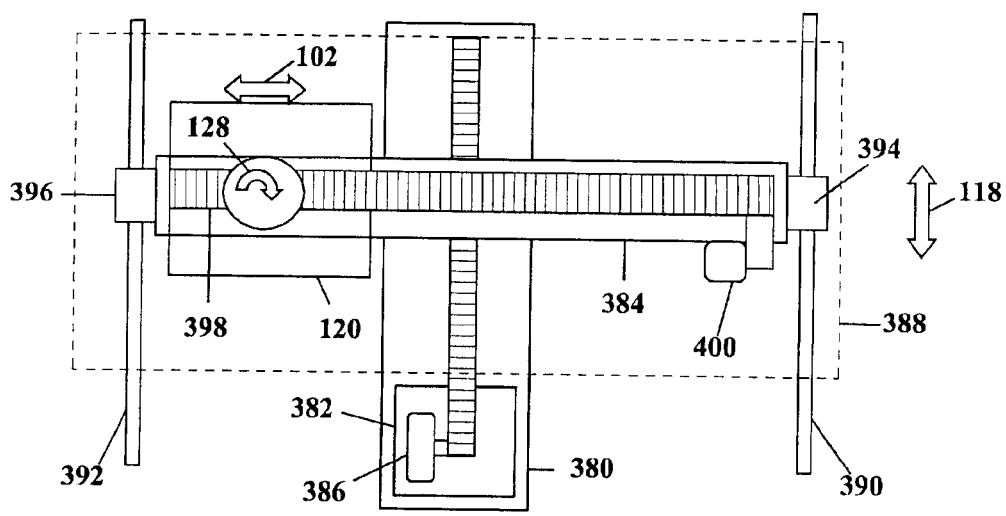
FIGS. 8A, B, C, D and E show further alternative Device Base designs within the scope of the present invention.
Figure 8B:
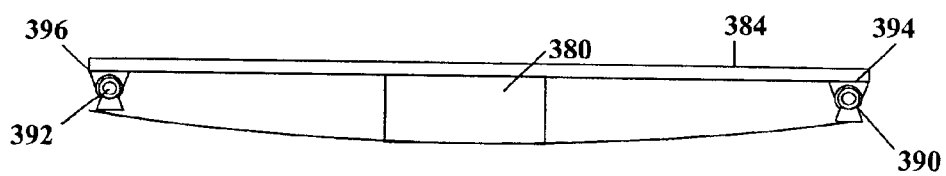

According to another aspect of the invention, the base mechanism can be designed of low profile by placing the stationary motion actuator, say 380, in the middle, along the axial direction of the magnet as illustrated in FIG. 8. At this case, an implementation with timing belts can be adopted, although, driving shafts can be also used. The components 382 associated with motion of the mobile actuator 384, such as E-M transducer or a M-M link 386, are located outside the area of operations 388, facilitating a lower profile. Furthermore, the placement of the stationary actuator in the middle of the couch can take advantage of the cases of couches, which are curved, in the middle as illustrated in FIG. 8B. With the proposed design of FIG. 8, the mobile actuator 384 may travel with the support of two rails 390 and 392 placed at the edges of the actuator by means of travel guides 394 and 396. Furthermore, the mobile actuator carries the appropriate components for motion of the platform such as a timing 398 and a E-M transducer or a M-M link 400.

Figure 8C:
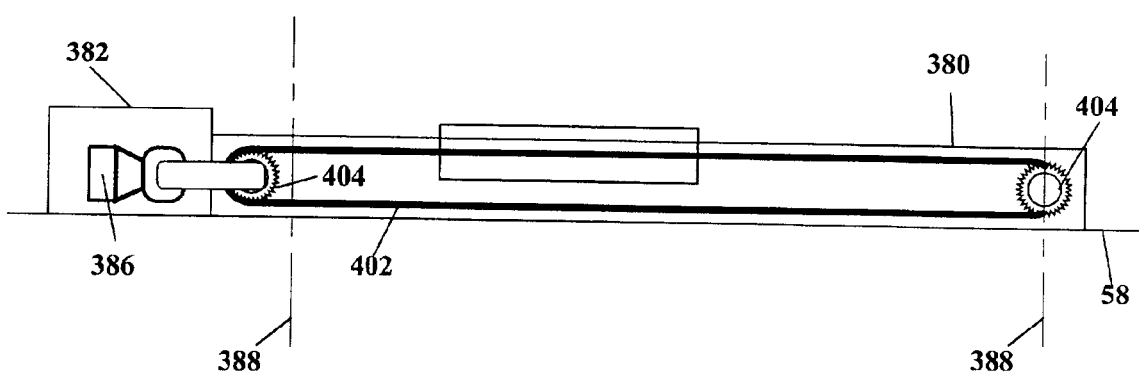

In accordance with FIGS. 8B and 8C, most of the components required for motion on the r1–r1 plane and rotation accommodated in the space between the surface of the couch 58 and the mobile actuator 384. In particular, the height of this space can be as low as required to accommodate the timing belt 402 and gears 404 of the stationary actuator, and the rotational mechanism of the platform. Furthermore, the timing belt 406 used for the motion of the platform 102 relative to the mobile actuator 338, needs to span only partially the lower surface of the mobile actuator.

Figure 9A:
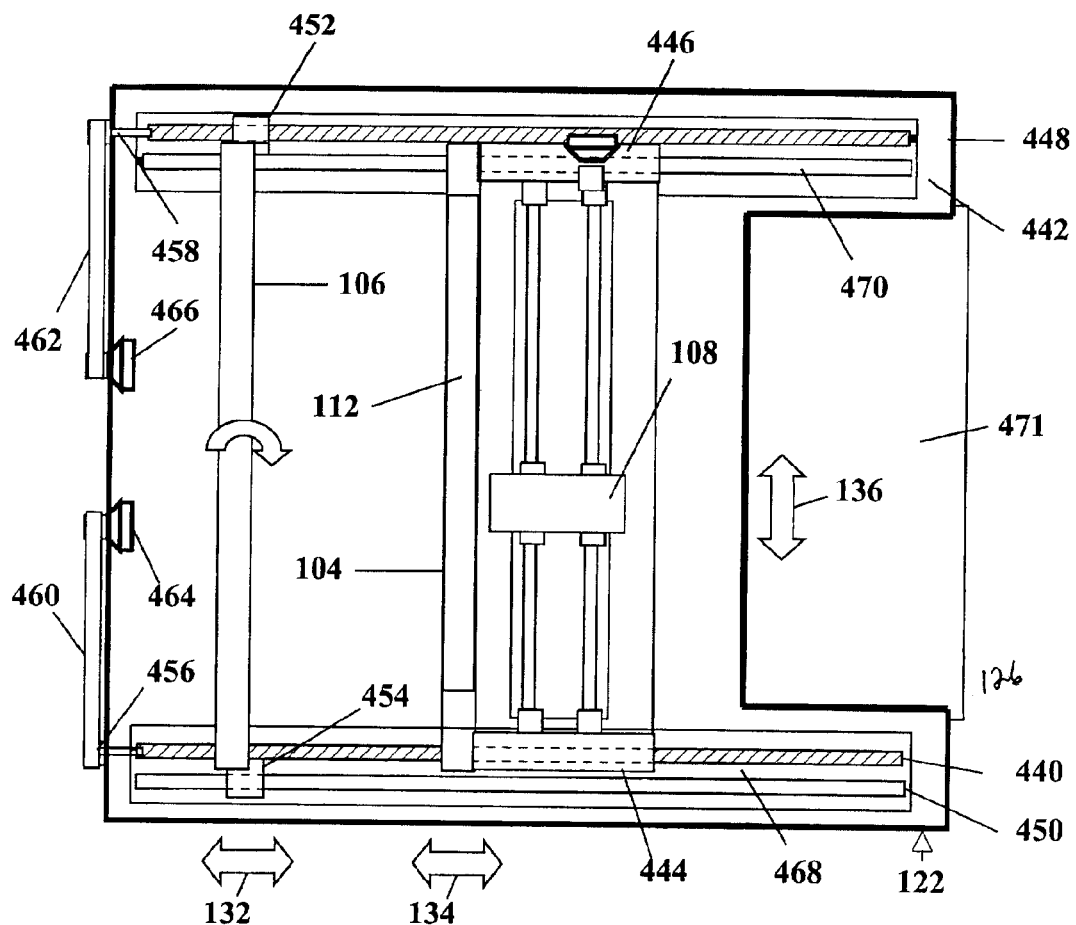
FIGS. 9A and B show side views of Details of one alternative type of a Platform useful in the practice of the invention.
Figure 9B:
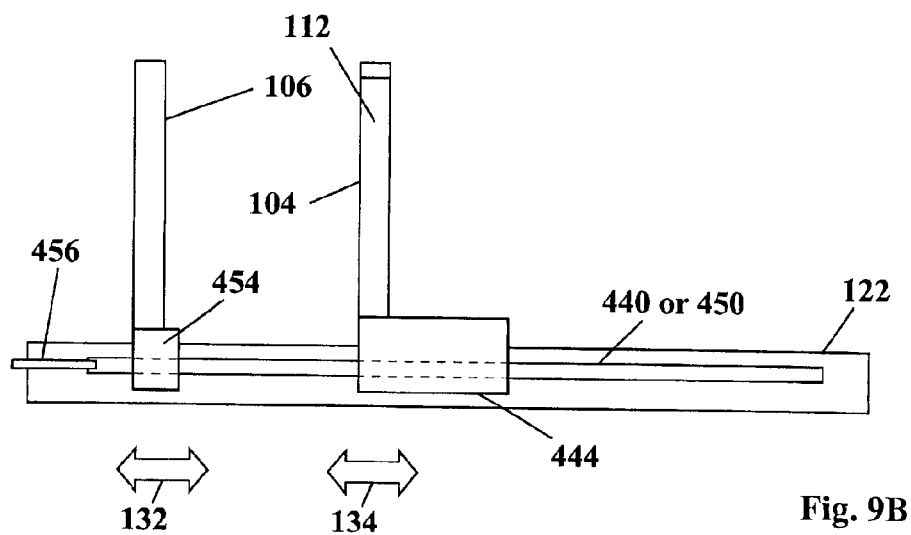

Platform:

In accordance to FIGS. 9 and 10, the platform carries the compression plates 104 and 106, the interventional stage 108, the interventional guide 33 and the actuators associated with control motion of these components. In brief, according to the invention, the compression plates can move independently along the g2 axis as indicated by arrows 132 and 134. The interventional stage can move on the perpendicular axis as indicated by the arrow 136 (q1). Furthermore, the interventional guide can move on the plane perpendicular (fig.); with the mechanisms illustrated in FIG. 3.

The upper surface 122 is composed of three sets linear actuators, two for the motion of the compression plates and one for the motion of the interventional stage.

Compression Plates:

For both compression plates A and B the actuators are similar and can be constructed as described in previous section using, for example driving shafts or timing belts powered by E-M transducers or M-M links. An example implementation based on driving shafts is shown in FIG. 9. The linear actuator for each plate 104 or 106 is composed of two shafts, one of them a driving shaft. In particular, the linear actuator of plate 104 is composed of a driving shaft 440 and a guiding shaft 442. The plate 104 can travel along the shafts by means of traveling guides 444 and 446, of which the one 444 is rotating. The opening provided for access to the breast 112 can be Similarly, the plate 106 travels on the shafts 448 and 450 by means of the traveling guides 452 and 454. The driving shafts 440 and 446 are powered at the power-in links 456 and 458 which can be connected, for example with timing belts 460 and 462 to E-M transducers or M-M links 464 and 466, respectively. To facilitate a construction of low height the shafts 440, 442, 448 and 450 can be installed inside two elongated openings 468 and 470. Furthermore, the surface 122 may have a clearance opening on the side of the interventional stage for better positioning of an elongated interventional probe when in an angle θ. Furthermore, the plate 104 can be used to carry the frame and the actuator of the interventional stage 108, so that motion along the q2, due to compression, will result to corresponding motion of the IS.

Figures 10A, 10B:
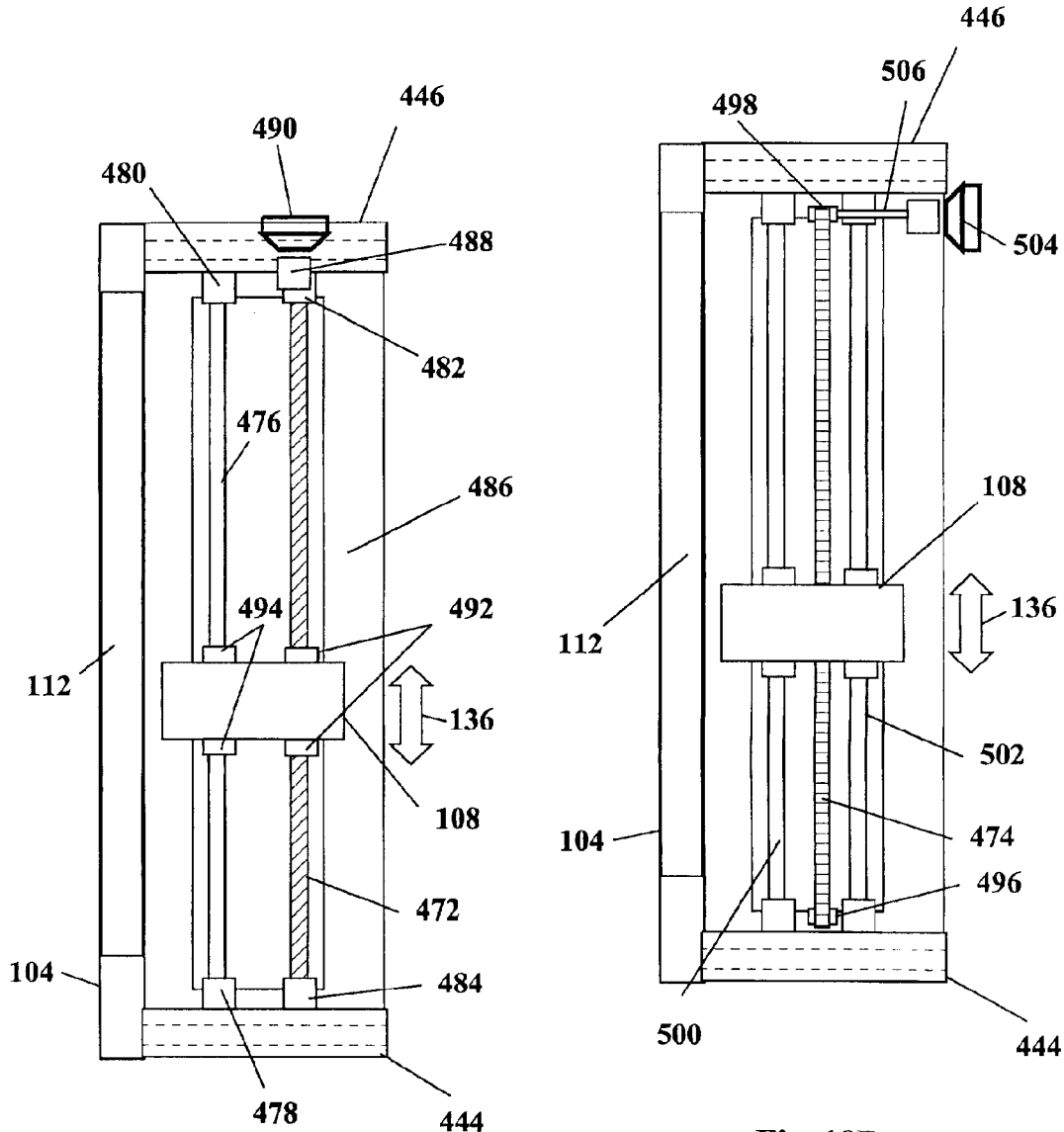
FIGS. 10A and B show side views of Details of an alternative Stage for use within the practice of the present invention.

Interventional Stage:

An example design of the interventional stage (IS) is described in accordance with FIGS. 9A and 10. In this implementation, the plate 104 carries the actuators of the IS 108. This linear actuator can be, for example, based on a driving shaft 472 (example, FIG. 10A) or a timing belt 474 (example, FIG. 10B) implementation. In the first configuration, the actuator may composed of two shafts, 472 and 476, which can freely rotate by means of bearings 478, 480, 482 and 484. These bearings can be attached to the traveling guides 444 and 446 of the compression plate 104. A frame support 486 may or may not included in the design. Either one, or both of the shafts 472 and 476 can be driving. For example, the shaft 476 can be guiding and the 472 driving by means of a mechanical port 488 engaged to a E-M transducer or a M-M link 490. Rotation of the driving shaft 472 can induce linear motion of the 108 along the q1 axis for positioning of the IG. For the design described, the stage is a block which can slide along the shafts 472 and 476 by means of traveling guides 492 and 494. One, or both of the guides, can be graded, say for the particular example traveling guide 492 so that the rotational motion of the driving shaft 472 is converted to linear motion of the platform. Although, it can increase the complexity of the motion transduction mechanism from the mechanical port 488 to the shafts, it may be desirable that both shafts are driving. Furthermore, according to FIG. 10B, the actuator of the stage can be implemented using a timing belt 474 mechanism. In this approach, the timing belt is mounted by means of gears 496 and 498 on the travel guides 444 and 446 of the plate 104. The stage 108 is attached to the timing belt and slides over guiding two shafts 500 and 502 which are attached to the travel guides 444 and 446. The motion of the belt 474, and thus of the stage 108, can be achieved, for example, by means of a E-M transducer or a M-M link 504 which is connected to one of the gears, say 498, by an axle 506 via a mechanical port or axle 504.

Figure 12A:
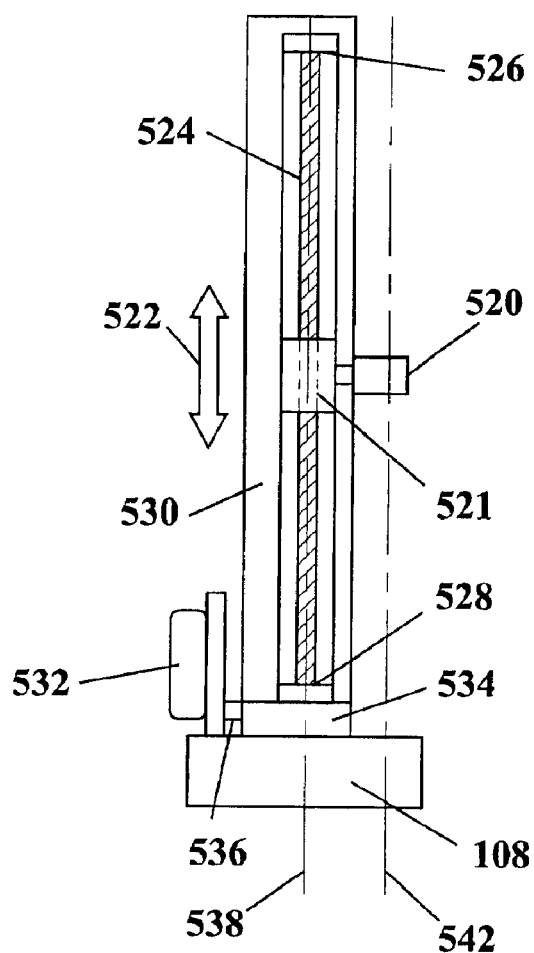
FIG. 12 shows side views of angulation mechanisms within the scope of the present invention.
Figure 12B:
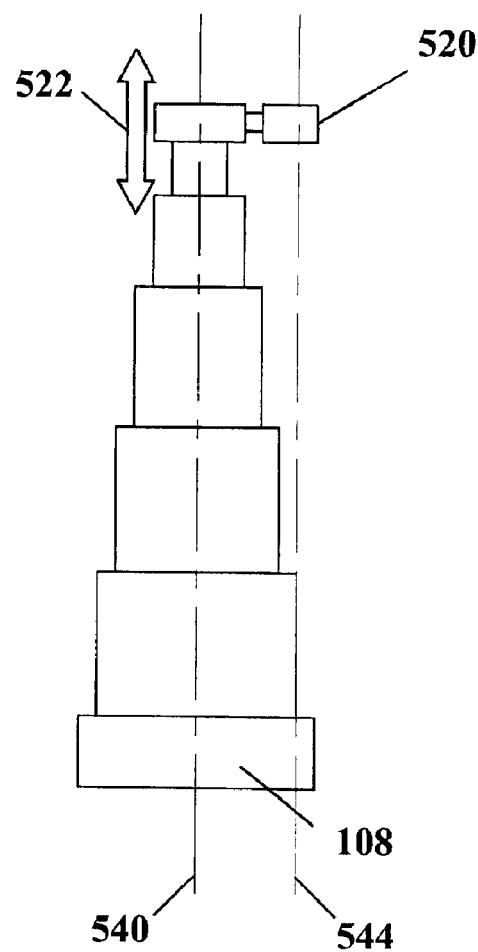

Interventional Guide:

A two-pivotal point mechanism for positioning of interventional guide IG is described in accordance with FIGS. 3 and 12. For example, the adjustment of the height of each pivotal points 138 or 140 of FIG. 3 can be implemented with two linear actuators, one for each pivotal point. FIGS. 3A, 3B and 3C illustrate three possible approaches for implementing a linear actuator to move a pivotal point, say 520, along the vertical direction as indicated by the arrow 522. In one approach, as shown in FIG. 12A, a driving shaft 524 can be used, with the pivotal point 520 sliding along it by means of a traveling guide 521. This shaft can freely rotate by means of bearings 526 and 528 anchored on a pole 530, which is attached to the base 108. The driving shaft is powered by a E-M transducer or a M-M link 532 connected to the shaft by means of a corner gearbox 534, if the axis 536 of the motor is perpendicular to the shaft 524. Alternatively, if the 536 and 524 are parallel a timing belt can be used or gears directly engaged. Aspects of this design can include: (a) the E-M transducer or a M-M link 532 can be placed on one side of the pole 530 so it does not obstruct the motion of the pivotal point 520; (b) the center of the pivotal point 520 may not be along the axis of the shaft but to one of its vertical sides. The later design would be adopted so that the interventional guide is not obstructed by the pole or the shaft. FIG. 12B illustrates another possible implementation for the pivotal point 520 actuator based on a telescopic pole. This mechanism can based on hydraulic power based on standard mechanisms available to those knowing hydraulic systems.

It should be mentioned that both approaches may implemented in such a way that the centerline of the IS, as for example indicated by the line 538 or 540, is not the same with the vertical line passing through the pivotal point, say 542 and 544. The lines 542 and 544 correspond to the position of the interventional probe. If such design is adopted, then this difference can be taken into account in the calculation of the stage 108 positioning, as described herein, so that at the final position of the stage IS the lines 542 and 544 pass thought the target point inside the breast.

FIGS. 12C and 12D illustrate diagrammatically the link-mechanism between the two pivotal points 546 and 548 (which correspond to points 138 or 140 of FIG. 3). The pivotal points are attached at the travel guides 550 and 552, which can slide along the poles 554 and 556. Furthermore, the pivotal points 546 and 548 can freely rotate by means, for example, of bearings 558 and 560. The pivotal mechanisms include two constructions 562 and 564 which are attached at the end of the pivotal axles 546 and 548 and serve as supports for the attachment of the interventional guide 566. One of the supports, say 562, preferentially the closest to the compression plate 104, has appropriate setup 568 for securely anchoring one of the ends, say 570, of the interventional guide 566, such as a bolded hole. The other support, say 564, has appropriate setup 572 so that the other end, say 574, of the IG 566 can slide. Such a mechanism can account for the fact that when the two pivotal points are set in any orientation but the horizontal (FIG. 9D) the distance between the pivotal points 546 and 548 changes along the axis defined by them, say line 576. This is in constant with the fact that the attachment points 570 and 574 of the IG 566 remain in a fixed distance. This is illustrated in FIGS. 12D, 12E and 12F, where the distance of the attachments points 570 and 574 remains the constant, while the angle relative to the horizontal θ is set to positive and negative keeping the pivotal points 546 and 548 along constant vertical axes 578 and 580.

Subject Stage:

The patient stage 52 is an elevated surface relative to the patient couch 58, accommodating the PD in that space so that it provides space for the PD to move and positioned appropriately as illustrated in FIG. 1. In generally the subject stage provides the means for the breasts to be exposed in the intermediate space when the subject lies at a prone position has an opening, which can accommodate or two openings for the breasts to enter in the area of operations.

Example Device Control Unit and Software (DCUS):

In general, the DCUS, the components that is consisted of, and their connections (like flow of data) can be described in terms of the particular tasks that each one performs and the sequence by which the tasks are executed. Several schemes can be implemented so that the system can operate according to the invention. An example of a DCUS is described in accordance with FIGS. 1 and 13. In this implementation, the DCUS is comprised of the Device Operation Manager (DOM) 590, the Device operations area Generator (DOAG) 592, the Motion controller manager (MCM) 594, an assembly of support components 596, an interface to the device 598 and an interface to the user 600. The DOM 590 is a central piece of software, which controls the flow of system operation as for example described in FIG. 14. The DOAG 592 is a piece of software, which generates a virtual representation of the area of operations, the Device Operations Area (DOA), to be presented to the user. In generally, the DOA is a virtual 3D space, which corresponds to the space in the MRI scanner where the intervention occurs and is used to concurrently present the MR images and the position of the device. The DOAG refreshes the screen presented to the user based on data furnished by the DOM 590 through a data link which is internal to the host unit. An example of the DOA is described in accordance with FIG. 15. The DOAG can be based on modified or non-modified standard libraries of software, or to new software developed for the particular application, according to the art known to the software engineers and programmers. The MCM 594 is an assembly of software pieces used for the computer-control of the motion controllers, and in generally provided by the manufacturers of the specific instrumentation used for controlled motion, such as stepper motors. The support components 596 can be comprised of software routines necessary for the operation of the operation of the DOM, according to the invention, and can include components, but not limited to, such as a safety module 602 and a tools module for image manipulation and control of the device 604. The tools can be such to assist the operator in controlling the device as described herein. Example of such tools and, their relation to the DOA, is described herein in accordance to FIG. 15.

The user to DCUS interface can be, for example, an appropriate graphics user interface (GUI) 600 which provides to the user the information required for the operation of the device.

Device Operation Manager (DOM): An example of a DOM is described in accordance with FIG. 14. The system is in generally at a Stand-By condition 630, ready to accept instruction from the user. When a new action 632 is initiated the DOM reads the particular commands 634, as for example, rotate to a specified angle θ, and calls the safety module 602 to evaluate the validity of the requested action 636. Such safety control may check, for example, the validity of the requested action in relation to the spatial constrains or exerted forces to the subject. However, several other safety test may be included according to the needs of the intervention. If the safety of the action is not valid the system can inform the user and goes to the stand-by condition 630. If the action is valid, then the DOM calls the DOAG 592, which builds a prospective view 638 of the DOA and the requested action is presented graphically on the screen 640. After the acceptance of the action by the user 642, the MCM 594 is recalled to calculate, at step 644, the particular instructions for the motion encoders 646. The DOM proceeds then to move the device according to the instructions performing a loop 648 over the pre-set by the operator number of motion steps. In generally any controlled motion of the device can be viewed as a single step, from a pre- to a post- position, or it can be divided in more than one step. The use of dividing to more than one step would be, for example, to correlate the motion of the device with real-time MRI imaging, in which case the DCUS triggers the MRI scanner to collect a predefine set of MRI images. If one step is chosen then there will be, in generally, collected two MRI images, one pre-motion and one post-motion. If n number of steps is chosen then there will be n+1 MRI images, one pre-action, one post action and n−1 in-between. Either way, the DCUS first determines the expected position of the markers and places then on the screen 650, for example with a graphic symbol. After the end of the motion (single step implementation) or after the end of a particular motion step 652, the DCUS sends a triggering signal 654 to the MRI scanner. This triggering can be a digital signal generated by the host computer according to the specifications of the particular MRI scanner. Subsequently, the DOAG is recalled to built the actual DOA based on the new MRI images 656, the position encoder information 658 and refreshes the screen 660, presented to the operator. During the motion loop, the operator can always intervene and abort the particular motion or reverse it bringing the system to a stand-by condition. Such feature of the invention is very important for cases of emergency. Furthermore, during the entire operation of the DCUS information can be recorded for purposes of evaluating the procedure, incurrances etc., by generating an internal log file 664 which can be stored to a data storage unit 668.

Figure 15A:
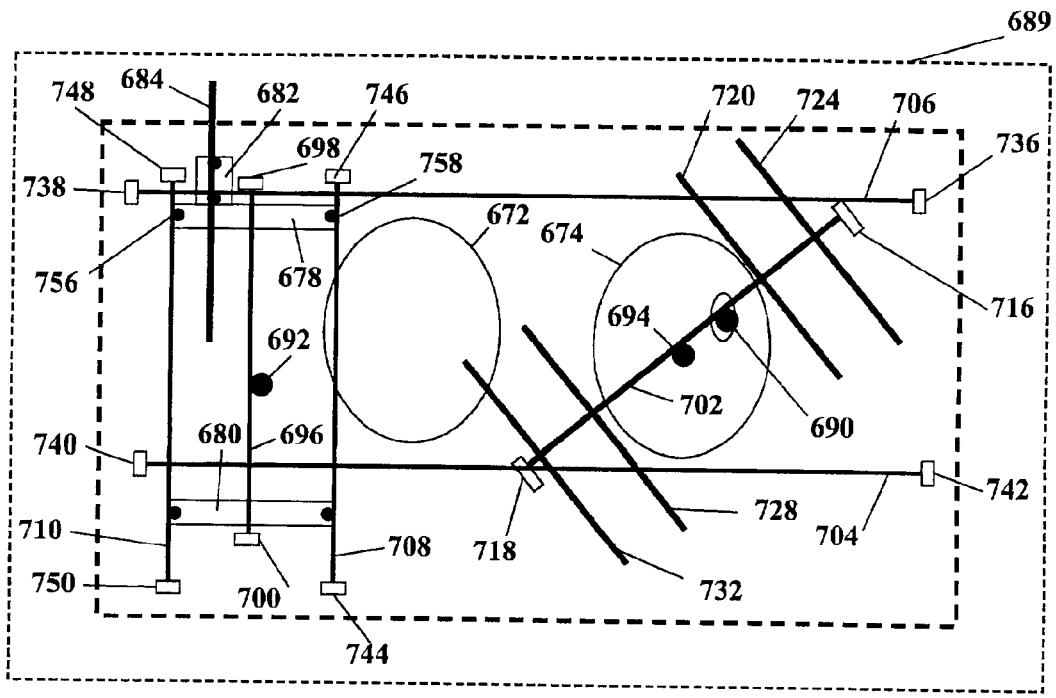
FIGS. 15A and B show a diagrammatic Example of a Device operation Area and tools available for planning an operation within the scope of the present invention.
Figure 15B:
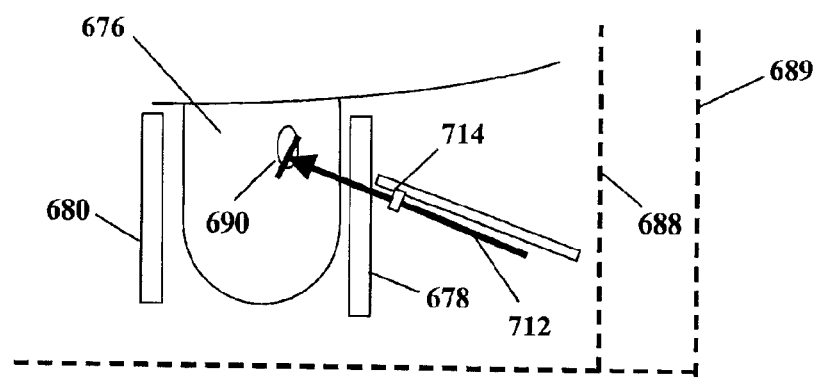

The Device Operations Area (DOA): An example of the DOA is described in accordance with FIG. 15. The DOA is a representation of the operations area, presented to the operator, preferentially with a comprehensive GUI. The DOA can provide information to the user, including MRI images, dimensions, and the manipulation tools. Preferentially, the DOA should present the actual MRI images, which are updated during the operation as new are collected. FIG. 15 shows possible appearances of the DOA depicting say a sagittal view (FIG. 15A) of the breasts 672 and 674, and a coronal view of one of the breasts 676 (FIG. 15B). In the particular example, it is shown the breast in the uncompressed state, and provide tools for the operator to plan the operation. Furthermore, in accordance with another aspect of the invention, the main components of the device can be graphically represented, such as the compression plates 678 and 680, the interventional stage 682, the line of the interventional guide 684, and the center of the plates rotation 696. Furthermore, the boundaries 688 of the FOV used for the collection of the images and the boundaries of the device operations area 689 can be also represented. In generally, the DOA preferentially shows the MRI images and the graphical objects with their actual relative dimensions. By this way there is a direct relationship between physical (actual) dimensions of the operation's area and the actual dimension of the apparatus and the MR images. This is achievable since any point and dimension in the DOA corresponds to a point and a dimension in the real space. A linear transformation matrix can be then used to transform coordinates, and thus object dimensions, from the real space to the DOA virtual space.

The MR images will be placed in the DOA. Furthermore, preferentially the DOA, including the MRI images, the graphical representation of the device and the tools, can be viewed as a 3D object so that the operator can chose any oblique orientation. 3D viewing of the DOA can be done according to the art known to computer programmers and software engineers. In accordance with another aspect of the invention, the DOA can be viewed on the standard console of the MRI scanner, for example by superimposing the aforelisted graphical objects to the MRI images, if the host computer for the DCUS is the MRI console.

Tools for planning the intervention (IPT): FIG. 15 shows a representation of an example DOA with the commented tools for manipulation. Several tools can be available to the user. Examples of such tools may categorized as target points, device rotation point/axis, and guidelines, and their position and orientation (guidelines) can be defined in the 3D space of the DOA by means of pointing devices controlled by keyboard, joystick, voice recognition or any combination of them. Such points can be, for example, presented as point-and-click buttons on the screen and can be recalled when required.

Target Points: This is a user defined point target which, in generally, is set on the target area, for example point 692. The target point can be associated with a guideline, such as the intervention trajectory or the insertion guideline and acts as a pivotal point for them.

Guidelines/Guide-Planes: Guidelines are objects of the DOA, represented by lines that are generated by the software and placed on the screen. In generally, they are used in order to guide particular steps in the positioning of the device or the intervention, or measure distances or other manipulations related to the need of the inventions and require a guideline. Particular guidelines may correspond to planes, since the particular aspect of the device associated with them is a plane, for example, the compression guidelines correspond to guide-planes since they are used to guide the compression plates A and B. As objects of the DOA, guidelines are defined as 3D lines by a general equation, and their length. Furthermore, limitations can be placed in the manipulation of their properties, such as their length, 3D orientation (e.g. be limited to a specific plane). In addition, guidelines are unambiguously defined in the real space of the MR scanner, through the transformation of the objects in the DOA to objects in the real space. Thus any manipulation of the position or length of a guideline can be transformed to the corresponding in the real space and thus result to a well-defined action, for example, moving an actuator. The relationship between the real and the DOA space provides the means of controlling the device by accurately calculating the appropriate commands for the motion of the actuators. Guidelines may equipped with calipers, rulers and other aids for assisting the operator to accurately define a particular action. Several types of Guidelines can be provided to the user and each one of them is associated with a particular action. For example, the intervention guideline (IGL) 702 is used to define the compression direction. The travel guidelines (TGL), like the x-travel guidelines (x-TGL) say 704 and 706 and the z-travel guidelines (z-TGL) 708 and 710, can be used to define the pathway of motion along a particular axis, X and Z respectively. Note that; although the design of the instrument presented herein suggests motion along the principle axis of the magnet (coordinate system R), an oblique direction of motion can be achieved by combining the motion along two orthogonal axes. The four guidelines used herein for the description of the invention are:

Intervention trajectory ($T_R$): The $T_R$ 712 is used to define the exact trajectory pathway for insertion of the interventional device, after the compression. In generally, like in the case of the IGL, the $T_R$ can be freely placed in the 3D space. Preferentially, it would have a pivotal point set on the target 690, and it can be moved by the operator by means of a pointing device motion perpendicular to the compression plate 678, in order to correct for displacement of the mass. In the specific case of the device described herein, the interventional stage 682 is always perpendicular to the compression plane 678. Thus, definition of the T point 690, defines automatically the projection of the $T_R$ 712 on the horizontal plane, since TR is the perpendicular from the target point 690 to the known plane of compression 678. The operator can perform fine adjustment of the $T_R$ line by translating it perpendicular to the compression plane. The TR has two calipers: one is placed on the target point 690 and the other one at the tip 714 of the retracted interventional probe, to define the depth of the intervention.

Insertion Guideline (IGL): IGL 702 is a guideline used to define the direction of compression. IGL is associated with the compression plates and with the device rotation point 694. IGL is set so that it passes through the target area as defined by the target point 690. To compress, the compression plates move along the direction defined by the IGL; thus they are always perpendicular to the IGL. Preferentially, the IGL appears after the definition of the target point 690 in the monitor. In generally, IGL can be manipulated on the 3D space. However, if the system is on the semi-automatic configuration, then the IGL can be freely rotated by the operator around a pivotal target point 690, on the $r_1$–$r_2$ plane. In generally, at this view the IGL is superimposed to the r1–r2 plane imaging slice used in the definition of that point. The IGL carries or has associated with it, four guidelines, the compression guidelines (CGL). After the definition of the device rotating point on the IGL, its length is regulated accordingly by the software so that it is equal to the length the compression plates can transverse, by means of calipers say 716 and 718.

Figure 18A:
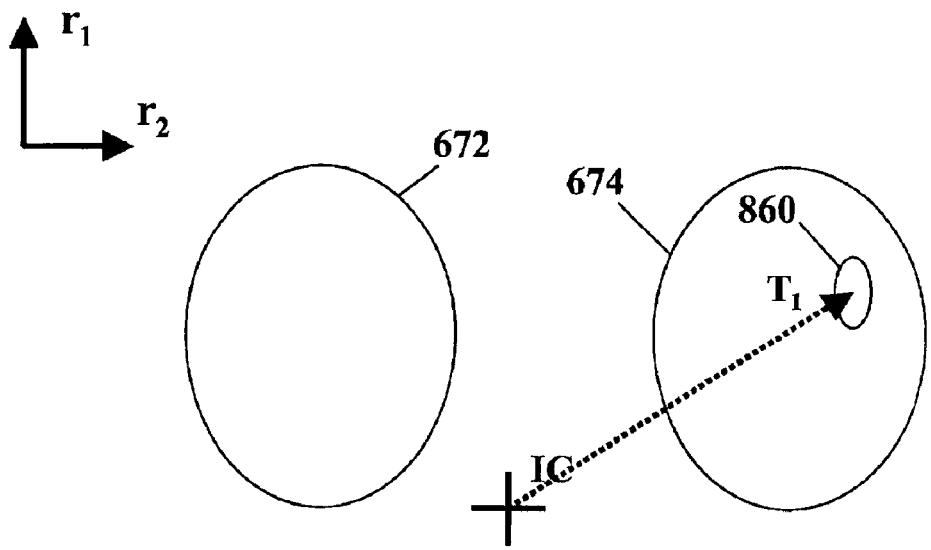
FIGS. 18A, B, C, D, E, F, G, H and I are illustrations of an operation planning and device operation (as in FIG. 17).
Figure 18B:
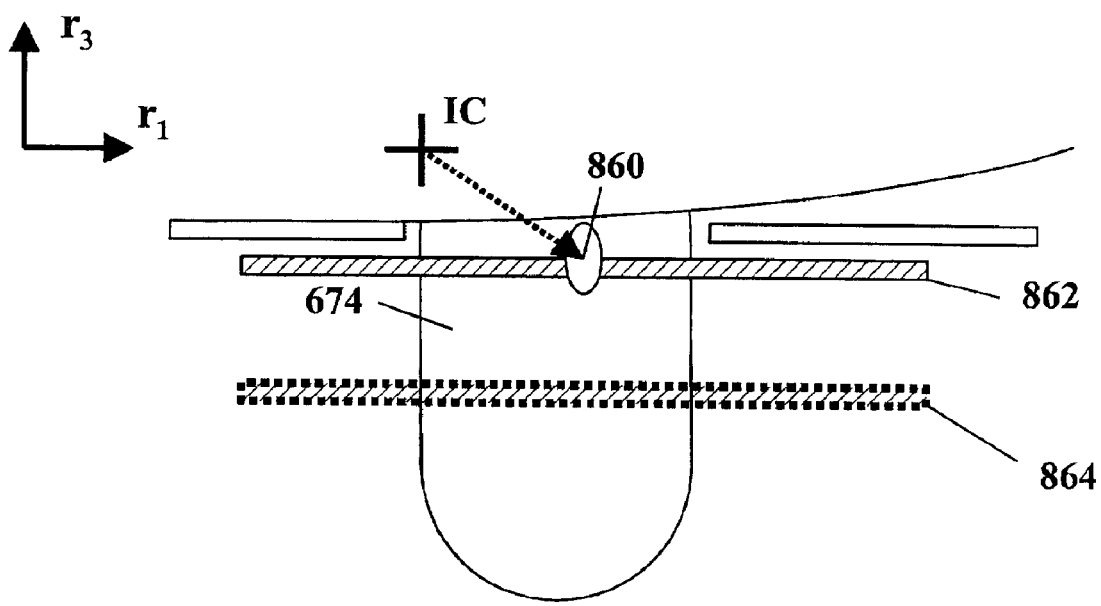
Figure 18C:
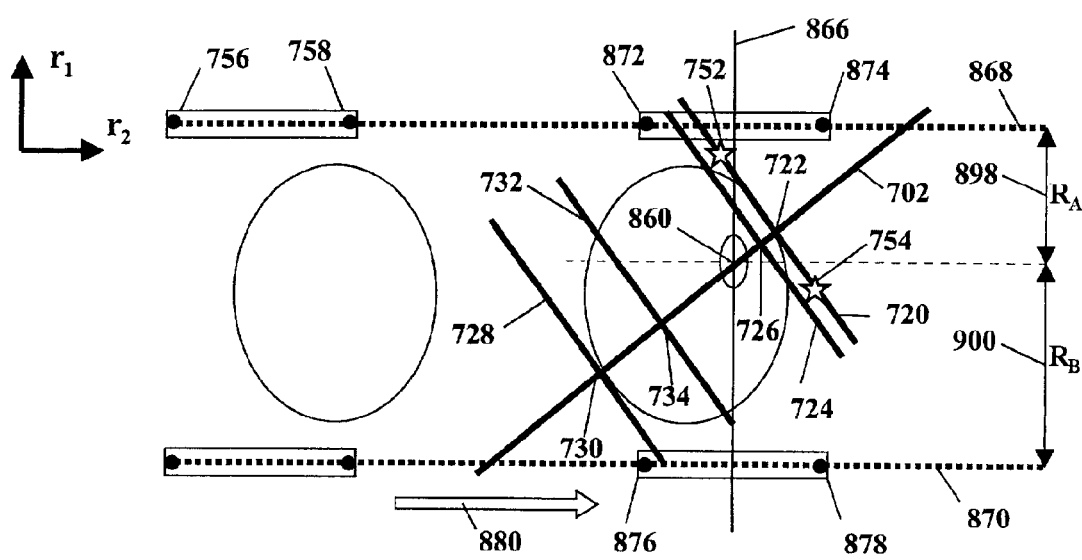
Figure 18D:
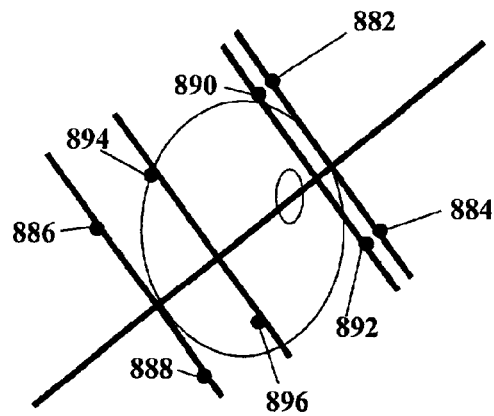
Figure 18E:
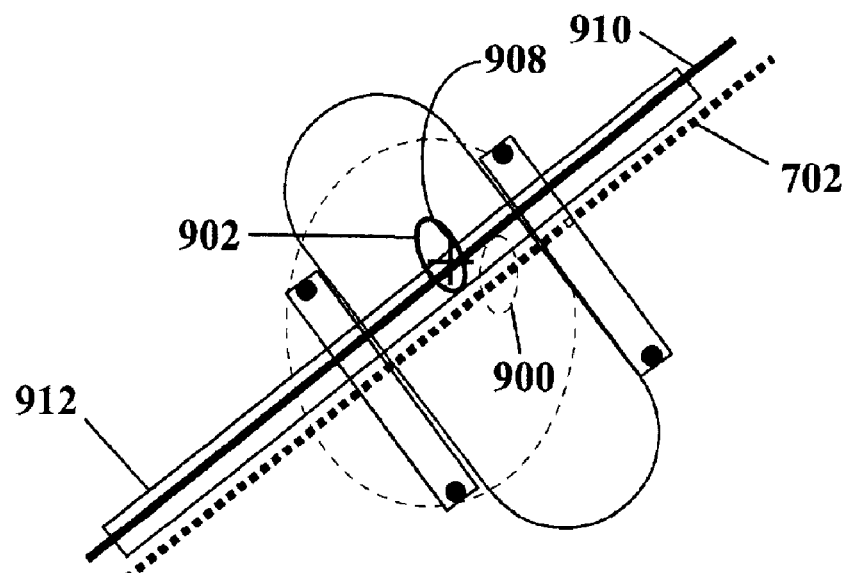
Figure 18F:
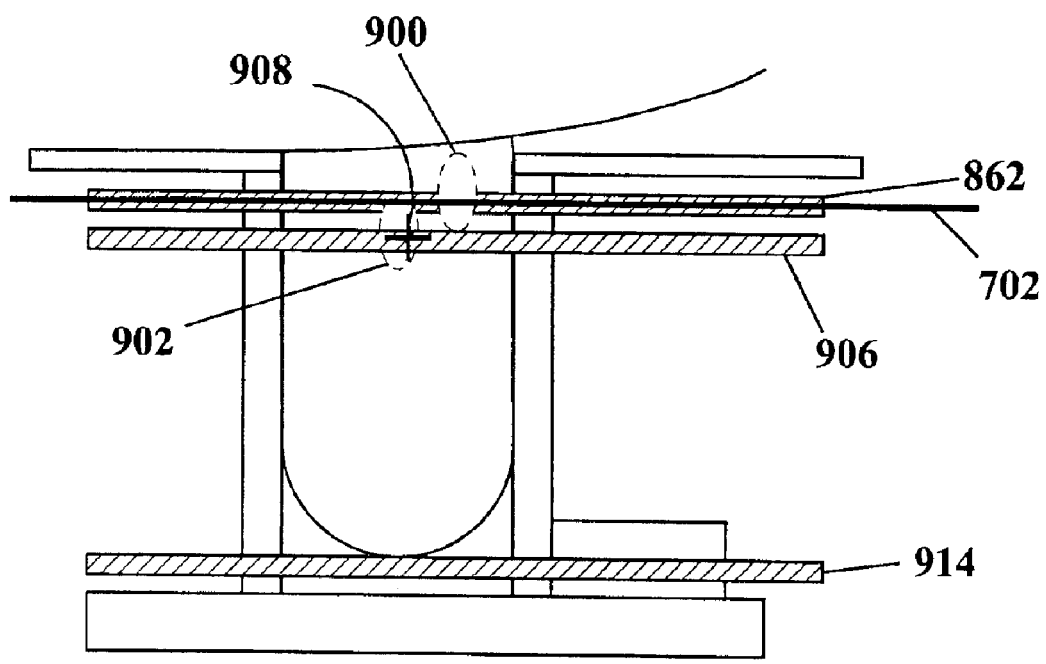
Figure 18G:
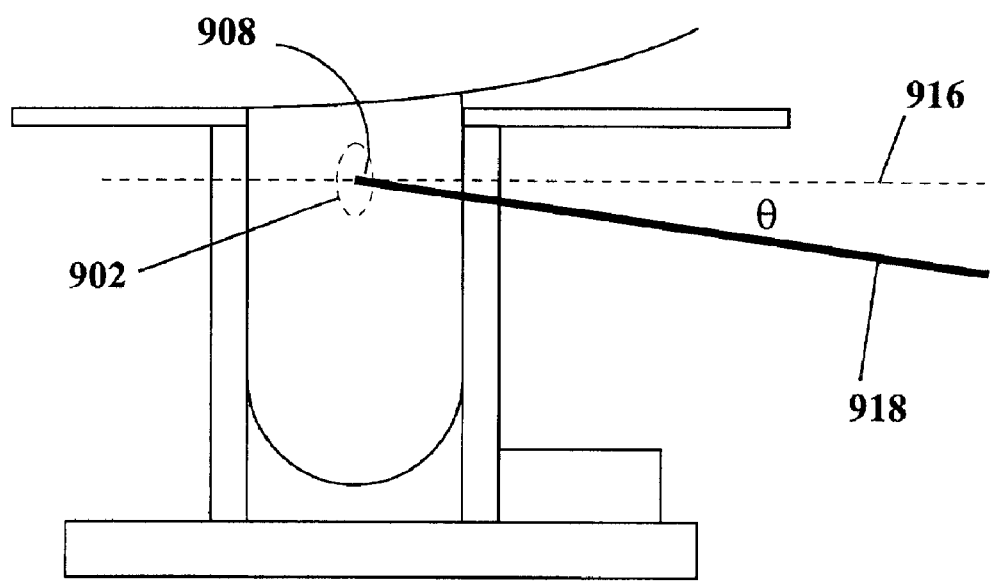
Figure 18H:
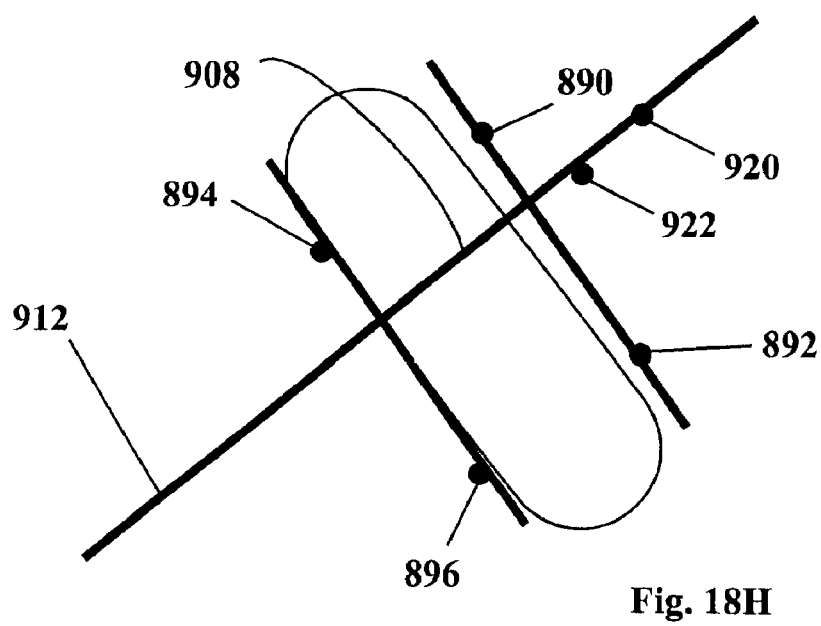
Figure 18I:
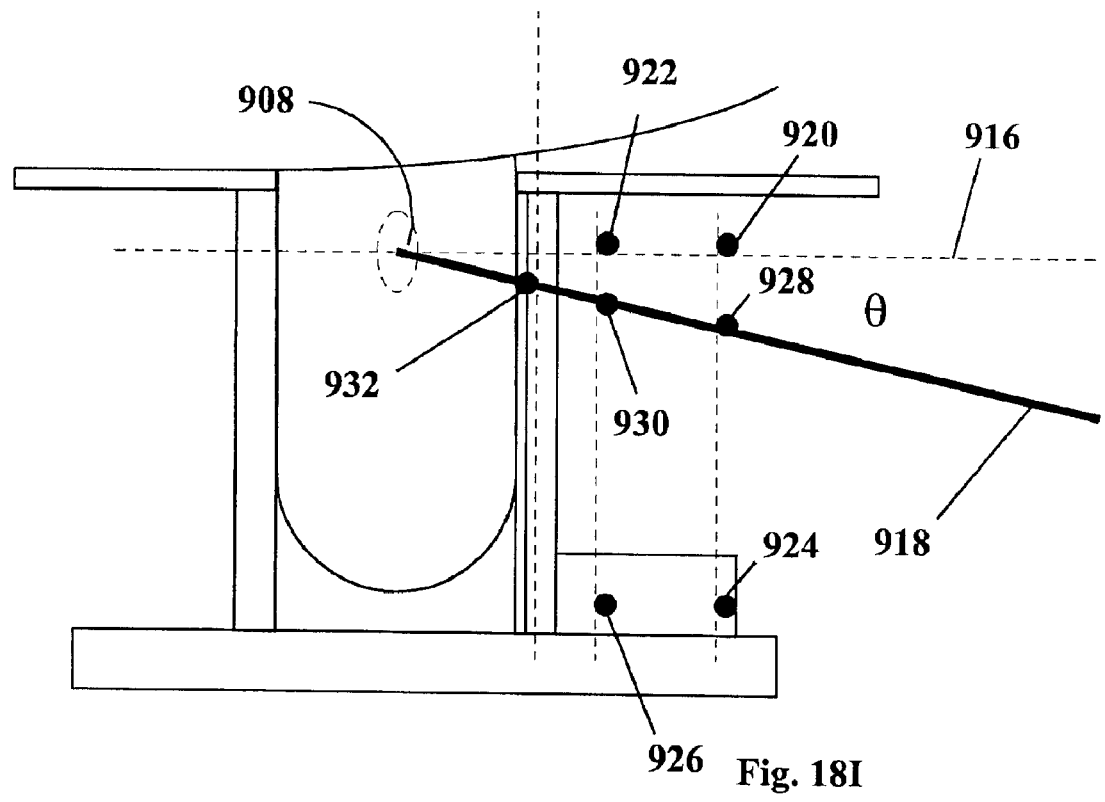

Compression Guidelines (CGL): The CGL are guidelines used to define the motion and the positions of the compression plates along the IGL; the degree of compression. For example, the CGL lines can be four in number and (a) they are placed by the software perpendicular to the IGL line, (b) the IGL pass through their middle, (c) their length is equal to the width of the compression plates 678 and 680 as transformed in the DOA space, (d) they can be positioned by the operator to any position along the IGL, however, they are limited by (i) the length of the rails, calipers 716 and 718, and (ii) cannot cross their paths. The CGL lines are:

CGL Line 1 720: Line of impact for compression plane 678 (the Gun side Plane). This is the line where the compression plate 678 will first touch or impact the breast surface (FIG. 18D). It represents the position of the compression plate A at the pre-compression stage. The intersection of the IGL and the CGL-1 line defines a point 722 with coordinates ($r_{I-A,1}, r_{I-A,2}, r_{I-A,3}$).

CGL Line 2 724: Line of compression level for plane A. This line indicates the final desired positions of the compression plate 678 (FIG. 18D). It represents the position of the compression plate A at the post-compression stage. The intersection of the IGL and the CGL-2 line defines a point 726 with coordinates ($r_{C-A,1}, r_{C-A,2}, r_{C-A,3}$).

CGL Line 3 728: Line of impact for the compression plane 680 (the back plate). This is the line where the compression plate 680 will first touch or impact the breast surface (FIG. 18D). It represents the position of the compression plate 680 at the pre-compression stage. The intersection of the IGL and the CGL-3 line defines a point 730 with coordinates ($r_{I-B,1}, r_{I-B,2}, r_{I-B,3}$).

CGL Line 4 732: Line of compression level for plane 680. This line indicates the final desired positions of the compression plate 680. It represents the position of the compression plate 680 at the post-compression stage. The intersection of the IGL and the CGL-4 line defines a point 734 with coordinates ($r_{C-B,1}, r_{C-B,2}, r_{C-B,3}$).

Travel Guidelines (TGL): The travel guidelines are used with the purpose to define a pathway for the motion of the device. They can be placed along the principle axis of the R coordinate system, and for example can be assigned as x-TGL or z-TGL if parallel to the r2 or r1 axis respectively. The TGL can be associated with the compression plates in order to place them from the original stand-by position to the pre-rotation position. The position of the TGL is limited by the travel lengths of the instrument at the corresponding axis, as for example by calipers 736 to 750. The TGL lines can be freely moved perpendicular to their plane, as for example the x-TGL 706 can be repositioned along the r1 axis, by means of a pointing device.

Checkpoints: A checkpoint is a coordinate in the 3D DOA space where a MR-visible marker attached to the device will reside after a particular motion, as for example a compression. Acquiring a MR image, which depicts a particular MRI-visible marker the position of the device can be verified. This can be accomplished by graphically representing the checkpoint on the screen of the scanner or on the screen of the DCUS, for example with a cross point. For example, the achievement of a desired rotation can be verified by using as checkpoints the positions of the MRI-visible markers at the edge of the compression plates. In particular, the position of the two markers of plate A after rotation, say 752 and 754 (FIG. 18D) can be unambiguously calculated in the R coordinate system, the coordinate system of the MRI scanner. A particular rotation can be verified as successful when markers are coinciding with the checkpoints on a MRI image acquired after the rotation. Furthermore, a path of the instrument motion can be constructed in the DCUS by knowing the speed of the motion and calculating the expected position of the device according to the image triggering rate. By this way, MRI can be used to accurate depict the device in real time. In generally, any number of checkpoints can be defined on the imaging plane, as long as they are on the pathway of the markers or inversely the device motion can go though these check points. These checkpoints can be calculated and set on the imaging screen to verify the position of the device. As an example of this process, such checkpoints can be set at the pre-rotation, pre-compression (or post-rotation) and at the post-compression phase.

Safety component: A piece of software, which is embedded in the DCUS, in order to perform several safety checks. Such checks can be, but not limited to, the device dimensions, i.e. if a particular requested motion fits within the design, The Safety component is called continuously during the flow in the DCUS and returns a feedback both to the software that it recalled from and to the operator, as for example by means of messages on a message screen window of the GUI.

Motion control and management component: This piece of software is the connection between the actuators and the control software. The later may, for example, be controlled by the software associated with the particular type of actuator and its control is known to the artisans of device control programming.

In another aspect of this inventions, the DCUS may include several other components, such as a data storage for continuous monitoring of the system performance by storing in some form of fast access data storage device, as for example, magnetic or optical storage media such as hard drive or a CD the device operation. This may include, data such as the commands delivered by the operator, like the positioning of the guidelines, the instructions delivered to the actuator drivers and the feedback from the encoders. This feature can be used for multiple purposes, such as educational, assessment of the surgery planning, system performance, and operator performance. Furthermore, the DCUS can include a testing and training component for the operator. In this case the system can perform every operation on a virtual target placed in the DOA.

The positioning of the device to deliver an intervention as described herein can be accomplished by several ways, which may categorized by the relative task effort of the operator and the device. In principle, since the device can be remotely controlled, a totally automatic approach can be adopted with the operator defining the compression plate, say 732 and 724, position and the trajectory 712. Furthermore, the operator can define any detail of the device motion and positioning using the DCUS and the provided tools, as for example described in FIG. 15. In generally, several combinations of such operation modes may exist, by setting the DCUS to perform several of the motions of tasks automatically.

Figure 16:
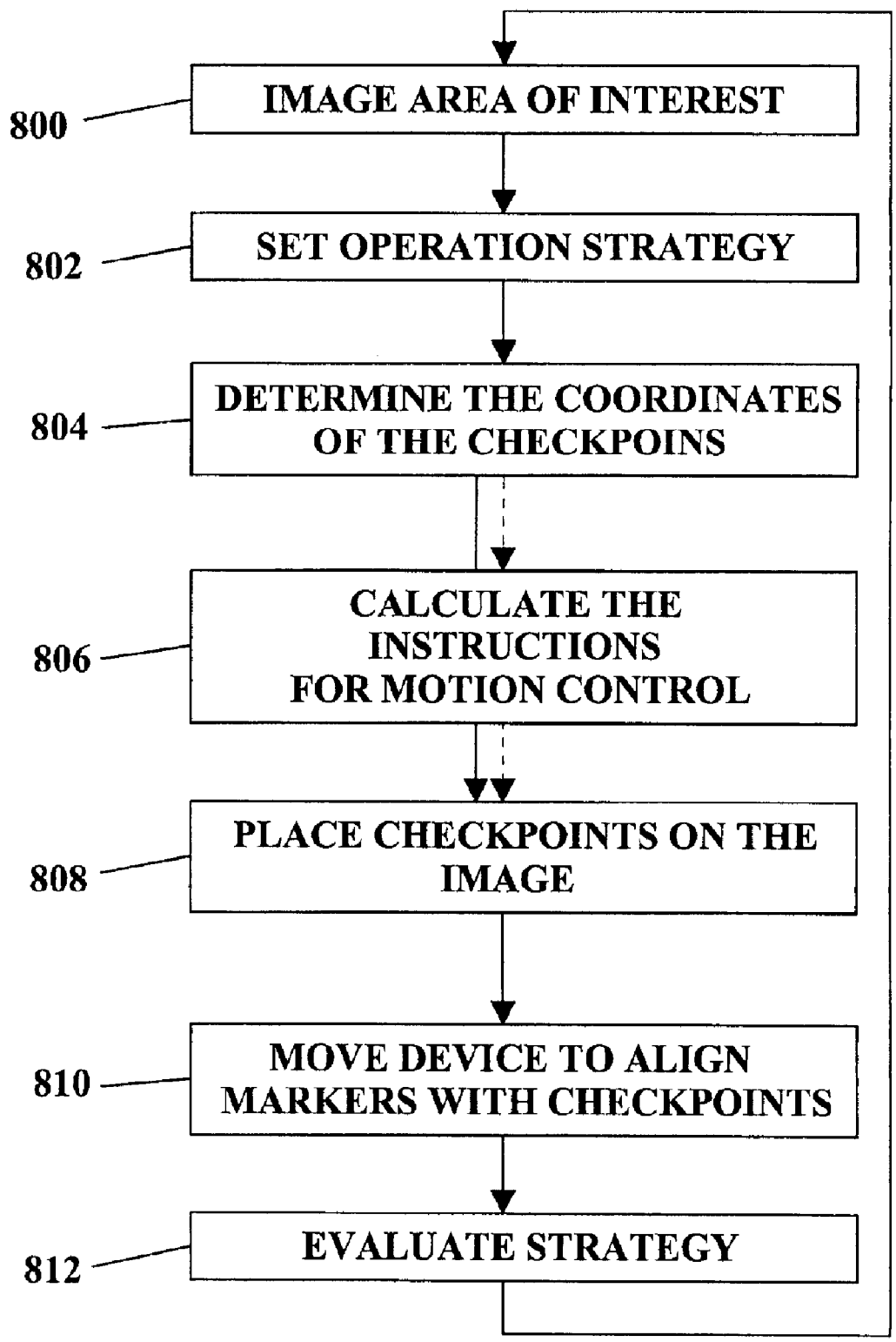
FIG. 16 shows a flow Block diagram of generic steps that may be used for operation of a device within the scope of the invention.

Independent of the mode of operation, the operation of the device based in the presented method can be overviewed in FIG. 16. It should be mentioned that the described steps, may or may not executed in this particular order, which can be dictated by other needs. The system operation can be described by the following stages, not necessarily performed in this particular order, (FIG. 16):

The area of interest is imaged 800. The employed orientations and methods of MRI image collection can be chosen on a case basis depending on the particular planes of interest, such as aligned with the interventional guide and the desired contrast, as for example with the infusion of contrast media A strategy for the operation is planned 802. Depending on the stage of the operation, this process can include the definition of the insertion guideline (angle φ) 702, the degree of compression with points 726 and 734, the rotation axis 694, the target 690 and the trajectory (angle θ and depth) 712. Determination of the checkpoints coordinates 804.

If the motion is automatically controlled and executed by the DCUS, then calculation of the device motion instructions 806. However, the system may be under total manual control, in which case this step may by-passed or used as a advisory to the operator.

The checkpoints, for example 752 and 754, are displayed on the images as the target points for the motion of the device 808.

The device is positioned, under the control of DCUS or the operator, to the targeted position and the positioning is verified 810 by means of aligning the MRI visible markers of the device, say 756 and 758, with the corresponding checkpoints, as for example 752 and 754. Imaging and valuation of the strategy 812.

Computer-Assisted Manual Control (CAMC) of the Device:

In brief, in the CAMC mode the operator has control of every aspect of the operation by defining the target point and the direction and degree of compression and the DCUS determines the control of the device motion based on the choices of the operator. Furthermore, the DCUS provides to the operator information regarding the operation, such as the position of the markers and tools for performing the planning and executing the operation, such as guidelines and rulers. In addition, DCUS performs checks of the validity of the choices of the operator regarding the spatial or operational limits of the system and informs the operator. In generally, the DCUS proceeds in a particular action only after verification of its safety and agreement by the operator. As in any other possible mode of operation of the device, the operator can quit the particular action, even while in progress, and reverse it.

Example of Device Operation in the CAMC mode:

An example of computer assisted operation of the device is described in accordance with FIGS. 16 and 18.

Pre-Rotation State: This is the state before the system rotates around the rotational axis R. In generally, to reach this state the system may perform the following motions:

Motion on the r1–r2 plane

Extension of the compression planes, i.e. motion of the planes along say the q2 axis, to facilitate easier maneuverability around and in relation to the breasts Rotation, non-related to the compression. Such rotations, in combination with the aforelisted (a) and (b) motions maybe required to place the device at the appropriate position. This type of motion is a composite motion.

Operator—Acquisition of a 3D or a Multislice Set of Diagnostic Images of the Breasts.

Operator—Set the target point ($T_1$; FIG. 18A) and DCUS—Calculate the target point coordinates: The target point $T_1$ 860 is identified and the coordinates, say $t_{1,1}$, $t_{1,3}$, and $t_{1,3}$, are calculated. For example, this can be accomplished by inspecting at least two MRI images corresponding to two orthogonal views from the 3D set, or the multislice stack. such as planes $r_1$–$r_2$ (FIG. 18A) and $r_1$–$r_3$ (FIG. 18B).

Operator (DCUS)—Define the monitoring slice(s) on the $r_1$–$r_2$ plane to monitor and verify the positioning of the device up to the stage of post-compression. This slice(s) should preferentially include the target point T 860, i.e. plane $t=t_{1,3}$ 862 so to better assess the device positioning and the compression process relative to the area of interest. The DCUS may automatically set this plane as the default one a plane or any other plane, say 864, or combination of planes, can be chosen. The MR-visible marker of the compression plates, say 166 and 162 in FIG. 4C, preferentially extends along the vertical length of the compression plate, thus, any slice would be suitable for monitoring the position of the compression planes as described herein.

Operator—Set the Insertion Guideline (IGL): After the marking of the target point 860, the IGL line 702 is displayed together with the CGL lines 720, 724, 734 and 728, superimposed to the MRI images. Initially the line can reside at a predetermined position 866, for example parallel to the r1 axis, in which case it can be described as: $r_2=t_{1,2}$. The operator rotates the IGL 702 around the pivotal point T1 860, in order to define the direction of compression, i.e. the angle $\phi$.

Operator—Set Compression Guidelines (CGL): The operator sets the desired degree of compression by sliding the CGL lines 720, 724, 734 and 728 along the IGL 702. The final crossing points $I_A$ 722, $C_A$ 726, $I_B$ 730 and $C_B$ 734 of the IGL and the CGL are determined.

Operator—Set Rotation axis (R): A rotation axis for the device is automatically set identical to the target point 860. However, the operator may define any other point in between the impact lines 722 and 728. Preferentially, and in order to center the interventional stage the rotation axis should reside along the IGL.

Operator—Set the travel guidelines along axis (TGL): The operator can further guide the motion of the device by setting the TGL. The placement of such guides along the $r_2$ axis 868 and 870 is illustrated in FIG. 17D.

DCUS—Calculation of the system pathway and instruction for the device actuator motion: The MCM component determines the instructions required to delivered at the drivers of the actuators to place the device at the post-compression state.

DCUS—Calculation of the Markers positions in the DOA at the checkpoints. For the particular case are calculated the coordinates of the compression plates MR-visible markers before the rotation, i.e. $T_{A-M1}$ 872 $T_{A-M2}$ 874 for plate A and $T_{B-M1}$ 876 $T_{B-M2}$ 878 for plate B. This points are target points for the markers verifying the end of the motion of the device along the TGL.

DCUS—Positioning of the Device to the Pre-Rotation state. After acceptance of the pathway by the operator, the motion is commenced as indicated by arrow 880. During the motion of the device, real-time MRI monitoring can be accomplished as described elsewhere in this document. For example, if real-time or motion-step-triggered MRI imaging is used then the position of the markers from their initial position, for example 756 and 758 for plate A and 757 and 759 for plate B, to their destination 872 and 874 for plate A and 876 and 878 for plate B. Furthermore, the GUI can provide further assistance for the verification of device motion in real-time by placing graphical objects, such as appropriately colored lines, on the calculated pathways of the device motions. In particular, for this motion, the pathway of the markers at the edge of the compression plates, which coincides with the TGL, can be presented.

Pre-Compression State: This is the state where the device has been aligned with the direction of compression, i.e. central axis of the device is aligned with the IGL. In generally, to reach this state the system may perform the following motions:

Rotation around the axis R composite motion consisted of rotations, motion of compression palates along the q2 axis and displacements along the r1–r2 plane in order to place the compression plates in alignment with the IGL. Such composite motion can be required with particular anatomies, such as when an enlarged breast forces the system to the limits of the available space for each motion.

DCUS—Calculation of the system rotation instruction for the device actuator motion: The MCM component determines the instructions required to delivered at the drivers of the actuators to place the device at the pre-compression state, i.e. to perform the rotation around the axis R.

DCUS—Calculation of the Markers positions in the DOA at the checkpoints. For the particular case are calculated the coordinates of the compression plates MR-visible markers after the rotation, i.e. $R_{A-M1}$ 882 $R_{A-M2}$ 884 for plate A and $R_{B-M1}$ 886, $R_{B-M2}$ 888 for plate B. These points are the verification checkpoints for the appearance of the markers after completion of the rotation of the device.

DCUS—Positioning of the Device to the Pre-Compression state. After acceptance of the rotation by the operator, the motion is commenced. During the rotation of the device, real-time MRI monitoring can be accomplished as described elsewhere in this invention. Furthermore, since each one of the marker points resides on a well defined cycle during rotation (radii $R_A$ and $R_B$), the GUI can present the corresponding arches that the markers will transverse together with the MR guide images as an additional verification.

Post-Compression State: This is the state after the compression, and after achievement of the desired pre-compression state is straightforward achievable by motion of the compression plates along the q2 axis, as for example one toward the other.

DCUS—Calculation of the system compression instruction for the device actuator motion: The MCM component determines the instructions required to delivered at the drivers of the actuators to place the device at the post-compression state.

DCUS—Calculation of the Markers positions in the DOA at the checkpoints. For the particular case are calculated the coordinates of the compression plates MR-visible after compression, i.e. $C_{A-M1}$ 890, $C_{A-M2}$ 892 for plate A and $C_{B-M1}$ 894 $C_{b-M2}$ 896 for plate B. These points are the verification checkpoints for the appearance of the markers after completion of the rotation of the device.

DCUS—Positioning of the Device to the Post-Compression state. After acceptance of the direction and degree of compression by the operator, the motion is commenced. During the compression of the device, real-time MRI monitoring can be accomplished as described elsewhere in this invention. Furthermore, since during compression each one of the marker points resides on a well defined line (radii $R_A$ 898 and $R_B$ 900), the GUI can present the corresponding lines that the markers will transverse together with the MR guide images as an additional verification.

Pre-Intervention State: This is the state immediately before the interventional probe is ready to be inserted in the breast, i.e. when the interventional guide is aligned with the $T_R$. In generally, to reach this state the system may perform the following motions:

Positioning of the interventional stage by motion along the q1 axis (fine adjustment of the $\theta$ angle alignment)

Angulation of the interventional guide, by means of moving along the pivotal points along the q3 axis.

This state can be redefined and repeated for the acquisition of a different target area.

Operator—Imaging for assessment of compression. Due to compression, the mass can be relocated from its initial position 900 to a new one 902 and in the general case this will occur on both the horizontal (FIG. 17A) and vertical view (FIG. 17B). As a consequence the IGL 702 and the monitoring plane 862 set in step 3, in generally, may not pass thought the targeted area.

Operator—Set the target point (T; FIG. 1A) and the Intervention

Trajectory ($T_R$) on the Horizontal plane: The new position of the target 902 is identified on a plane perpendicular to the compression plates. This can be accomplished, for example, by inspecting the views perpendicular to the compression plane, and isolating a slice 906, which passes through the targeted area 902. After the marking of the target point 908, the trajectory $T_R$ 910 is displayed, superimposed to the MRI images. The trajectory is defined as the line from the target point 908 to the compression plane, represented, for example, by the CGL 724. The operator can further adjust the trajectory 910 by translating it perpendicular to the compression plane 724.

DCUS and Operator—Define the device monitoring slices: This involves the definition of monitor MRI planes which can depict the motion and alignment of the interventional stage and the interventional guide:

DCUS: To monitor the angulation of the interventional guide, automatically define an oblique slice $P_T$ 912 which is perpendicular to the compression plate A, and passes from the target T 908. This can be accomplished by either acquiring a new set of imaging data, i.e. on the oblique plane 912 or by performing a multiplanar reconstruction of already obtained imaging data.

DCUS-Operator: To monitor the positioning and alignment of the interventional stage with the TR, the slice $P_T$ can be used. This slice however provides assessment of the stage only at its final position. For real-time monitoring of the position of the stage, it may required an imaging plane $P_I$ 914 parallel to the r1–r2 plane. This can be accomplished as follows: (I) if the stage has markers which extend to the entire height of the stage as described in accordance with FIG. 4D, then the slice 906 can be used or (ii) if such marker(s) is limited to a specific point of the device, as described in accordance with FIGS. 4E and 4F, then the monitoring plane will be places at the particular r3 coordinate of the marker(s) defining a new slice 906.

Operator—Set Intervention Trajectory ($T_R$) on the vertical Plane ($P_T$):

Description of a preferential presentation: The oblique MRI image corresponding to the plane $P_T$ 912 is displayed with the $T_R$ line at an initial orientation, for example, perpendicular 916 to the compression plane and having a pivotal point at the target T 908 point.

Operation: The operator sets the orientation of the $T_R$ by optical assessment of the image along the desired orientation, in an interactive process, for example by using a pointing device. The aim is to choose the optimal orientation 918, for the insertion of the interventional probe, as this is dictated by the particular anatomical and functional information known to the interventionist. This operation defines the angle θ_ between the $T_R$ and the horizontal plane (or equivalently, the axis $q_2$ and the $T_R$).

DCUS Support: During the interactive placement of the TR, the DCUS first checks the appropriateness of a vertical trajectory by using stored data regarding the dimensions of the interventional apparatus (e.g. space available underneath the table) and informs the operator for this accepting or not the chosen trajectory. Furthermore, taking in account the above spatial limitations it calculates the minimum angle θ. In addition, the GUI can present a graphical representation of the interventional probe to assist the operator to adjust the trajectory with real-time interactive representation.

DCUS—Calculation of the actuator driver instructions for the motion of the interventional stage (horizontal alignment with the trajectory): The MCM component determines the instructions required to be delivered at the drivers of the actuators to align the interventional stage with the $T_R$ (as viewed on the $P_I$ imaging plane 906 or 916).

DCUS—Calculation of the actuator driver instructions for the motion of the interventional guide (θ angulation): The MCM component determines the instructions required to be delivered at the drivers of the actuators to align the interventional guide with the $T_R$ (as viewed on the $P_T$ imaging plane 912).

DCUS—Calculation of the actuator driver instructions for setting the depth of insertion of the interventional probe: The MCM component determines the instructions required to be delivered at the drivers of the actuators to align the interventional guide with the $T_R$ (as viewed on the $P_T$ 912 imaging plane).

DCUS—Calculation of the Markers positions in the DOA at the checkpoints. For the particular case are calculated the coordinates of the MR-visible marker (s) of the interventional stage should reside after positioning, on the imaging plane ($P_I$). For example if the stage has the MR-visible marker arrangement illustrated in FIG. 4E then two checkpoints can be used, such as $GS_{P-M1}$ 920 and $GS_{P-M2}$ 922 using the imaging slice 906. If it is used the arrangement illustrated in FIG. 4F, then the checkpoints will be at 924 and 926. Furthermore, since during the positioning of the interventional stage, the markers should reside on a line parallel to the axis q1, the GUI can graphically present this line to verify the motion in real-time.

DCUS—Calculation of the Markers positions in the DOA at the checkpoints. For the particular case are calculated the coordinates of the MR-visible marker(s) of the interventional guide should reside after alignment, on the imaging plane ($P_T$) 912. In that case two checkpoints can identified the $G_{M1}$ 928 and $G_{M2}$ 930.

Commercial Application: The device is designed to (a) condition the breast, by setting the degree of compression and orientation, and (b) position an interventional probe along a specified trajectory chosen by the operator, with MR guidance. These tasks can be performed while the patient remains inside the MRI scanner providing high reliability and reduced overall time of the operation. The device will be adaptable to accommodate the instrumentation for performing a variety of trans-cannula or subcutaneous operations in the breast. As discussed herein, the apparatus has commercial applications for sites that perform diagnostic or therapeutic trans-cannula or subcutaneous procedures in the breast with MR-guidance.

The invention allows for the use of a universal positioning technology and associated devices that are appropriate to the accommodation of instrumentation for current and future developments in the field of MR-guided interventions in the breast. The device is fitted with sufficient degrees of freedom to provide high flexibility to access a target inside a breast with a variety of probes by any trajectory and orientation of compression, which better suits the particular interventional procedure. Table I summarizes the various features that are available or optional within the described device, their implementation and their advantages.

TABLE I

Overview of System Features, Means of their Implementation and Advantages in their application:

| Feature: | Implementation: | Advantage: |
| --- | --- | --- |
| High Target Accessibility | Orientation and degree of Compression Height and angulation of Probe Stage. | Access to any target with a trajectory optimal for the particular patient case or the chosen interventional device or technique. |
| MRI Guidance | MR-visible markers [on the Compression | Verification of the motion of the device Verification of the |

TABLE I-continued

Overview of System Features, Means of their Implementation and Advantages in their application:

| Feature: | Implementation: | Advantage: |
|---|---|---|
| | plates Positioning Stage and Probe Guide] | trajectory before patient removal Continuous monitoring for automated operation. |
| High Spatial Resolution | System design with hydraulic actuator | Better access to small and multi-foci masses appropriate for particular trans-cannula operations |
| Remote Control | Computer controlled hydraulic network | Facilitate the high accessibility with MRI guidance patient remains in the scanner until the device has fully aligned with the desired trajectory |
| Versatile Probe Guide | Mechanical link with interchangeable interfaces customized per accessory | Use of different interventional probes currently available or to be offered in the future. |
| MR scanner compatibility | Customized device base device dimensions | Use with the commercially available magnet design no need for specific in-site calibrations |
| Optional MR- or visually guided probe handling | MR guided placement of Probe GuideMR or Visually guided insertion and handling of the interventional probe | Visual for conventional interventional practices MR-guided for current or future interventions that may require such an approach (e.g. laser ablation) |
| RF Coil | Quadrature Detection variable separation of planar elements | Increased sensitivity |

Improved breast cancer patient management is a major societal issue that is receiving growing national attention. Breast cancer patients are requesting efficient diagnosis and care, as well as solutions with better cosmetic and psychological impact. The proposed apparatus is designed to support minimally invasive MR-guided interventions in the breast. The market for this system is strongly associated with the use of breast MRI. Currently, a group candidate for breast MR are women with radio-opaque breasts, for example due to post-operative scar or with augmentation implants. The commercial opportunity for the proposed device is associated with sites that perform breast MRI and breast MR-guided interventions on this population. The commercial opportunities for such device, domestic and international, will increase if breast MRI is proved to be an effective modality in detecting and characterizing breast cancer and will be further expanded if breast conserving therapeutic approaches, which require monitoring of tissue contrast, will be adopted. Based on our preliminary market research, a conservative estimate of the market can be related to private or free-standing women health centers (about 400 in the U.S.) which can refer patients to MRI sites or radiology departments, which perform breast biopsies. Other possible sites are government women health sites (such as the Veteran Affairs Medical Centers and Armed Forces), universities and radiology practices. The referral basis can be general practitioners or gynecologists and the users can be radiologists, interventional radiologists or surgeons. Furthermore, the proposed apparatus may better facilitate minimally invasive operations in the breast. Such operations are associated with minimal scars, faster recovery and better cosmetic effects, issues of major psychological and societal importance for the breast cancer patients, their families and the society in general. Both the niche market for the apparatus and its societal impact justify its development.

Due to the wide range of breast and chest anatomies (size and shape) and positions of the target areas inside the breasts, optimal planning of an interventional procedure may require appropriate conditioning of the breast, i.e. compression, and choice of the trajectory of the intervention, i.e. path of insertion. Oblique orientation of compression, as compared to standard medial-lateral or posterior-anterior orientations, and oblique trajectory, as compared to trajectories perpendicular to the compression plane, are better operation strategies for several cases. In particular, such flexibility in accessing the target is pivotal in order to transverse the shortest distance of tissue, and to reach areas of limited accessibility, like those close to the chest wall, the axilla tail and behind the nipple. Furthermore, appropriate conditioning of the breast with oblique compression can be useful in relocating augmentation implants at the best positions for access to a mass. Current MRI compatible biopsy systems employ plates with a mesh of holes to direct the biopsy needles and, thus, the trajectory is perpendicular to the compression plate with very limited free-hand angulation. Other designs, which use hemispherical guides to position a biopsy gun, require transversing a long path inside the breast to reach a target close to the chest wall, or opposite site to the point of entrance. Variable orientation of the compression planes is currently offered with the x-ray stereotactic tables (e.g. Fischer Imaging Co). Also, an MR biopsy system can in principle provide oblique compression with a Velcro surface to anchor the device at variable angles. The applicant hypothesizes that such a device can provide sufficient degrees of freedom to condition the breast and place an appropriate trajectory will be better suited for the current and future MR-guided interventions in the breast.

As shown in FIG. 2, the proposed device will provide sufficient degrees of freedom to condition the breast and set an appropriate trajectory. First, the compression plates can be rotated around any axis such as around the vertical axis ($q_3$) defining the orientation of compression (angle f). Then, the breast can be compressed from an uncompressed shape (78) to compressed one (76), by moving a mobile compression plate from an extended position (90) to the compressed one (80) by a distance L. Finally, the trajectory (74) can be set by means of adjusting the height (H) of a pivotal point (for example, relative to the patient couch) and the angulation (q) relative to the horizontal. A depth mechanism can be added on this design.

The use of an automated device provides a number of degrees of freedom to facilitate planning and performing an intervention. For better exploitation and utilization of the features of the system, MR guidance and remote control are important. First, the effect of conditioning the breast should be directly viewable, for example to assess the relocation of the targeted area as well as other structures of interest, like implants. Second, remote control can provide the ability to perform multiple adjustments of orientation and degrees of compressions to achieve the best orientation and positioning of the targeted area. Combining real-time MR imaging with remote control, these procedures can be done in a short period of time, a few minutes, within the contrast window provided by contrast materials. The alternative, manual adjustments, would require removal of the patient from the scanner, adjustment and re-imaging, most probably with an additional injection. Third, combining remote control with real-time imaging and MR-visible markers, the trajectory of the system can be accurately set and verified during the contrast window. Fourth, remote control and real-time MR imaging will provide faster positioning adjustment of probes for trans-cannula operations. Furthermore, remote control will allow all the tasks related to setting the operation strategy (e.g. f, L, q, H D) to be performed while the patient is inside the scanner and during a single administration of a contrast agent. Although a remote controlled device is associated with technical complications, several computer-controlled apparatuses with FDA approval are used, such as the motorized computer controlled stereotactic biopsy devices (e.g. Fischer Imaging Co. and Trex Medical Co.) and surgery assisting apparatuses (e.g., AESOP and ZEUS by Computer Motion Inc., Robodoc by Integrated Surgical Systems).

A particular, but only exemplary and non-limiting computer controlled hydraulic network can be used to drive the motion actuators of the device.

Alternative drives are air drives and other pneumatic systems, magnetic drives, screw drives, piston drives, and any other mechanical or electrical system that can be remotely controlled (or even manually, but externally controlled without the necessity of removing a patient from the MRI filed. Also, the device will usually be provided with several appropriately placed MR visible markers. With this approach, the performance of the device and the results of its operation can be directly viewed and verified (operation protocol). Checkpoints, i.e., graphical objects, can be placed on the MR images by the operator, or automatically by the software, depicting the MR-visible markers at the final position after the desired motion. Verification of the device motion can be then accomplished by checking the alignment of the checkpoints with the MR-visible markers; this can be used with either manual or automatic control of the device. Furthermore, if additional adjustments are required after the cessation of a first contrast period, then the system can display one of the images collected during the infusion of the contrast agent, which depicts the compressed breast, to perform these adjustments without a second infusion.

Device Spatial Resolution and Accuracy in Placing the Probe:

In one embodiment, the spatial resolution of the diagnostic MR images ranges from about 0.2 to 10 mm, for example from about 0.5 to 1.6 mm, or even less as higher resolution screen and focusing systems become available. Accuracy in an intervention is important for placement of markers, access to small and multi-foci masses, and monitoring the effect of therapeutic interventions. For example, accurate definition of the high temperature area during localized hyperthermia is important for irradiation of a cancerous area and to prevent destruction of healthy tissue. Although MR images of interventional probes demonstrate a few mm image artifacts around the probe itself, new probes are expected to be developed which generate less artifacts (e.g. DAUM Co. Chicago, Ill.). The alternative "mesh" approach possesses spatial limitations and limits the diameter of the employed instrument.

Inventive Approach: High spatial resolution is in the design of the device. This originates from the fact that the motion of the device components occurs in a "continuous fashion", for example, due to the combined use of computer controlled hydraulic linear actuators.

MR or Visual Guided Intervention:

Conventional interventional operations might require direct visual observation of the final stage of the operation, i.e., the delivery of intervention. An exemplary approach to this aspect comprises, after setting the operation strategy (angle ϕ, orientation and degree of breast compression, and pathway angle θ and depth D of interventional probe insertion) with direct MR-guidance, the intervention can be performed either outside the MR scanner, for direct visual inspection of the procedure, or inside the MRI scanner, for MR-guided procedure. This would remain the choice of the person performing the operation depending on the particular circumstances, the probe used and the practice of the intervention.

Versatile Platform for a Variety of MR-guided Interventions:

Currently, several techniques and corresponding instrumentations are used for the extraction of tissue from the breast. Novel approaches are expected to be developed which may be used clinically for trans-cannula operations, such as laser ablation, localized hyperthermia, localized delivery of medication or site markers and cryoablation. MRI is suitable to monitor such interventions since it (a) can be used to accurately position these probes and (b) offers a plethora of contrast mechanisms for real-time monitoring of their operation. For example, a remote controlled MR compatible system has been developed for localized hyperthermia applications. The present system will provide the remote control mechanism and degrees of freedom required for both external and trans-cannula operations.

This can be accomplished by adopting the "universal positioning device" approach, i.e., a platform that can be machined to allow attachment of an array of interventional devices (e.g., by the provision of holes, guide tubes, catheters, guide supports, and the like). Adaptation of the apparatus platform (such as 33 in FIG. 3 or 566 in FIG. 12D) for a particular device is a straightforward engineering and machining task. The success of the device will originate from its versatile maneuverability and adaptation to the operation of a particular interventional probe. For example, apparatuses for subcutaneous tissue removal, like vacuum assisted Mamotome (Biopsys Medical Inc), are better used if angulation relative to the compression plane is available under direct MRI viewing; such a feature can better facilitate the extraction of tissue close to the chest wall.

Specialized coils that better fit a particular anatomy or task are beneficial for improved sensitivity of signal detection. Fulfillment of the aim of achieving optimal access to the breast determines the design of the apparatus that, in turn, dictates the design of the RF coil. A quadrature RF coil is an example of a relatively conventional coil that may be used in this system.

Compatibility of the Apparatus with Current Scanners:

The device should be able to operate inside any MRI scanner without special modifications.

The apparatus has been designed to fit in a standard commercial cylindrical MR scanner, with dimensions appropriate to fit in the space underneath the subject stage of the commercial RF coils offered for breast imaging at the prone position as described herein. Minor physical modifications of the apparatus anchoring mechanism may be required, to be used with a given scanner model.

Design Materials and Methods for the Construction of the Positioning Apparatus:

The apparatus is preferably designed for procedures with the subject lying prone on an elevated patient stage (PS) placed onto the MRI couch (MC). The patient stage will have appropriate openings (OP1 and OP2) for the breasts (BR$_1$ and BR$_2$) to be disposed underneath it. The device (DEV) will be anchored onto the lower surface of the PS. Two anchoring positions can be offered for access to either of the breasts. The system is composed of (a) a positioning device with a set of suitable hydraulic or mechanical actuators, (c) software for planning the operation and controlling the device and (d) it may be fitted with an RF coil. With this device, the operator can (a) condition the breast to a desired orientation (angle theta) and degree of compression (L) and (b) align a probe guide with a trajectory (location and angle). The operator can then remove the patient from the MRI scanner and proceed with the intervention having visual access by attaching an interventional device on the probe guide. Alternatively, the operator can use an MRI-compatible interventional device for real-time MR-guided surgical operation.

In one embodiment, the positioning device is comprised of (a) a base (B), (b) two compression plates ($CP_1$) and ($CP_2$), (c) a stage (S) for attaching the probe guide, (d) probe guide (PG), (e) a number of hydraulic or mechanical motion actuators, and maybe an RF coil assembly.

Base (B) and Compression Plates (CP1 and CP2): In one embodiment, the base includes two horizontal plates. The lower plate ($BP_1$) will be anchored on the PS. The upper plate ($BP_2$) could rotate relative to the $BP_1$ about the vertical axis (1), by means of a gear ($G_1$), which will take motion from a hydraulic actuator ($HA_1$), through a timing belt ($T_1$). This rotation will set the angle. The $BP_2$ will also carry the compression plates ($CP_1$ and $CP_2$). The solid stationary plate ($CP_1$) will be permanently attached on the base to provide the back-support for the compression of the breast and it will carry the Figure "8". The other plate will be movable (2), so the distance between the two plates can be adjusted to the desired degree of compression L. The mechanism for moving the plate $CP_2$ will include two rails ($R_1$ and $R_2$) anchored on the base plate $BP_2$, and four computer controlled hydraulic pistons ($HP_1$ to $HP_4$). The $CP_2$ plate will have a window opening (W) for unobstructed access to the breast and will carry the single-loop coil. A plastic sheet, penetrable by the intervention instrumentation, will be used in front of the window to support the breast.

Stage (S): The stage S will provide the means for placing the probe guide (PG) at any coordinate in the window (W). The stage will reside on an extension of the $CP_2$ plate, which will also carry the mechanism for the motion of the stage. With this approach, the plate $CP_2$ and the stage can move together as a single piece during compression along the rails $RL_1$ and $RL_2$ (motion (2)).

For positioning along the horizontal axis (motion (3) on the oblique X or Z axis), the stage could slide on along three rails $RL_3$, $RL_4$ and $RL_5$ by means of an actuator $HA_2$ that will drive the stage with a timing belt $T_2$. Rails $RL_3$ and $RL_4$ will be at the lower edge of the pole (PL); the third $RL_5$ will be attached at the upper edge of $CP_2$ for additional stabilization and guidance of the stage. For positioning along the vertical axis (motion (4)), the pole (PL) will have a linear actuator for motion along its length and thus adjustment of the height (H).

Probe Guide (PG): The probe guide is the base for attaching the particular interventional probe necessary for the chosen procedure. The probe guide will be movable along the vertical pole (PL) of the stage by means of an actuator $HA_3$ and a timing belt (not shown). This motion will define the height H. Furthermore, the PG will be attached to a moving guide on the pole (PL) by means of a mechanical link, which will serve as a pivotal point. A smaller version of the actuator will be used in order to rotate the PG around that pivotal point in order to align the probe guide with the trajectory on a vertical plane; i.e. set the angle ((motion (5)). The hydraulic actuator will be a horizontal structure to accommodate the two pistons illustrated in the design. The timing belt of the actuator will directly drive a gear attached to the bearing of the probe guide, in order to facilitate rotation. The probe guide will have a mechanical link for attaching the used interventional probe. This mechanical link will have interchangeable interfaces appropriate for particular interventional probes. For example, if the intervention is the insertion of a localization wire, then this interface can be a sterile bushing. A depth regulation mechanism can be also implemented and as well as localized breast compression for increased stability of the area of the breast.

MR Visible Markers: Long tube-like capsules, embedded markings, adhered strips, or other MR-Visible markers or markings will be placed along the vertical edges of the compression plates, to identify their position relative to the breast and on the pole of the stage (FIG. 6) to identify the position of the compression plates and the stage, respectively. With this arrangement, any coronal imaging plane can image the position of both the compression plane and the probe stage. Second, two markers will be placed, one in the front and one in the back edge of the probe guide. With this arrangement, an oblique plane that is perpendicular to the compression plane, and passes from the stage, can be used to monitor angulation and the alignment of the probe with the trajectory.

Dimensions of the Device: The proposed apparatus will have a height equal to this of the standard commercially available breast RF coils for imaging on a prone position. If a woman its to be imaged with a commercial RF coil, then it will fit in the scanner with the proposed apparatus. Thus, its use will not limit the number of women that they can be currently imaged with a standard MR scanner. Exemplary, but not limiting dimensions of the device will be: height of base 1–4 cm, e.g., 2 cm; height of plates 8–16 cm, e.g., 10–12 cm (total height of the device is 9–20 cm, e.g., 12–14 cm); width of plates 16–24 cm, e.g., 18–20 cm; length of compression rails (maximum opening) 12–20 cm, e.g., 14–16 cm; width of stage 4–8 cm, e.g., 6 cm, thickness of wooden patient stage about 0.5 to 2 cm, e.g., 1 cm. These dimensions are similar to those used in other MR compatible devices. And to commercially available RF coils. Thus, the device will not limit the number of women that can be imaged and be subject to breast MRI.

Sterilization and Safety Procedures: A suitable sterilization process for such a system will include washing with hot water and disinfecting with alcohol. Furthermore, commercially available (BIP Corp) thin walled sterile aluminum bushings will be used on the tip of the probe guide for 14–20 gauge needles. A manual safety valve can be placed near the operator to be used for quick release of the compression and placement of the compression plates to the maximum extension.

Motion Control and Linear Hydraulic Motion Actuators:

In one embodiment of the device, all the moving components will operate by means of mechanical or electrical or hydraulic power. As an example, for the operation of the motion actuators (MA) inside the MR scanner, computer controlled step-motors (SM) will be used to drive pistons ($PI_o$), located outside the magnet, to deliver accurate controlled hydraulic pressure to pistons ($PI_i$), inside the MRI scanner. The pistons $PI_i$ will be part of the motion actuators (MA) used to control the motion of particular device components (DC). Tubing (Tu), of sufficient length, will connect the pistons outside with those inside the MR scanner. As an example, the total number of five step motors will be used: rotation, compression, and two linear motions of the stage and angulation. The step-motors will be located outside the MRI scanner, so their operation will not be affected by the magnetic field or impose any hazard for the patient or the support personnel. For the compression plates, the hydraulic power delivered to the device will be split in four pistons. Standard hydraulic pistons are not suitable for controlling the motion of the proposed device inside an MR scanner because they require installation space, which is twice the length of stroke. To address this issue, a hydraulic actuator will be used in the device: (a) two pistons are used for unidirectional motion and braking, (b) the stroke of the pistons ($P_1$ and $P_2$) is almost equal to the length of the tubes, and (c) there is no axle but a timing belt (TB). The two pistons receive hydraulic pressures of opposite directions, to move the timing belt TB to both directions and to serve as a brake system. A component (C) of the device can be attached at the middle of the TB. Gears $G_1$ and $G_2$ with suitable radii can be appropriately placed to facilitate a desired motion: linear if the component is attached to the belt, or rotational if it is attached to a gear. Outside the MR scanner, each step motor (SM) will drive two pistons in opposite directions by means of a gear to deliver hydraulic power to the two pistons of the actuator inside the scanner.

Materials:

All the components of the apparatus inside the scanner should be non-magnetic, although elements that can be removed from the immediate operational field or that are moved by magnetic stereotaxis, or have magnetic markers may be movable within the field (that is, at least temporarily within the scanner, or permanently within the scanner were the magnetic strength is sufficiently small as to not too significantly interfere the performance of the MRI system. Perspex or polymeric materials, especially polyvinyl chloride (PVC) may be used for the construction of components such as the base, the compression plates, the stage, the probe guide and the actuators. The shafts and gears may be constructed of such non-magnetically influenced materials such as aluminum, brass or Delrin, in case that plastics cannot provide the strength and precise fabrication required for these components. Elastic timing belts can be used on the motion actuators. Polyether ether ketone (PEEK) resin, for example, can be used for the bonding screws and ceramics for bearings. The MR visible markers will be capsules filled with the oily fluid nitroglycerol. An environmentally safe preferentially oil-based and non-compressible hydraulic fluid will be used. Standard off-the-shelf components will be used for feeding screws, bearings and pistons for parts outside the MRI scanner.

Figure 17:
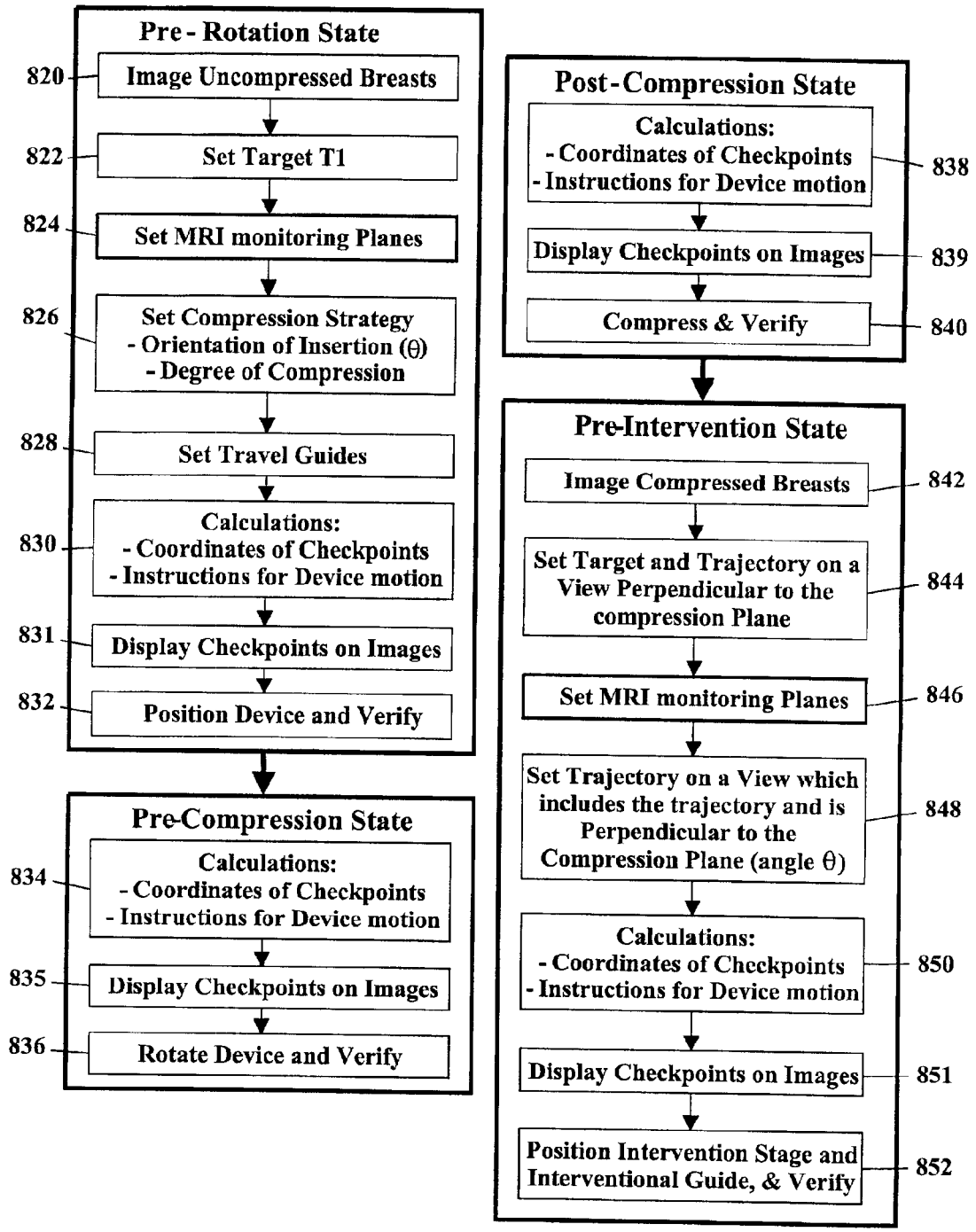
FIG. 17 is a detailed block diagram of an example of operation of a device within the scope of the invention.

Software:

Software will be used for planning the operation and controlling the actuators. The software will include components for: (a) visualization of the diagnostic MR images, (b) user selection of the target area, for example by means of a joystick-controlled cursor, (c) calculation of the prospective positions of the MRI visible markers (d) calculation of step-motor instructions and control of the motion drivers and (e) to provide the triggering signal for MR imaging. FIG. 17 illustrates the flow of the system operation and the involvement of the corresponding software components. The position of the device will be displayed with a graphical representation, together with the numerical values of its relative position to the target area. The system may be manual, facilitated by means of a joystick and keyboard. The user would control which particular motion will be activated by means of clicking on the 3D image and switching from the control to the choice modes by a single-key strike. A computer assisted operation, i.e., automatic calculation of system pathway after the operator has set the operation strategy, is currently under evaluation.

Example of Tests for the Positioning Device:

Mechanical Performance: The following components can be individually tested: (a) rotational motion of base, (b) linear motion of plate $CP_2$ for compression, (c) linear motion of the stage (d) angulation. The accuracy can be measured as follows: (1) set the component at the origin, (2) move to a distance L (or angle (theta), (3) record the value, (4) return to the origin and repeat the above. The repetition error will be measured as follows: (1) set the component at the origin, (2) move to a distance L (or angle (theta), (3) record the value, (4) return to the origin, (5) move to the same position, (6) record that value. The repetition error will be the difference of the two values. These measurements will be repeated and the average and standard deviation will be calculated for positions on the available range of motion to identify non-linearities. The same tests can be performed with the fully assembled system by defining composite motions, e.g. rotation, compression, height and angulation.

MRI Compatibility Site Tests of the Positioning Device

Eddy currents can distort the MR images and may arise when the fast switching magnetic field gradient induces electric currents on the metal parts of the device which, in turn, distorts of the local magnetic field. Accurate knowledge of such distortions is important since the probe guide will move inside a distorted space, misleading the calculation of the position of the system components. Studies may be performed using phantoms comprised of compartments with known dimensions filled with water doped with $CuSO_4$. Four phantoms will be used with grid separation of 1 cm and thickness of 2.5, 5, 7.5 and 10 cm. The phantoms will be secured with a wooden frame at a known position relative to the magnet isocenter allowing space for the device to be placed underneath. Multislice MR images, covering the entire area-of-operations of the device, will be collected using a spin echo sequence (TR/TE=500 ms/12 ms). One set of images will be collected without the device in place. Several sets of images will be collected with the device in-place for (I) different compressions, (ii) for each compression with the stage at several positions, and (iii) for several angulations of the probe guide. In these studies, the compression plate $CP_2$ will be moved from the fully extended position to the full compression allowed by the thickness of the phantom. The length of the compartment and the spatial position of the crossing points calculated from the images collected with the device in-place will be compared with these values from the images collected without the device. These data will be used to calculate the difference between the coordinate systems of the device and the scanner. This detailed data will be collected and used for a correction matrix to be incorporated in the software to correct these errors.

Unwanted proton signal: The proposed apparatus will be constructed with NMR inert materials, however, unwanted proton signals may originate from contamination in the materials or the hydraulic fluid. This may cause problems such as fold-in signal artifacts if the FOV is not set appropriately. To assess this problem, we can perform a similar set of tests to those described above. Initially, images will be collected without the device. Then images will be collected when the device is anchored in place with the hydraulic fluid drained. Finally images will be collected with the hydraulic lines loaded. For each case, we will collect images with progressively increased FOV. Then the images collected with the device (with and without hydraulic fluid) will be compared with those collected without in order to identify unwanted proton signals from the device and from the hydraulic network. Both studies probably would be conducted on an at least 1.5 Tesla scanner using the standard body RF coil of the system.

What is claimed:

1. A system for guiding a probe in a magnetic resonance imaging apparatus comprising:
   a first compression surface;
   a second compression surface aligned substantially parallel with the first compression surface wherein the first compression surface and the second compression surface are each positioned along a first axis;
   a compression adjuster adapted to adjust a distance between the first compression surface and the second compression surface along the first axis;
   a stage coupled to the first compression surface and the second compression surface and adapted to rotate on a second axis substantially orthogonal to the first axis, the second axis having a user selectable position; and
   a probe guide having an intervention axis and adapted to guide the probe for insertion into a region between the first compression surface and the second compression surface along the intervention axis.

2. The system of claim 1 further comprising a height adjuster coupled to the stage and adapted to adjust a height between the stage and a supporting surface.

3. The system of claim 2 further including a stage height remote control coupled to the height adjuster.

4. The system of claim 1 further comprising a lateral adjuster coupled to the stage and adapted to adjust a lateral distance between the stage and a supporting surface.

5. The system of claim 4 further including a stage lateral position remote control coupled to the lateral adjuster.

6. The system of claim 1 further comprising a probe guide angle adjuster coupled to the stage and the probe guide and adapted to adjust an angle between the probe guide and the stage.

7. The system of claim 6 further including a probe guide angle remote control coupled to the probe guide angle adjuster.

8. The system of claim 1 further comprising a probe guide height adjuster coupled to the stage and the probe guide and adapted to adjust a height of the probe guide relative to the stage.

9. The system of claim 8 further including a probe guide height remote control coupled to the probe guide height adjuster.

10. The system of claim 1 further comprising a probe guide depth stop adjuster coupled to the probe guide and adapted to adjust an insertion distance of a probe coupled to the probe guide.

11. The system of claim 10 further including a depth stop remote control coupled to the probe guide depth stop adjuster.

12. The system of claim 1 further comprising a patient supporting surface adapted to rotate on a supporting surface axis aligned orthogonal to the second axis and substantially parallel with a spine of a patient when a patient is positioned on the supporting surface.

13. The system of claim 12 further including a patient support remote control coupled to the patient supporting surface.

14. The system of claim 1 further including one or more linear actuators coupled to the compression adjuster.

15. The system of claim 14 further including one or more remote controls coupled to the one or more linear actuators.

16. The system of claim 1 further including a rotational actuator coupled to the stage.

17. The system of claim 16 further including a stage remote control coupled to the rotational actuator.

18. The system of claim 1 wherein the first compression surface includes a window.

19. The system of claim 18 wherein the window includes a permeable cover.

20. The system of claim 18 wherein the window includes a sterilizeable permeable cover.

21. The system of claim 18 wherein the window includes a permeable mylar cover.

22. The system of claim 1 wherein the probe guide is coupled to the rotational stage.

23. The system of claim 1 fabricated of magnetic resonance imaging (MRI) compatible material.

24. The system of claim 23 wherein the MRI compatible material includes plastic.

25. A system for guiding a probe in a magnetic resonance imaging apparatus comprising:
    a rotatable platform having a first rotational axis, the first rotational axis having a user selectable position;
    a first rigid structure substantially normal with, and coupled to, the platform;
    a second rigid structure substantially normal with, and coupled to, the platform;
    a compression adjuster coupled to the platform and adapted to adjust a distance between the first rigid structure and the second rigid structure;
    a guide, having a guide axis, coupled to the platform and aligned to direct the probe along the guide axis into a region disposed between the first rigid structure and the second rigid structure;
    a first remote control coupled to the guide and adapted to adjust an angle between the guide axis and the platform; and
    a second remote control coupled to the guide and adapted to adjust a distance between the guide axis and the platform.

26. The system of claim 25 further comprising a third remote control coupled to the guide and adapted to adjust a depth of insertion of a probe coupled to the guide.

27. The system of claim 25 further comprising a fourth remote control coupled to the platform and adapted for adjusting a vertical position of the platform relative to a patient support surface.

28. The system of claim 25 further comprising a fifth remote control coupled to the platform and adapted for adjusting a horizontal position of the platform relative to a patient support surface.

29. The system of claim 25 wherein the first rigid structure includes a passage to admit a probe coupled to the guide.

30. The system of claim 25 wherein the first rigid structure is adjustably coupled to the platform and the second rigid structure is immovably coupled to the platform.

* * * * *